United States Patent [19]

Russell

[11] Patent Number: 4,669,485

[45] Date of Patent: Jun. 2, 1987

[54] APPARATUS AND METHOD FOR CONTINUOUS NON-INVASIVE CARDIOVASCULAR MONITORING

[75] Inventor: Ted W. Russell, Northport, N.Y.

[73] Assignee: Cortronic Corporation, Ronkonkoma, N.Y.

[21] Appl. No.: 581,134

[22] Filed: Feb. 17, 1984

[51] Int. Cl.⁴ .............................................. A61B 5/02
[52] U.S. Cl. .................................... 128/679; 128/681; 128/677
[58] Field of Search ......................... 128/672, 677–686

[56] References Cited

U.S. PATENT DOCUMENTS

| | | | |
|---|---|---|---|
| 3,157,177 | 11/1964 | Smith | 128/679 |
| 3,348,534 | 10/1967 | Marx et al. | 128/679 |
| 3,581,734 | 6/1971 | Croslin | 128/679 |
| 3,903,872 | 9/1975 | Link | 128/681 |
| 4,009,709 | 3/1977 | Link et al. | 128/681 |
| 4,074,711 | 2/1978 | Link et al. | 128/680 |
| 4,105,021 | 8/1978 | Williams et al. | 128/683 |
| 4,216,779 | 8/1980 | Squires et al. | 128/682 |
| 4,245,648 | 1/1981 | Trimmer et al. | 128/680 |
| 4,262,675 | 4/1981 | Kubo et al. | 128/680 |
| 4,271,843 | 6/1981 | Flynn | 128/681 |
| 4,271,844 | 6/1981 | Croslin | 128/681 |
| 4,313,445 | 2/1982 | Georgi | 128/680 |
| 4,343,314 | 8/1982 | Sramek | 128/680 |
| 4,349,034 | 9/1982 | Ramsey, III | 128/681 |
| 4,378,807 | 4/1983 | Peterson et al. | 128/677 |
| 4,407,297 | 10/1983 | Croslin | 128/681 |
| 4,408,614 | 10/1983 | Weaver et al. | 128/680 |
| 4,418,700 | 12/1983 | Warner | 128/672 X |
| 4,437,469 | 3/1984 | Djordjevich et al. | 128/672 |
| 4,479,494 | 10/1984 | McEwen | 128/682 X |

FOREIGN PATENT DOCUMENTS

| | | | |
|---|---|---|---|
| 0517480 | 2/1972 | Switzerland . | |
| 2092309 | 8/1982 | United Kingdom | 128/672 |

OTHER PUBLICATIONS

Kinsner et al.; "Noncontact Microprocessor-Based Ocular Pulse Monitoring System"; *Computers in Ophthalmology*, 4-1979, pp. 212–219.

Bahr et al.; "The Automatic Arterial Tonometer";. *Engr. in Med. and Biol.*—*Proc. of Ann. Conf.* 1973, vol. 15, p. 259.

Bergel; "The Dynamic Elastic Properties of the Arterial Wall"; *J. Physiol.*, 1961, vol. 156, pp. 458–469.

Bergel; "The Static Elastic Properties of the Arterial Wall"; *J. Physiol.* 1961, pp. 445–457.

Geddes; "The Direct and Indirect Measurement of Blood Pressure"; 1970, pp. 77–83.

Flaud et al.; "Ecoulements Pulses Dans Les Tuyaux Viscoelastiques"; Applic. a L'Etude De La Circ. Sanguine, *Journal De Physique*, vol. 35, No. 11; pp. 869–882.

Flaud et al.; Dispositie Experimental Pour La Modelisation De L'Ecoulement Sanguin Dans Les Arteres; *Revue De Physique Appliquee*, pp. 61–67.

*Primary Examiner*—Kyle L. Howell
*Assistant Examiner*—Angela D. Sykes
*Attorney, Agent, or Firm*—Stanger, Michaelson and Einschlag

[57] ABSTRACT

Apparatus and related methods for continuous long-term non-invasive measurement of the pressure of a pulsatile fluid flowing through a flexible tube, particularly human arterial blood flow, is disclosed. Specifically, the apparatus provides a continuous calibrated pressure measurement by first undertaking a "calibration" phase comprised of determining the pressure at various pre-defined conditions of flow and, in reponse thereto, ascertaining the values of a plurality of coefficients each of which is associated with a corresponding term in a pre-defined function that characterizes fluid pressure in relation to pulsatile displacement of the wall of the tube; and second, undertaking a "continuous monitoring" phase comprised of determining each subsequently occurring pressure value as the pre-defined function of each corresponding pulsatile wall displacement value, and re-initiating the calibration phase at the expiration of pre-defined time intervals which adaptively change based upon current and prior results. Methods, which are particularly useful in conjunction with the disclosed apparatus, for ascertaining systolic and diastolic arterial blood pressure values are also disclosed.

57 Claims, 58 Drawing Figures

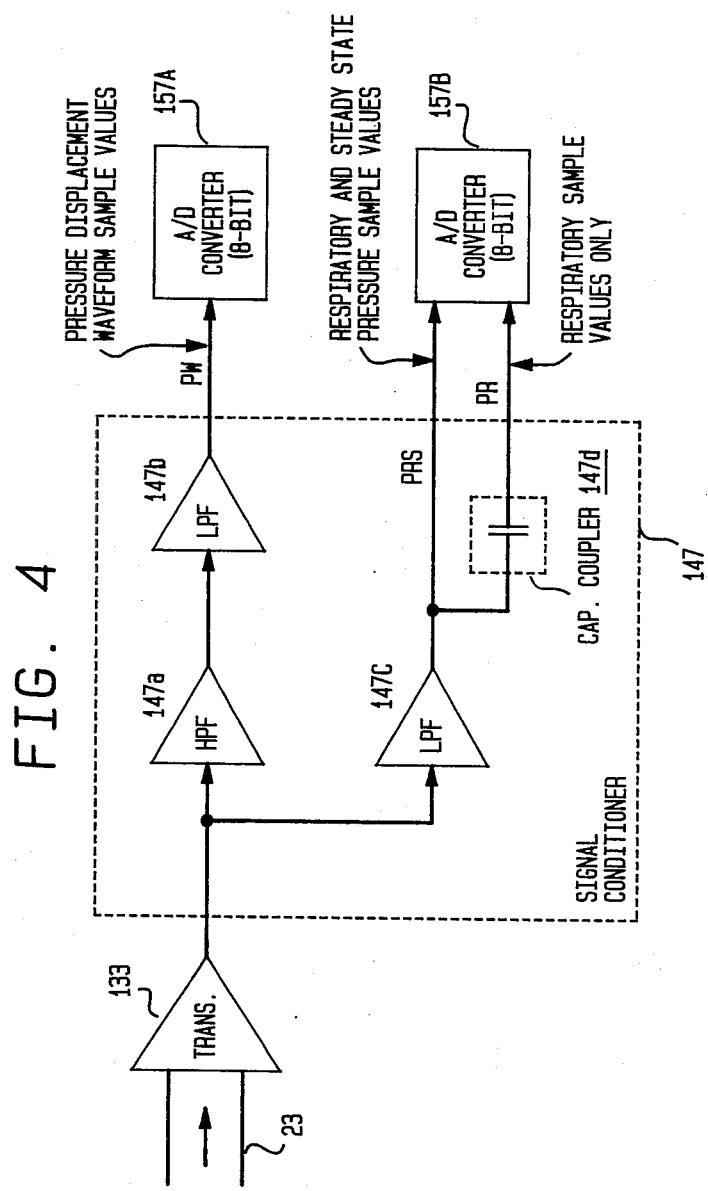

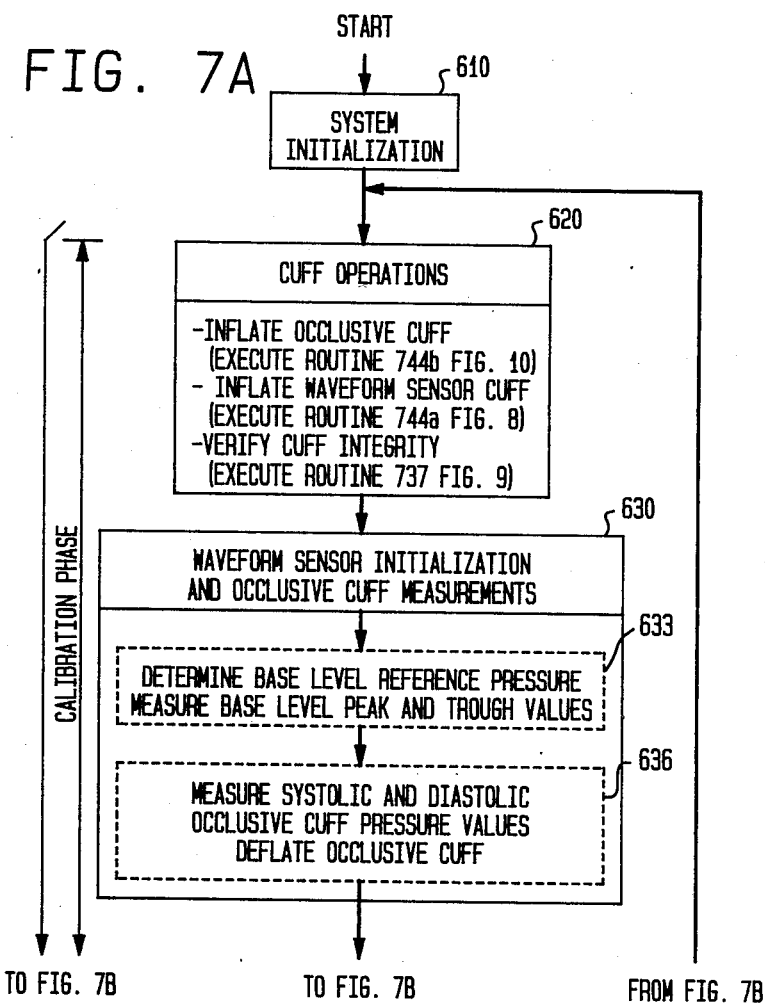

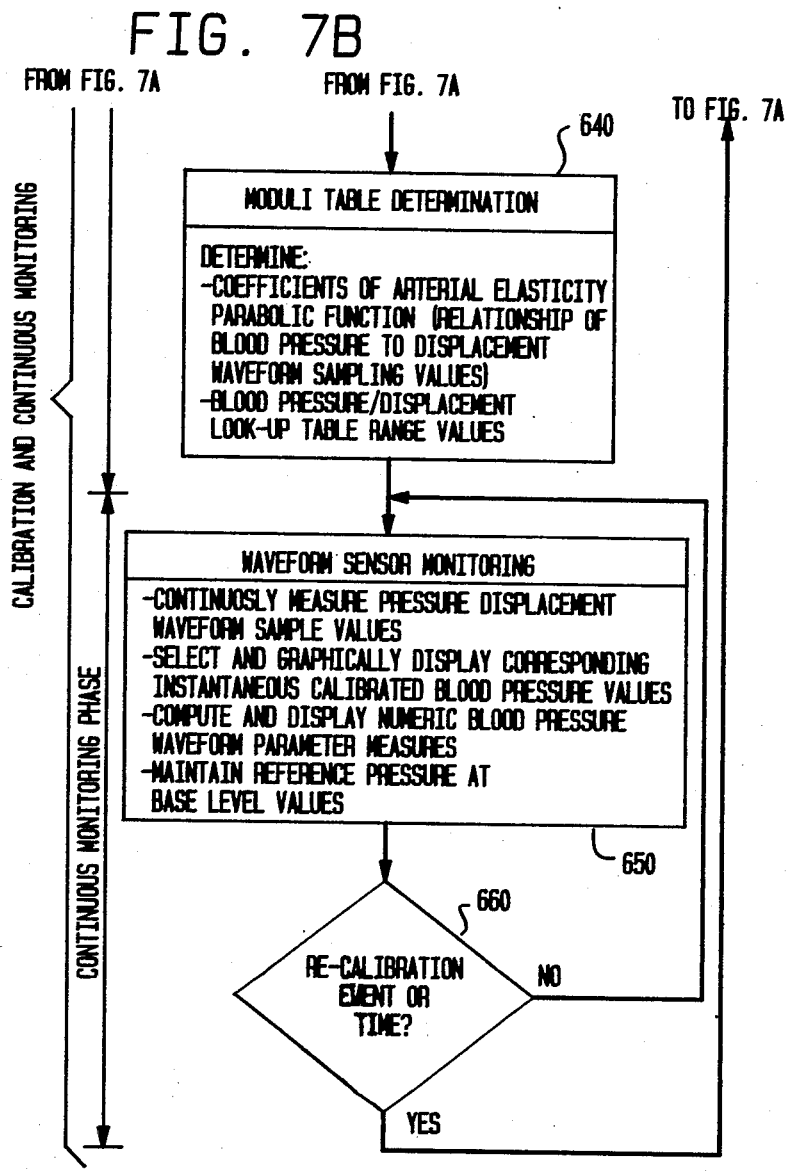

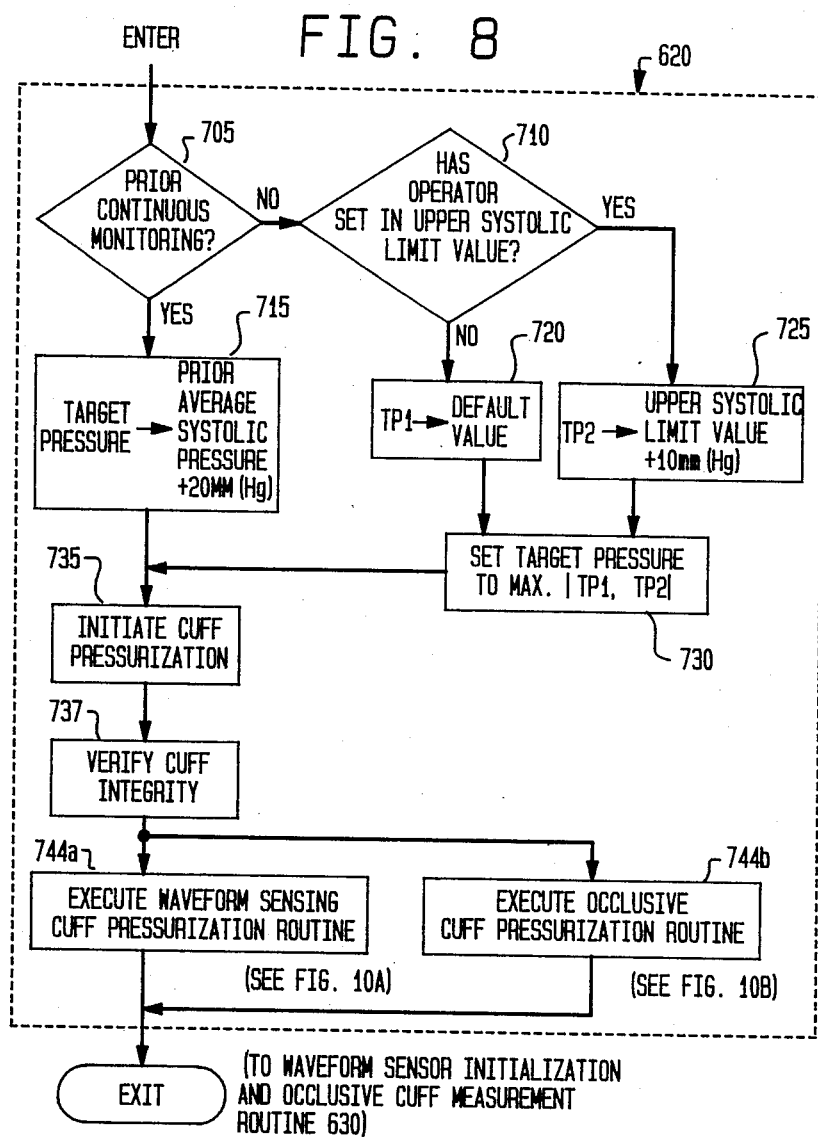

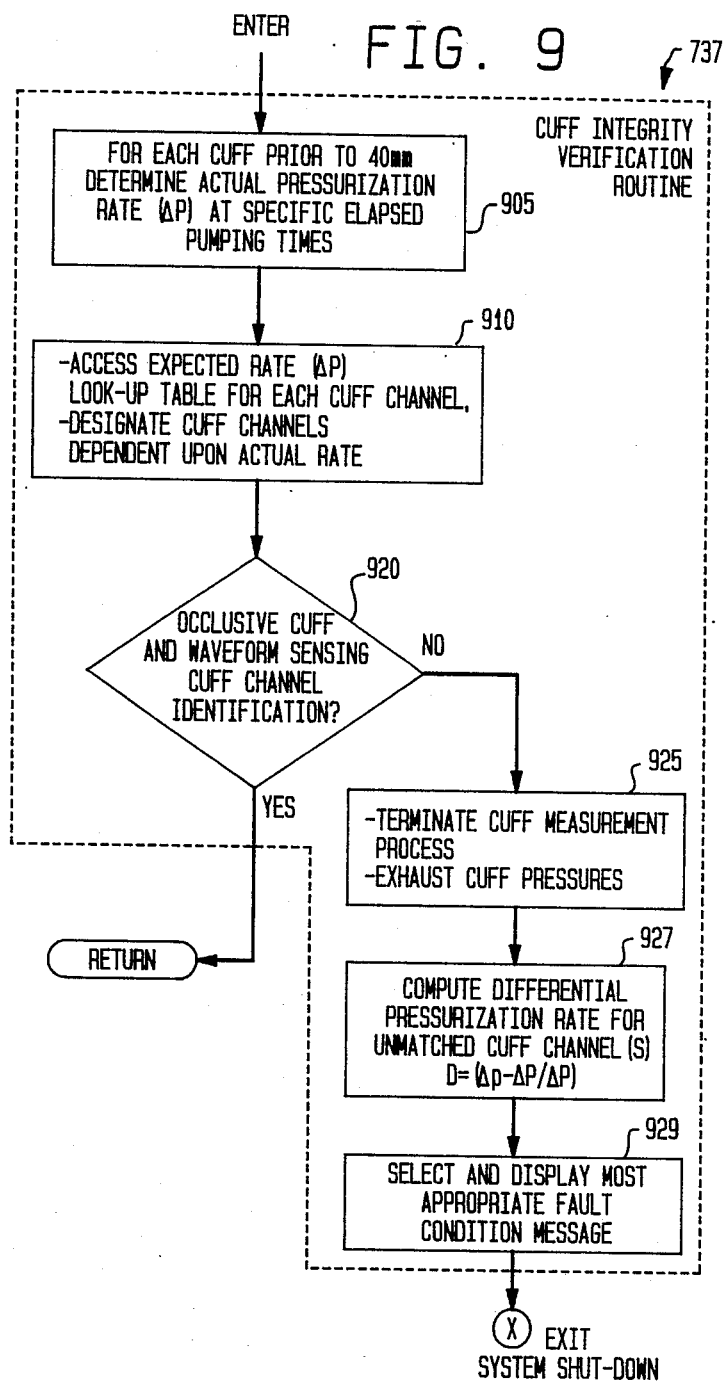

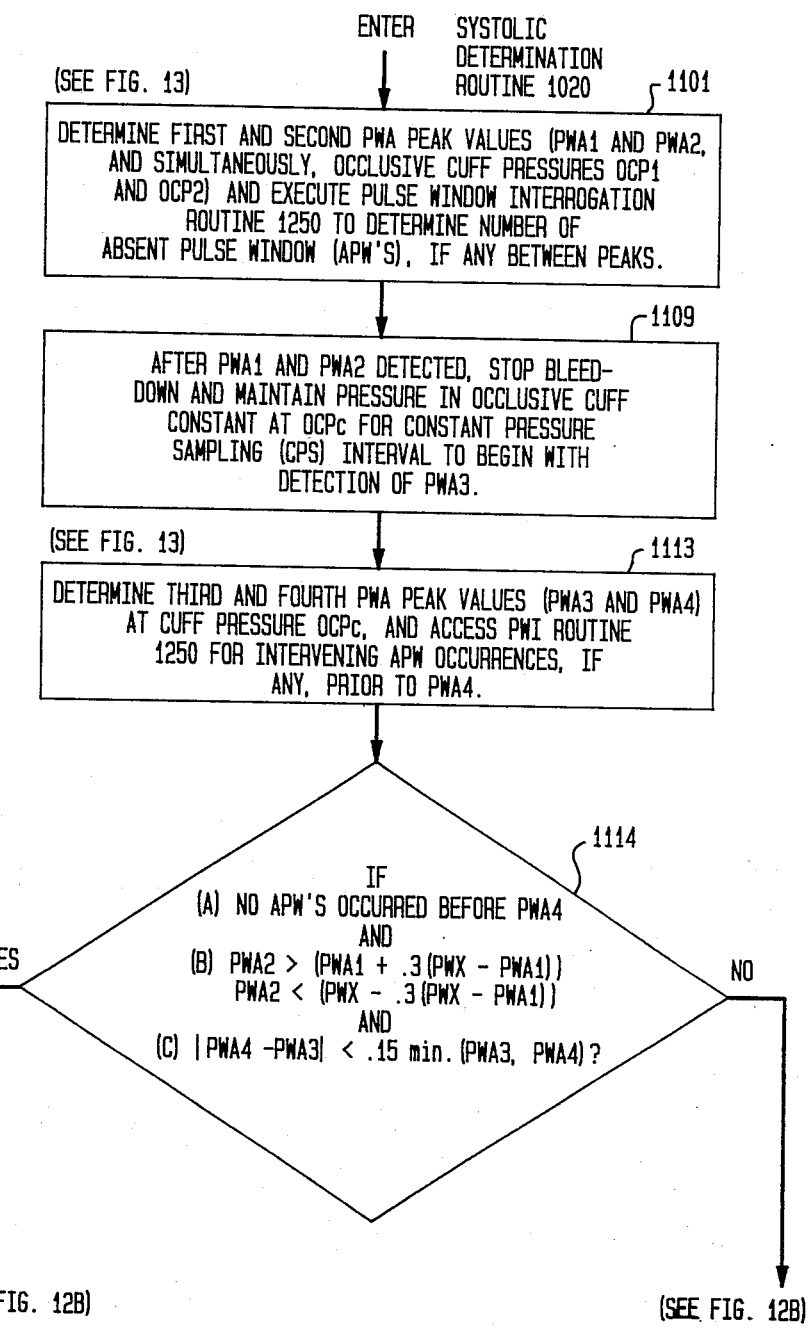

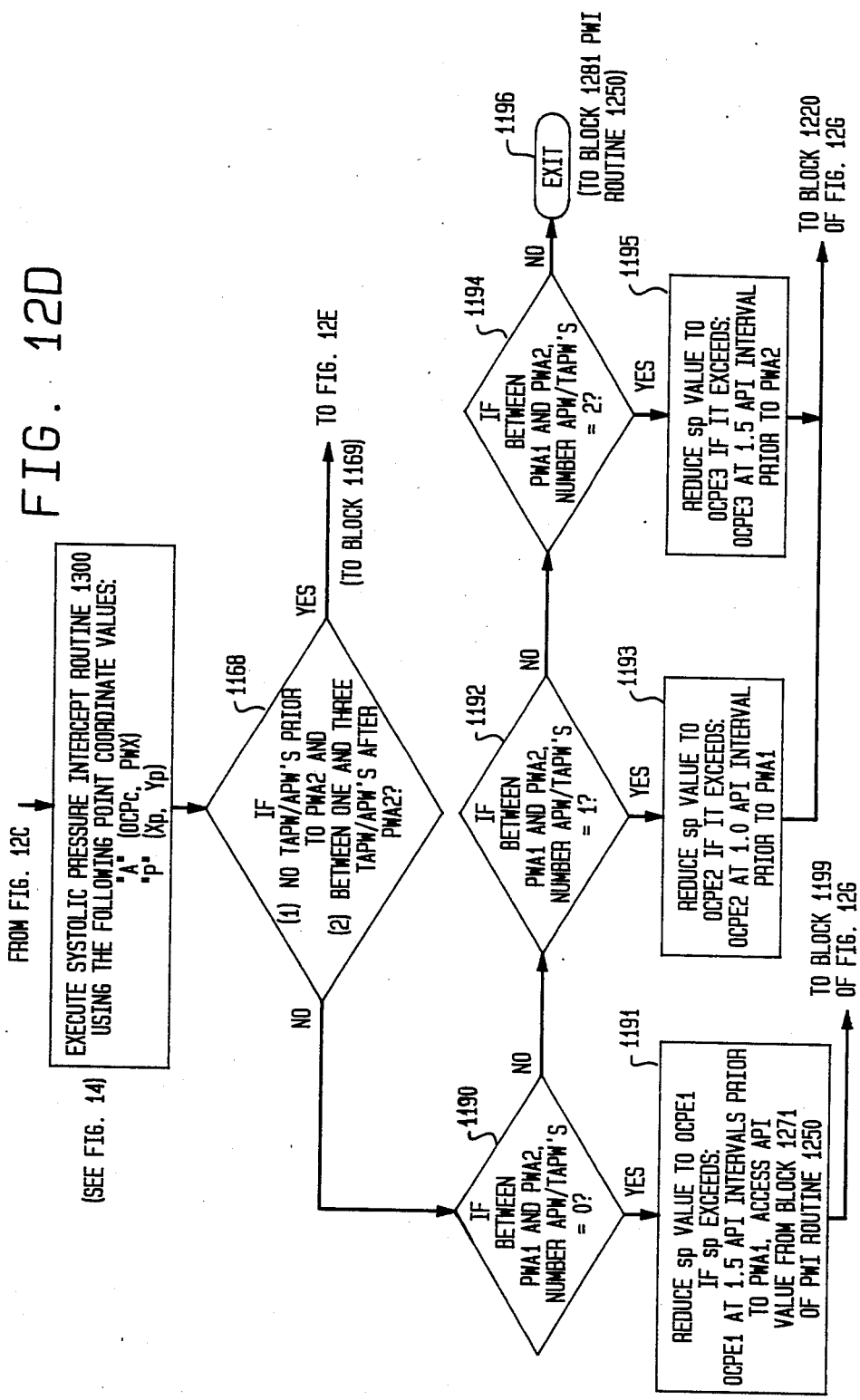

FIG. 12F  FROM FIG. 12E
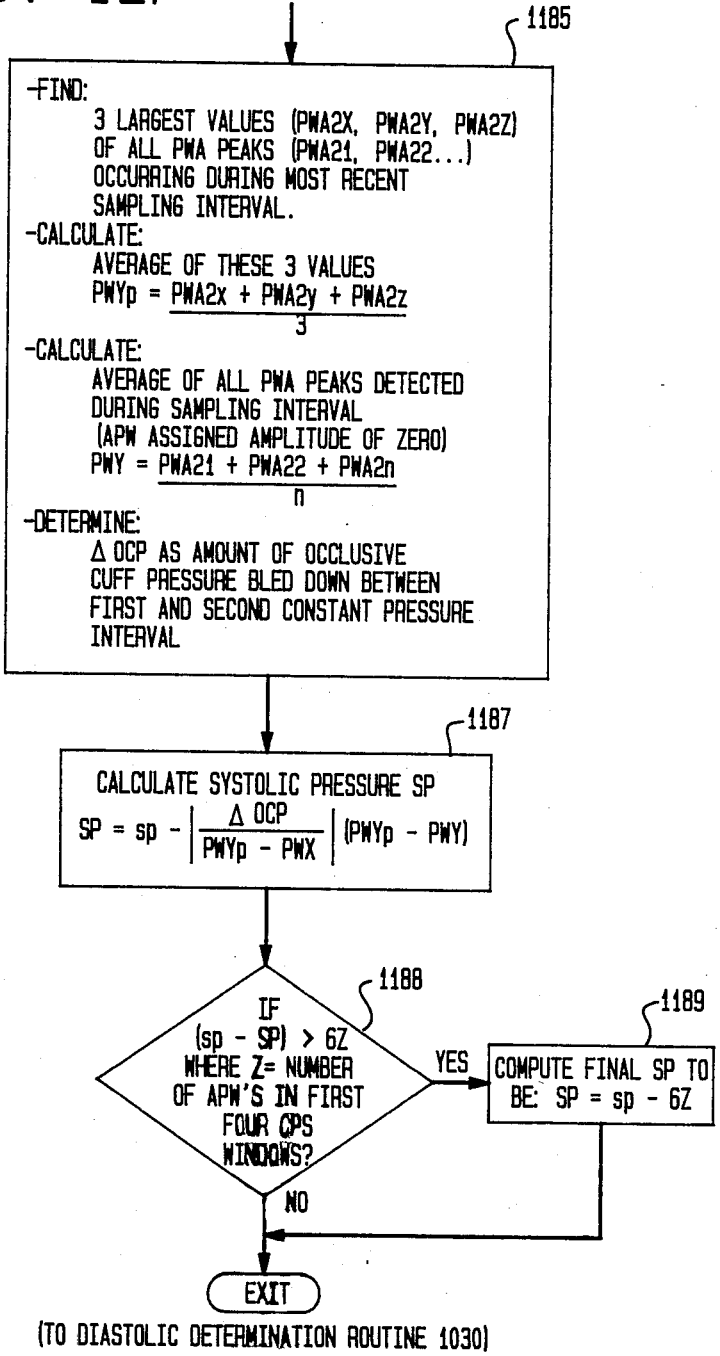
(TO DIASTOLIC DETERMINATION ROUTINE 1030)

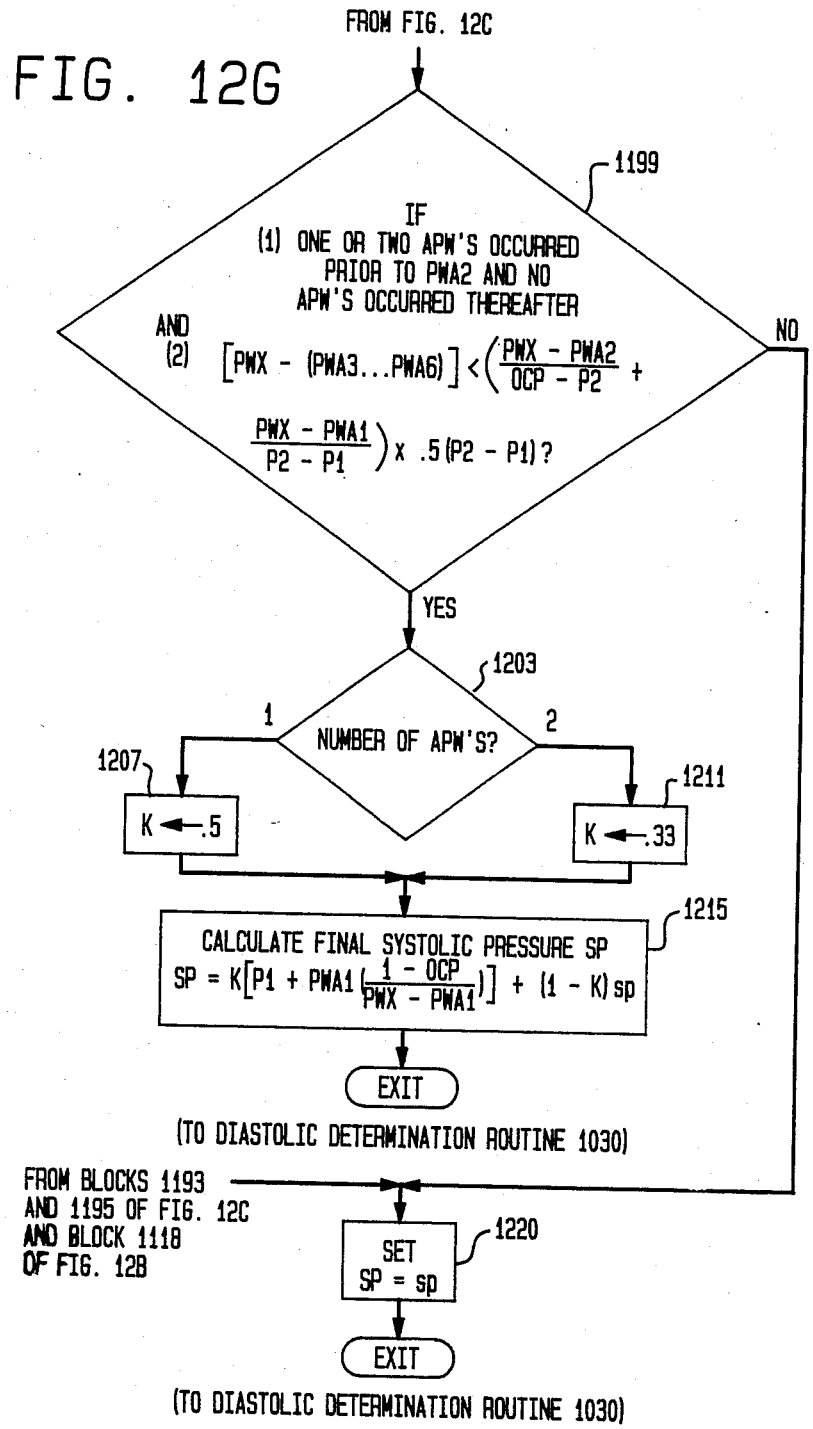

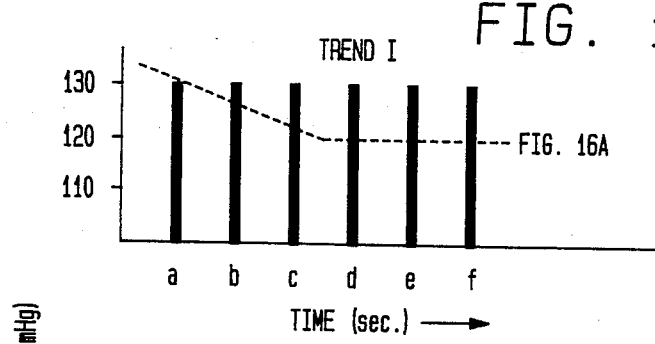
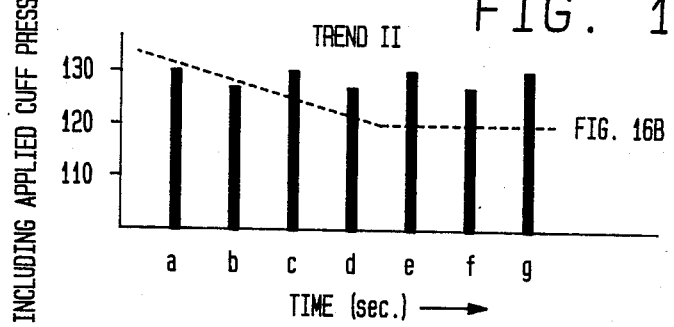
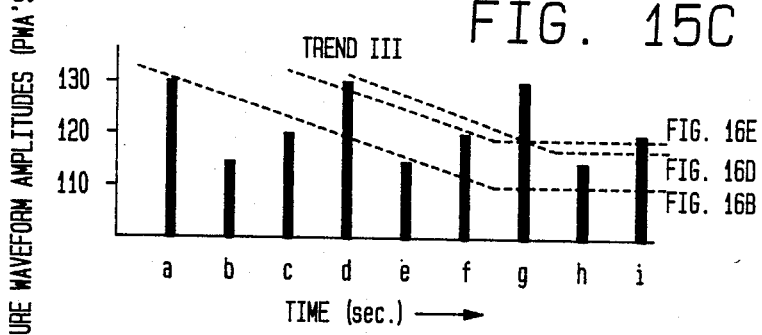
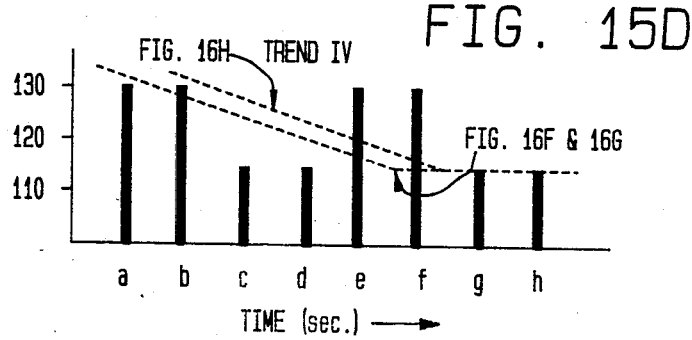

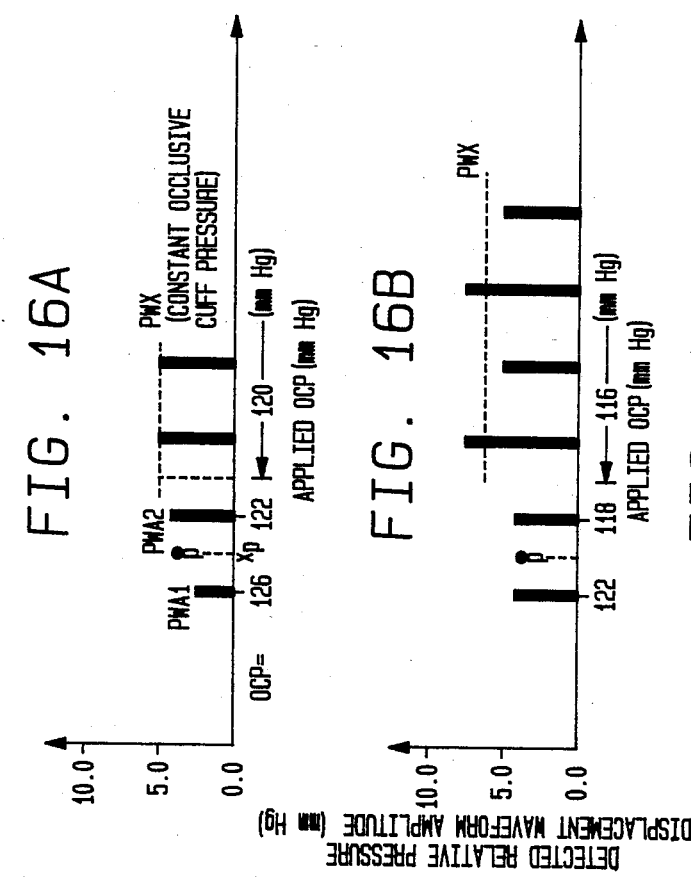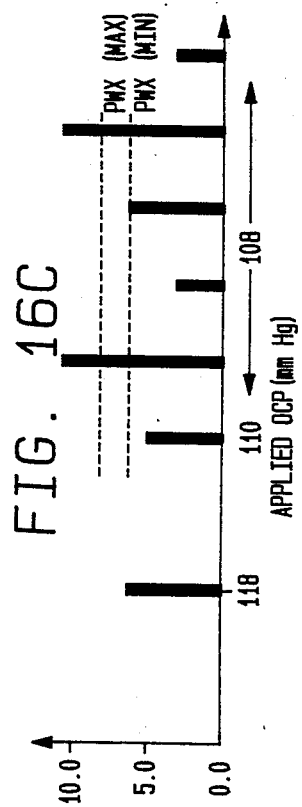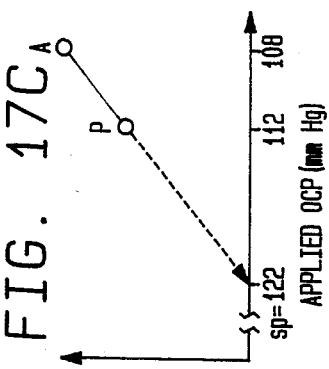

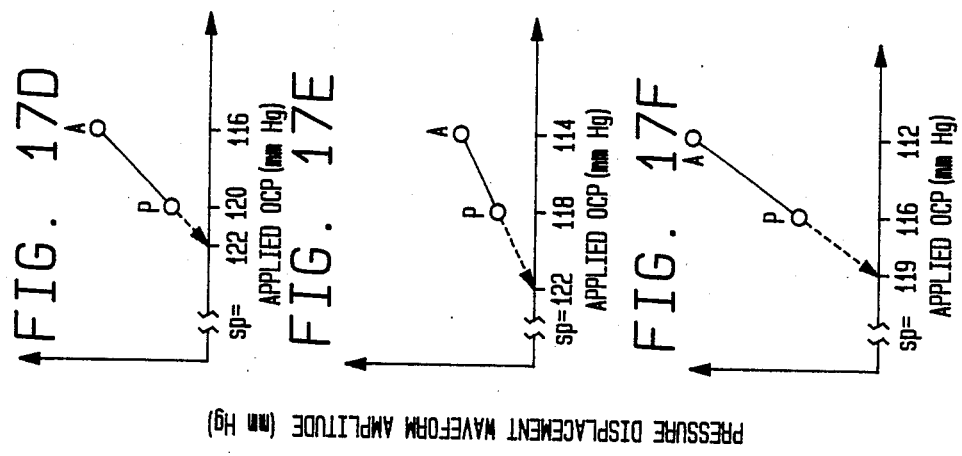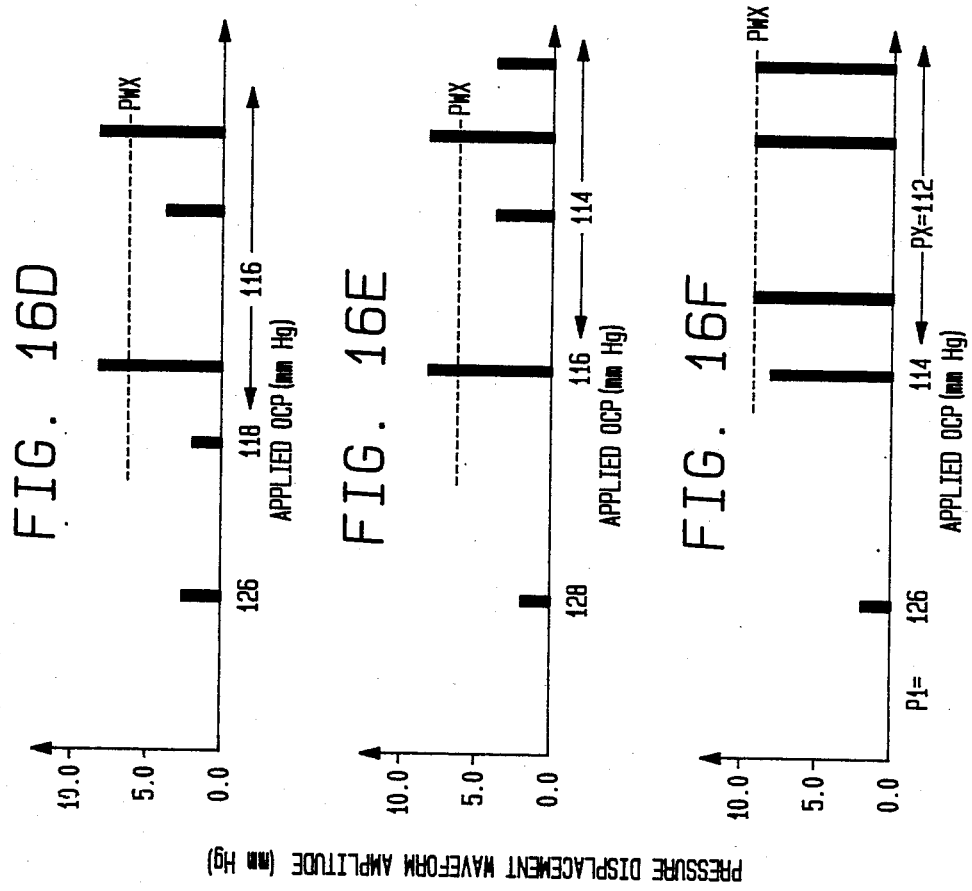

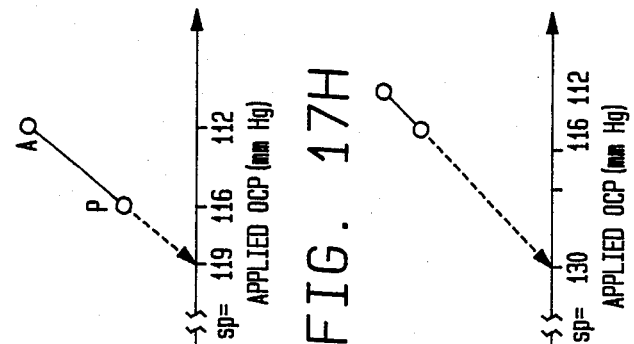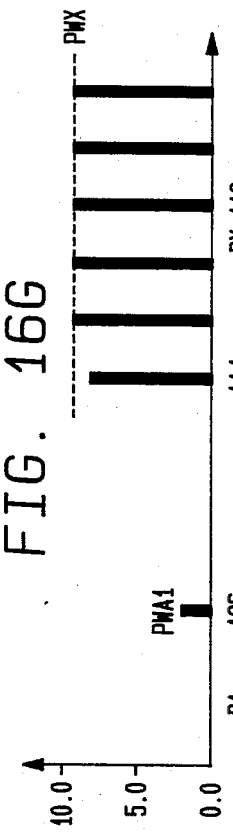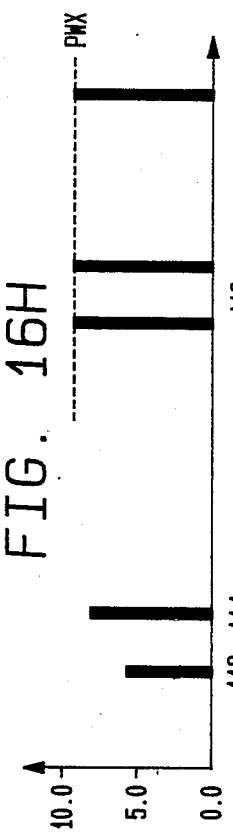

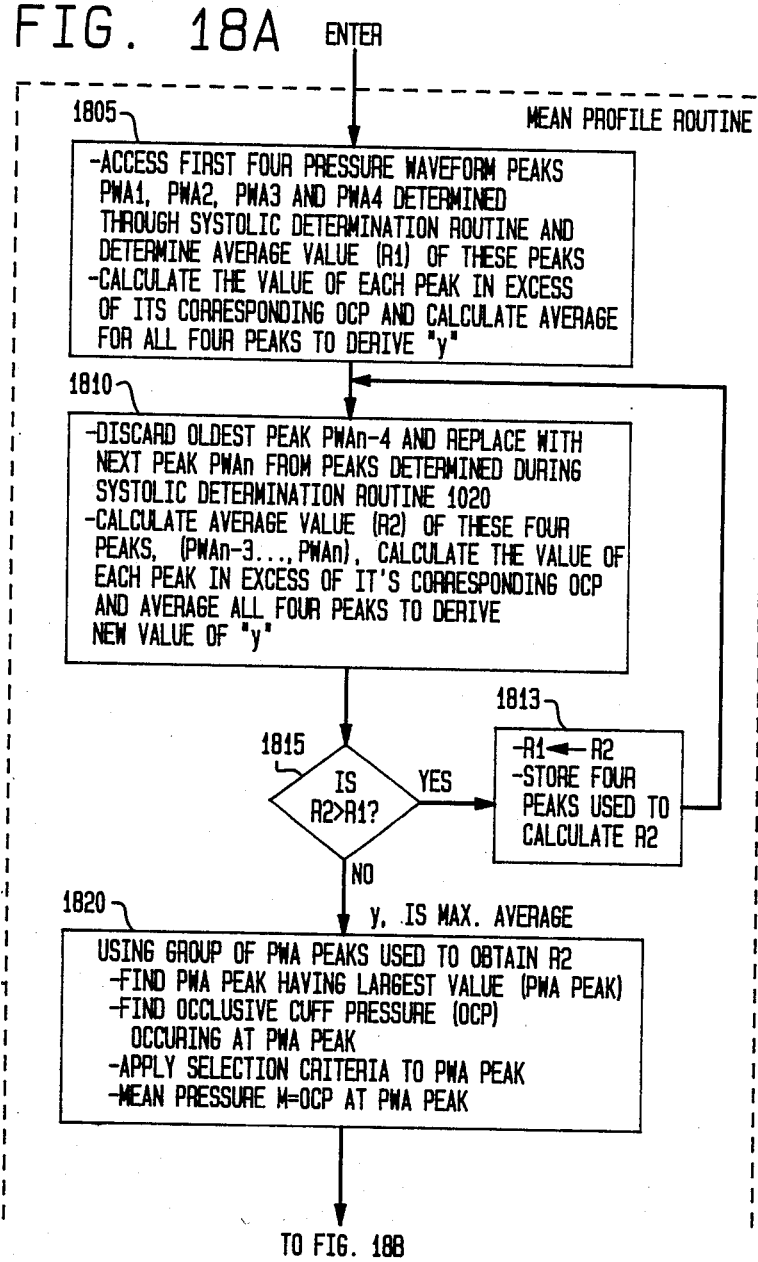

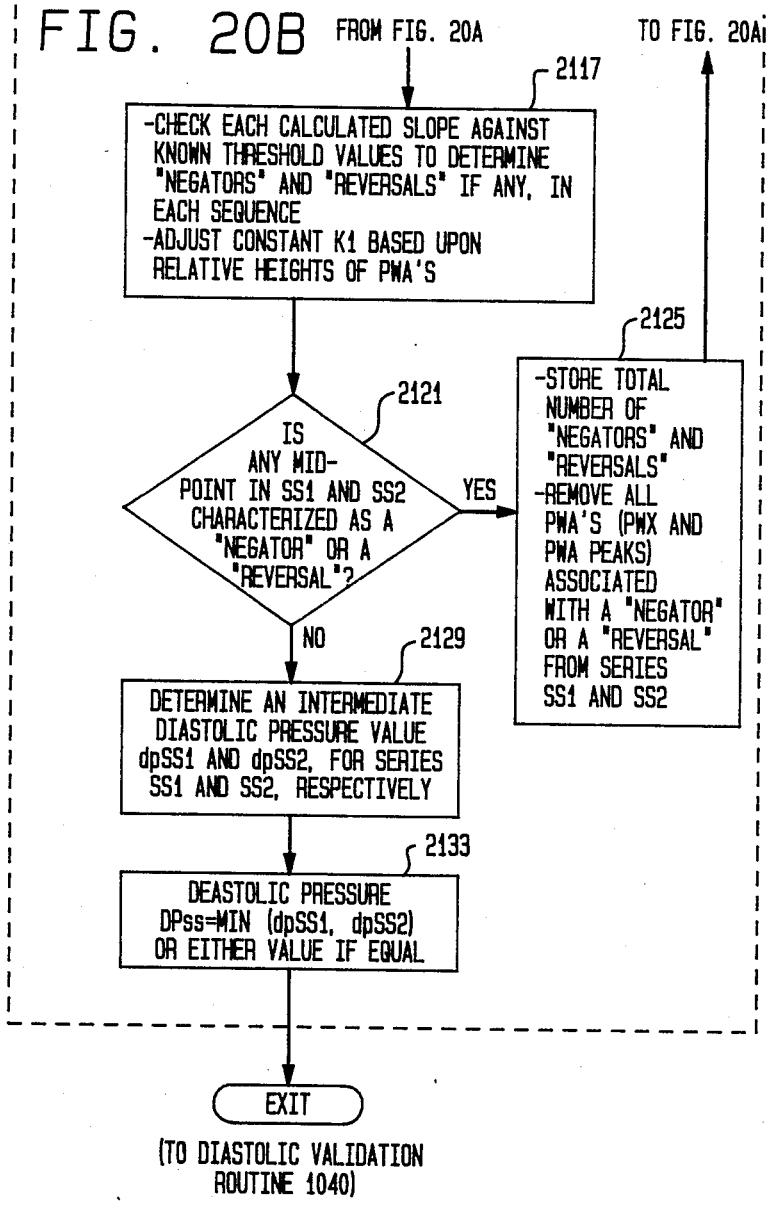

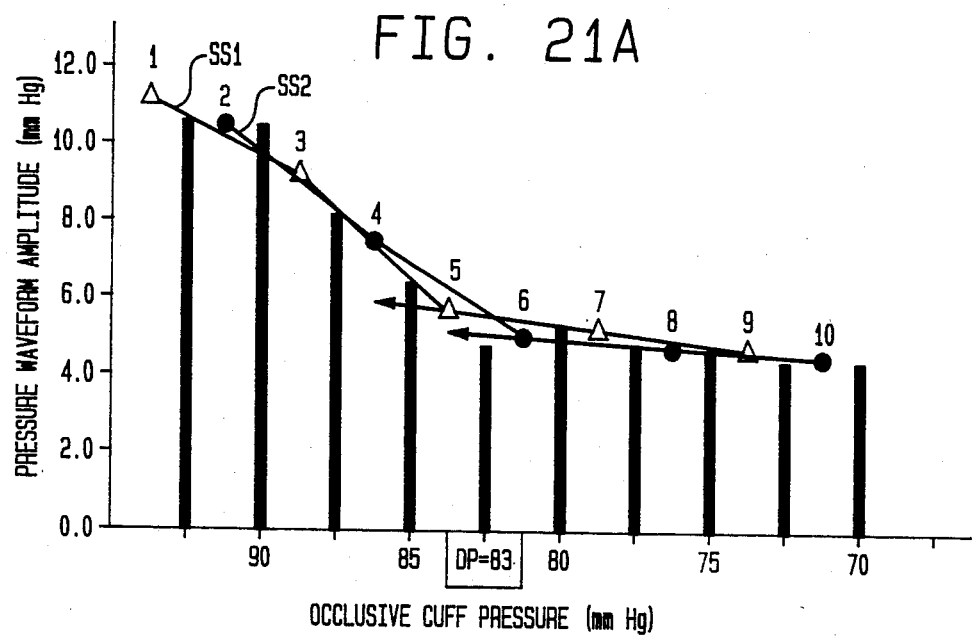
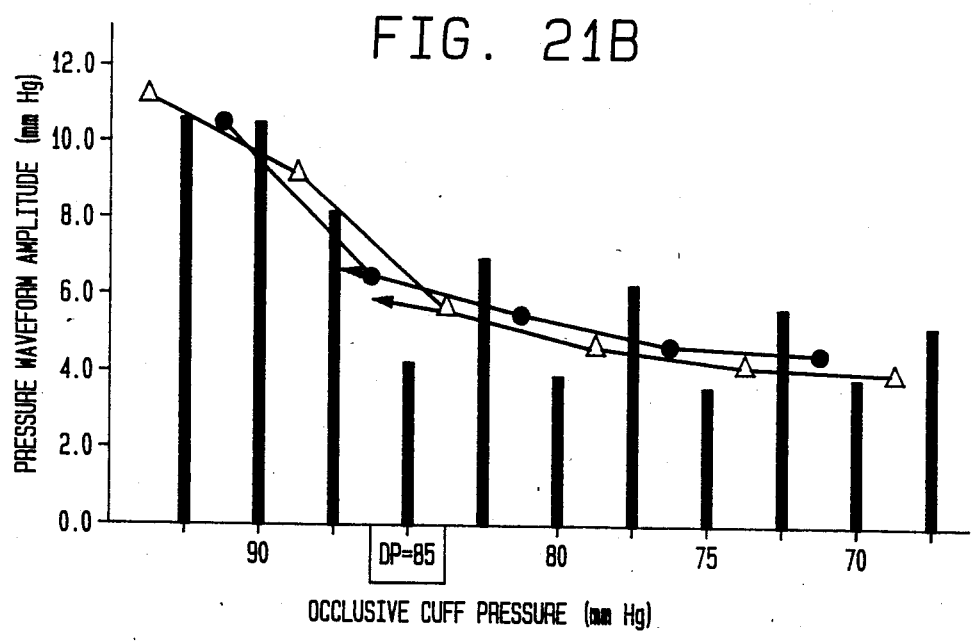

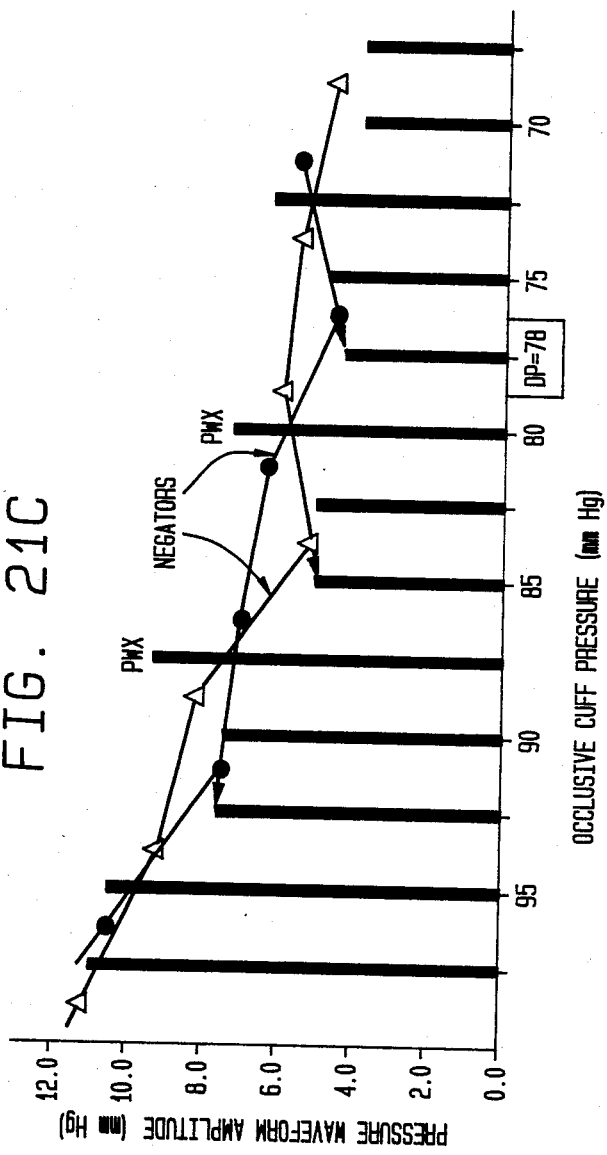

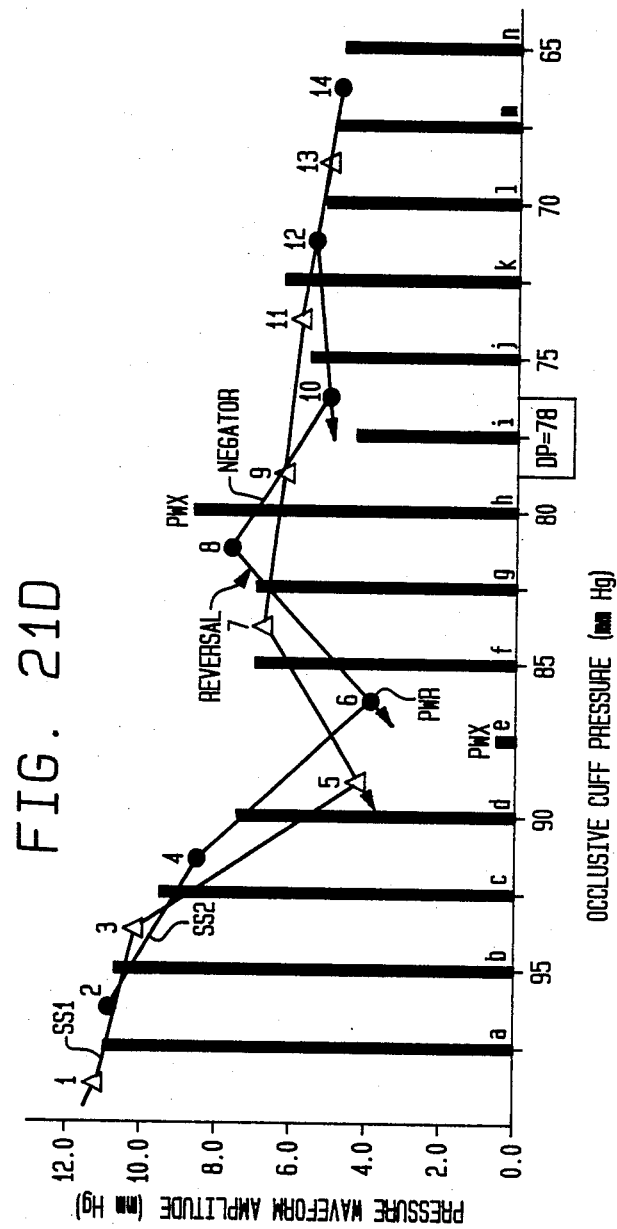

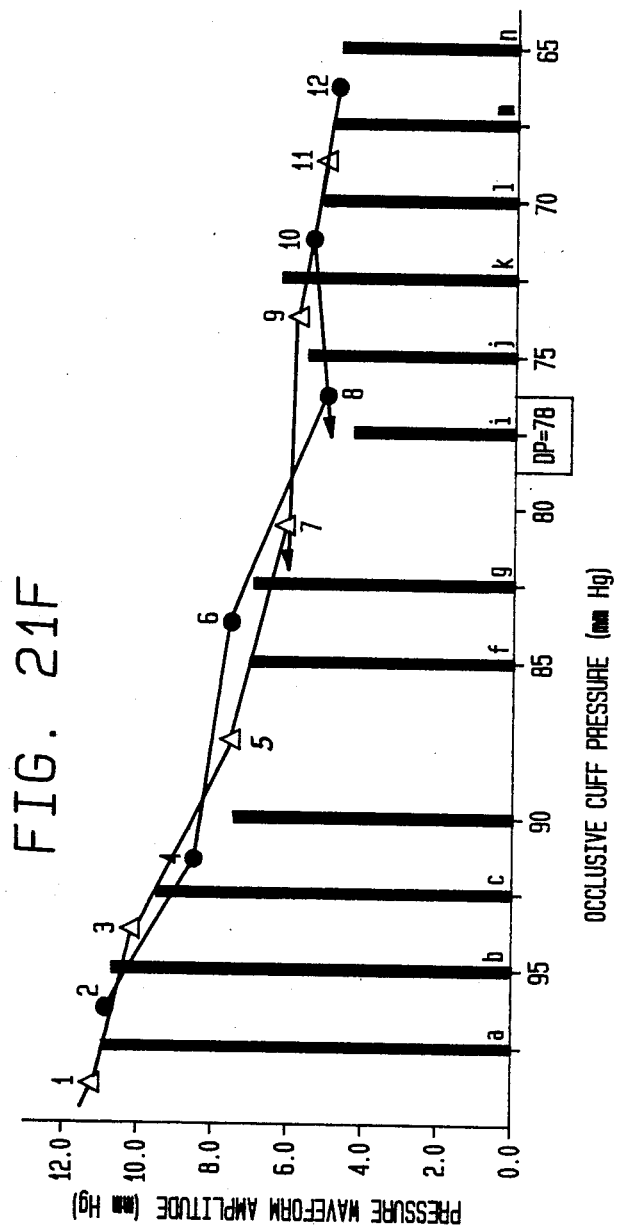

APPARATUS AND METHOD FOR CONTINUOUS NON-INVASIVE CARDIOVASCULAR MONITORING

BACKGROUND OF THE INVENTION

1. Field of the Invention

The invention relates to an apparatus and various methods used therein for continuous non-invasive measurement of the pressure of a pulsatile fluid flowing through a flexible tube over relatively long time periods, with particular applicability to the measurement of human arterial blood pressure and other related cardiovascular parameters.

2. Description of the Prior Art

Often a need arises to monitor pulsatile fluid pressure in a vessel where a number of practical considerations preclude direct invasive measurement, i.e. using an appropriate pressure sensor directly implanted through the vessel and maintained in a suitable position within the fluidic flow. Considerations of this nature include avoiding: contamination of the fluid or its immediate environment by any foreign matter carried by the sensor, coagulation of the fluid, corrosive deterioration caused to the sensor by direct contact with the fluid, fluid loss from the vessel, or physical damage to the flexible vessel that contains the fluid.

These considerations have particular applicability to the measurement of arterial blood pressure of human (or other animal) patients or subjects. In practice, invasive pressure monitoring generally entails a surgical cutdown and arterial penetration using a hypodermic needle (cannula) through which pulsatile fluidic forces attributable to arterial blood flow are routed to a suitable pressure transducer. However, various medical health care risks associated with invading the human body, such as clotting, infection, emboli obstructions to flow, and/or major blood loss generally limit the use of invasive blood pressure monitoring systems to the most critical of acute care hospital patient monitoring situations. To minimize these risks, invasive monitoring is almost always used in conjunction with intravenous application of fluids to the patient. Disadvantageously, the various fluidic, mechanical and electrical components generally used in invasive systems are not only complex and fragile, but also require specialized calibration before use, as well as frequent surveillance by specially qualified staff. In spite of this surveillance, invasive systems often do not remain calibrated during prolonged periods of use and, as a result, often produce inaccurate and potentially misleading patient blood pressure measurements.

Consequently, over the years several techniques have been developed for non-invasive arterial blood pressure measurement. In general, these techniques rely upon attaching an inflatable cuff around an extremity (limb), which is typically an upper arm, of a human patient. Once attached, the air pressure existing within the cuff is increased to a value commonly referred to as "suprasystolic," i.e., a pressure in excess of that minimally necessary to completely occlude a major artery existing within the extremity and situated near its surface. Thereafter, blood pressure is most commonly estimated by detecting well-known "Korotkoff" sounds using a stethoscope, a microphone, or an ultrasonic detector placed on the limb near the artery. These Korotkoff sounds are produced by the artery and, more particularly, by disturbances in the arterial blood flow due to partial occlusions of the artery caused by the externally applied cuff pressure. As the cuff pressure decreases and the extent of occlusion is reduced, various classic phases of sound change are usually heard until the artery is no longer occluded by any appreciable amount. Specifically, as the cuff pressure is reduced from suprasystolic, the maximum value of pulsatile blood pressure commonly referred to as systolic pressure, is usually taken to be equal to the cuff pressure at the time the first Korotkoff sound is detected. Thereafter, the minimum or so-called "diastolic pressure" value of pulsatile arterial pressure is usually identified in conjunction with the occurrence of one of two other Korotkoff phases: either the so-called fifth phase when silence occurs or the so-called fourth phase which corresponds to a cuff pressure of about 5–10 mm(Hg) higher than that occurring at the fifth phase. Manual pressure readings for systolic and diastolic are determined by identifying each desired phase, and, as the cuff pressure continually decreases, simultaneously noting the scale value in mm(Hg) that corresponds to the height of a mercury column (or the pointer on an aneroid guage) which is pneumatically connected to the cuff air pressure. Devices of this sort are commonly referred to as "sphygmomanometers."

Unfortunately, the accuracy of any non-invasive sphygmomanometer type blood pressure measurement system, typified by that described above, is largely dependent on the skill and hearing acuity of its user in detecting the rather subtle sound changes (such as the very gradual transition to silence after the fourth phase occurs), and, simultaneously therewith, determining the exact level of the mercury column. In addition, dexterity, sensory limitations and inexperience of the user; interference of environmental noises, and the need to frequently calibrate the measurement system often occur and all contribute to produce highly inconsistent results. This inconsistency is a widely known characteristic of sphygmomanometric systems.

Consequently, in an endeavour to minimize inconsistent results, many attempts have occurred in the art to automate the process of sphygmomanometric measurement. Specifically, these attempts involve using electronic processing circuitry to automatically determine the desired phases of Korotkoff sound change and the simultaneously occurring systolic and diastolic cuff pressure values.

These attempts are typified by the systems disclosed in U.S. Pat. Nos. 3,581,734 (issued to Croslin et al on June 1, 1971); 4,245,648 (issued to Trimmer et al on Jan. 20, 1981) and 4,271,844 (issued to Croslin on June 9, 1981). Each of these three patents discloses a computerized sphygmomanometer measurement system in which an occlusive cuff is attached around a limb of a patient. The cuff is then inflated, either manually or automatically by an electrically driven air pump which is controlled through either a computer or a hard-wired digital circuit. In each of these systems, the cuff is inflated to a suprasystolic occluding pressure prior to taking (sampling) any blood pressure measurement data. Then, by automatically undertaking various detection and determination processes, as well as deflating (bleedingdown) the occlusive cuff, these systems attempt to eliminate many of the above-described manual steps that can cause measurement error in manual sphygmomanometer systems known to the art. Unfortunately, these automated sphygmomanometer systems are incapable of reliably and consistently representing the true status of blood pressure, in the same manner as provided by direct invasive monitors that are widely accepted as the "standard of blood pressure measurement accuracy".

Specifically, sphygmomanometer systems commonly produce misrepresentative results due to a number of factors that are generally transparent to or incapable of being compensated by the practioner-user. One such factor is the impracticality of causing the pressure of any deflating occlusive cuff known in the art to be made equal to the true peak systolic pressure value of any one or more intra-arterial pressure waveforms such that the measured cuff pressure is an accurate representation of systolic. This impracticality results from the fact that any pulsatile intra-arterial peak pressure value exists for only a short interval of time, (e.g. usually less than 5% of the time). Inasmuch as the timing of cuff pressure bleed-down is a random variable, the cuff pressure is typically lower than true systolic peak pressure by random amounts, e.g., up to 10 mm(Hg), depending on the deflation rate used before the desired Korotkoff or pressure displacement waveform signal occurs—which indicates when the cuff pressure is to be measured and designated as the systolic measurement value. A second factor is the apparent lack of any uniform and accurate diastolic determination method in systems known to the art. Specifically, either one of two Korotkoff phases, i.e., the fourth and fifth pnase, each of which produces consistently different measurement values have found wide use in prior art systems. Also, these diastolic measurement methods known in the art often determine diastolic pressure as the value of occlusive cuff pressure whenever it exceeds a certain threshold. Such a threshold value is primarily dependent on the cuff pressure at the mean arterial blood pressure instead of other more relevant and accurate independent physiologic variables. Moreover, these methods are generally premised on an assumed linear relationship existing between amplitude values at mean and diastolic pressure and linearly extrapolate the diastolic pressure value based upon the mean pressure value. Accordingly, these measurement methods have the unfortunate effect of assuming somewhat erroneously, that a single fixed linear elasticity relationsnip defines the stress/strain (e.g. pressure/displacement) characteristics of the artery walls of all patients for whom blood pressure is to be non-invasively measured—thereby resulting in an inaccurate determination of the true diastolic pressure value. Lastly, a third factor is that systolic and diastolic pressures commonly vary by differing amounts from one heart-beat to the next due to several physiologic factors for both normal and critically ill patients. Unfortunately, any combination of these factors serves to over- or under-state not only the value of blood pressure, but also more importantly changes in arterial blood pressure occurring over time between successive measurements taken from any one patient.

Moreover, these prior art systems not only lack the capability of accurately portraying the arterial blood pressure associated with individual heart-beats, but also disadvantageously they generally produce only one systolic and diastolic reading during a measurement cycle that can span between 20 and 100 successive heartbeats. To properly represent the true status of blood pressure on a heart-beat to heart-beat basis, a much higher sampling rate is necessary. However, if any of these sphygmomanometer systems were used to measure arterial blood pressure variations on a continuous heartbeat-by-heartbeat basis, then the occlusive cuff would need to be repetitively and successively inflated to a suprasystolic pressure and possibly to atmospheric pressure over many short successive intervals of time, such as, for example, 10 times per second, as is disclosed in U.S. Pat. No. 4,343,314 (issued to Sramek on Aug. 10, 1982). Unfortunately, prevailing medical opinion is that any patient wearing an occlusive cuff cannot be continuously subjected to either elevated cuff pressures more than about 30% of the time during which the cuff is being worn or repetitive cycling of cuff pressure between suprasystolic and sub-diastolic pressures on the order of more than once every one to three minutes, without experiencing significant discomfort, trauma, and possible physiologic damage.

A typical repetitive cycling sphygmomanometer measurement system known to the art which attempts to minimize patient discomfort is disclosed in U.S. Pat. No. 4,378,807 (issued to Peterson et al on Apr. 5, 1983). As described therein, a control circuit automatically initiates one cycle of occlusive cuff inflation and bleed-down deflation only after a rather long pre-defined interval of time typically on the order of 7.5 to 60 minutes has elapsed. Unfortunately, pressure readings (one systolic and one diastolic) are only taken at the conclusion of this relatively long interval. As a result, the amount of measurement data is insufficient to determine short and long term trends and variability in blood pressure, as well as to identify, with any degree of reliability, any irregular heart-beat pulsations. Thus, such a system is unsuitable for prolonged continuous blood pressure monitoring of the critical patients. Consequently, invasive pressure monitoring systems—even in spite of their attendant health risks, as discussed above—are used to continuously measure and display the pressure waveform for each heart-beat and to compute the systolic, diastolic and mean pressure values based upon averages of a number (typically 4-6) of successive heartbeats.

An alternate well-known scheme of non-invasive monitoring involves measuring arterial wall displacement (i.e., radial distension of the artery wall) produced by pulsatile arterial blood pressure and then translating the measured displacement into an instantaneous blood pressure value. These measurements and translations would, if performed at a sufficiently rapid rate, appear to be continuous, i.e. result in the display of an uninterrupted trend of sequentially-occurring pressure waveforms showing substantial detail of the pulsatile nature of each waveform, much in the same fashion as obtained through an invasive monitor. See, for example, P. Flaud et al, "Pulsed Flows in Viscoelastic Pipes. Application to Blood Circulation", *Journal of Physics* (France) Vol 35, No. 11, November 1974, pages 869-882 and P. Flaud et al, "An Experimental Device for Modelling Arterial Blood Flow," *Review of Physical Applications* (France) Vol. 10, No. 2, March 1975, pages 61-67, which disclose that radial displacement of the arterial wall is related to intra-arterial blood pressure changes. However, the relative magnitude of wall displacement is also directly related to the elasticity of the wall of the arterial vessel. Unfortunately, arterial elasticity not only varies significantly from patient to patient but also varies at different locations along each artery, as well as at different times for the same patient. Thus, a noninvasive pressure monitoring system that relies on relative arterial wall displacement, requires that its measurements first be calibrated against pressure measurements taken by a separate reference device, such as an occlusive cuff, which would then serve as a calibration reference for subsequent pressure values based upon arterial wall displacement measurements.

Hence, in view of the drawbacks associated with prior art non-invasive measurement systems, continuous blood pressure monitoring systems known and used in the art are generally invasive and thus rely on intruding a major artery of the patient.

SUMMARY OF THE INVENTION

An object of the present invention is to provide a system which can continuously and non-invasively monitor the pressure of a pulsatile fluid flowing through a flexible tube.

A specific object is to provide an accurate continuous non-invasive blood pressure monitoring system which can be attached to a patient and operated for either relatively brief or substantially prolonged periods of time without any physiologic risks and/or significant discomfort to that patient.

Another specific object is to provide such a monitoring system which generates a substantially continuous record of pulsatile blood pressure activity and associated numeric measurement parameters.

Another specific object is to provide such a system in which its accuracy is substantially unaffected by the skill of the user, and for which minimal retraining is required for persons already experienced in the use of available pressure measurement instruments and techniques.

Another specific object is to provide such a system which deflates a blood pressure cuff, through one or more controlled substantially linear rates.

Another specific object is to provide such a system which compensates the systolic and diastolic measurements for the affects of hemodynamic variability thereby producing measurement values that are consistent with those produced by invasive monitoring systems.

Another specific object is to provide such a system which is entirely self-contained.

Another specific object is to provide such a system which automatically adjusts for a multitude of different, typically non-linear factors such as variations in arterial elasticity and the types and relative amounts of intervening tissue existent between a patient's artery and a non-occluding pressure sensing cuff.

Another specific object is to provide such a system, which to ensure accurate consistent measurements, automatically determines whenever, during a period of continuous monitoring, it requires re-calibration and then effectuates any such re-calibration(s).

Another object is to provide a calibration process which can be used as a basis for calibrated measurement of pulsatile arterial activity, such as, for example, systolic, diastolic, and mean blood pressure parameters using many known arterial measurement systems, for durations in excess of a few seconds, and which are typified by non-invasive electrical impedance and strain gauge plethysmography or invasive perivascular sensing methods (which detect blood flow, volume, or velocity as a function of various physiologic parameters that may be taken to be proportional to measured variations in intra-arterial pressure).

Another specific object is to provide such a calibration process that is compatible with other well-known types of sphygmomanometric systems that utilize an occlusive cuff, including those employing microphones and ultrasound flutter principles which detect arterial phenomena as measurement signals during semi-occluded blood flow conditions.

Lastly, another specific object is to provide such a system which utilizes calibration processes of the occlusive cuff to optionally measure discrete systolic and diastolic pressures on an intermittent basis at pre-set time intervals in a similar fashion to other automatic non-invasive pressure measurement products known in the art.

These and other objects are accomplished in accordance with the teachings of this invention by first undertaking a calibration phase (procedure) comprised of: determining the blood pressure occurring in relation to various initial conditions of arterial blood flow and ascertaining the values of a plurality of coefficients, each of which is associated with a corresponding term in a pre-defined function that characterizes blood pressure values in relation to arterial wall displacement; and second, undertaking a continuous monitoring phase comprised of: continually measuring subsequently occurring arterial wall pressure displacement waveform values, ascertaining each subsequently occurring blood pressure value as the pre-defined function of each corresponding measured arterial pressure displacement waveform value, and automatically re-calibrating the system to the patient after the expiration of a pre-defined but adaptively changeable time or in response to the occurrence of any one of a plurality of pre-defined events. This interval, i.e. the time between the occurrences of successive re-calibrations, is adaptively changed in accordance with the results of at least one prior re-calibration and/or whenever significant changes in the trend of arterial wall displacement values occur.

In accordance with the specific embodiment disclosed herein, two separate inflatable cuffs (a relatively high pressure occlusive cuff and a relatively low pressure waveform sensing cuff) are affixed to different locations proximately situated to major arteries of one or two limbs of a patient's body. A computer in conjunction with various pneumatic components effectuates the process of inflation (pressurization) and deflation of each cuff as well as the data acquisition from each. Instantaneous arterial blood pressure is characterized in terms of a parabolic function of arterial wall displacement: namely $f(x) = ax^2 + bx$, where x is proportional to changes in arterial wall displacement measured from a constant reference value, and (a) and (b) are coefficients having values that primarily depend upon various physical characteristics (such as the elasticity of the arterial wall and interspersed biological tissue—existing at the site where blood pressure is being measured, and the cuff material itself) and various blood pressure values determined during the calibration phase through use of the occlusive cuff.

Operation of the blood pressure measurement system occurs, via essentially a two-phase approach. During the first, or "calibration", phase, the computer automatically inflates (pressurizes) the occlusive cuff to a pre-defined suprasytolic value, typically on the order of 150 mm(Hg), and also inflates the waveform sensing cuff to a relatively low pressure of approximately 40 mm(Hg). During this time, the computer automatically checks the integrity of both cuffs to determine whether any significant pneumatic leakage exists anywhere in the system and confirms that both cuffs are properly affixed to the patient. Once both cuffs have been inflated, the computer causes the pneumatic components to bleed down the pressure in the occlusive cuff at a controlled rate while maintaining the pressure of the waveform sensing cuff constant at a value of approximately 40 mm(Hg). During this controlled bleed-down, arterial pressure displacement waveform information is sensed through instantaneous pressure variations (perturbations) occurring in both the occlusive and the waveform sensing cuffs.

The resulting displacement waveform information from both cuffs is digitized and resulting sample values are stored by the computer. These samples are then processed, via several different techniques, to determine systolic and diastolic occlusive cuff pressures, as well as the values of the coefficients (a) and (b).

The particular methods for determining systolic and diastolic occlusive cuff pressure values adjust for heartbeat to heart-beat variability, random bleed rate errors, and patient movement artifacts. Specifically, both the systolic and diastolic pressure determinations are dependent upon analysis and weighted calculations of two groups of at least four pressure displacement waveforms which generally occur when the occlusive cuff pressure is at or near true systolic pressure, first, and then true diastolic pressure, second, during bleed-down. Simultaneously therewith, measurements of the same two groups of pressure waveforms are made using the constant low pressure waveform sensor cuff. Simultaneously with or shortly after—in the event both cuffs are positioned on one limb rather than on opposite limbs) the determination of systolic and diastolic pressure values through occlusive cuff measurements, peak and trough values, associated with the sequence of waveforms measured from the waveform sensor cuff, and averages (denoted as base level values) of these peak and trough values are computed. Shortly thereafter, the occlusive cuff pressure is exhausted to ambient (i.e. atmospheric), and the peak and trough values, the corresponding base level values as well as the corresponding systolic and diastolic occlusive pressure values are all used to determine coefficient values (a) and (b) contained in the arterial wall displacement/pressure function. After these coefficients are determined, the computer uses the displacement/pressure function to calculate a set of values for subsequent storage in a look-up table. This table consists of the blood pressure values that correspond to a relatively large number of uniformly-spaced arterial wall displacement values which span an entire pre-defined numeric range.

The second or "continuous" monitoring phase, based on the newly calculated look-up table, commences immediately upon conclusion of the calibration phase. During this second phase, data in the look-up table is used to convert actual arterial pressure displacement waveform sample values into blood pressure waveforms for both display and subsequent calculation of various numeric measurement parameters. Specifically, individual displacement waveforms obtained through the low pressure waveform sensor cuff are continuously sampled and digitized at a relatively fast rate. The value of each sequentially measured instantaneous sample is then used by the computer to access the look-up table to determine a corresponding instantaneous value of calibrated blood pressure. Since an artifact in the arterial blood flow can induce errors in blood pressure measurements, each calibrated blood pressure value is tested, by determining whether its value lies outside of a pre-defined range, in order to identify those values which might have been affected by artifacts and are those of questionable accuracy. The non-affected values are then used in the computation of various displayed numeric measurement parameters. Simultaneously with this latter step, each calibrated pressure value is graphically displayed, along with a sequence of immediately prior pressure values, on an amplitude (pressure) vs. time basis. Any pressure values identified as being affected by artifacts are specifically labelled in the display, by, for example, being replaced with an appropriately labeled horizontal bar.

All the sequentially produced calibrated blood pressure values are displayed at a sufficiently rapid rate such that the resulting display appears as a continuous trace and accurately represents a patient's continuous arterial blood pressure waveform activity, in essentially the same form as obtained using well-known invasive monitoring techniques. Specifically, the most recently detected and calibrated pressure waveforms first appear at the beginning of the trace display area, scroll across and then disappear as time passes, while simultaneously new waveforms continue to appear at the beginning, all in their actual sequence of occurrence. In addition, displayed measurements of various numerical parameters include: systolic, diastolic, mean and pulse pressures (typically, averages of individual values from 4–6 waveforms); variability indices of waveform-to-waveform systolic or pulse pressures and/or maximum rate of systolic pressure ascent (sometimes termed the endocardio-viability ratio); and various heart rhythm measures. Furthermore, many of these numerical measurement parameters are checked against pre-defined minimum and maximum alarm limit values and, when any of these limits is exceeded, appropriate warning notifications are transmitted visually and/or aurally to an operator. In addition, historical arterial blood pressure data, trends, and alarm activity are summarized and/or retained for subsequent statistical processing and patient hard copy document records.

Since the waveform sensing cuff is only inflated to a relatively low pressure, it can be advantageously worn quite comfortably by any patient for an extended period of time. Pressurized air (or another pressurized fluid) existing within this cuff is the medium through which arterial displacement activity is transmitted to a pressure transducer. This medium enables the externally applied pressure to be readily controlled such that it remains essentially constant over time, thereby advantageously assuring that the pressure displacement waveform samples are properly referenced to a known "base level" reference pressure. Through on-going repetitive sensing of this reference pressure, i.e. the actual reference pressure existing within the waveform sensing cuff, differences in this pressure from the base level reference pressure that are larger than a pre-determined differential limit can be readily adjusted by appropriate cuff inflation or deflation to ensure that the actual reference pressure remains substantially equal to the desired base level reference pressure. This effectively prevents erroneous pressure measurements that would otherwise occur from time-to-time due to gradual and relatively long lasting patient movements, slow leaks in the waveform sensing cuff and other similar circumstances. Specially, the reference pressure might increase as the result of a sustained externally-induced and gradually-applied compressive force applied to the waveform sensing cuff which might result from patient movement or inadvertent repositioning of this cuff to a larger circumferential part of the limb to which it is attached. This reference pressure increase would erroneously augment the displacement sample values detected from the waveform sensing cuff in the absence of corrective deflation of the cuff. Conversely, when the cuff has been inadvertently repositioned to a smaller segment of the limb or is experiencing substantial pressure leakage, the reference pressure would decrease and, in turn, erroneously understate the magnitude of the detected displacement sample values in the absence of corrective inflation of the cuff.

Furthermore, the average rate of change in reference pressure is also monitored during the "continuous monitoring" phase in order to assure consistent pneumatic system operation and hence accurate displacement measurement. Specifically, after each corrective cuff inflation (or deflation) occurs, the rate at which the actual reference pressure varies is determined. Whenever the absolute value of this difference exceeds a predefined limit, this manifests an error condition typified by a significant air leak in the pneumatic system, temperature gradients in the pressurized air used therein or the like. To eliminate this condition, a re-calibration is automatically initiated. If, however, these error conditions continue to occur despite re-calibration, then the computer displays an appropriate error message, exhausts both cuffs and shuts the entire system down.

At various predefined but adaptively changing time intervals the computer automatically initiates another calibration phase. During any such "re-calibration", new values are determined for coefficients (a) and (b). Each new coefficient value is then compared with its respective prior value to determine the amount of difference existing therebetween. Based upon the magnitude of this difference, the computer adaptively determines the duration of the time interval for the next continuous monitoring phase (i.e., before the next successive re-calibration occurs). In addition, re-calibrations are automatically initiated whenever significant rates of change, as previously described, are detected in the reference pressure of the waveform sensor cuff or whenever significant cumulative changes occur in continuously monitored blood pressure such as, for instance, when the systolic, diastolic and/or any other calculated cardiovascular numeric parameters varies by more than a pre-defined amount (typically 7 percent) from the corresponding values determined during the prior calibration phase.

BRIEF DESCRIPTION OF THE DRAWING

The invention may be clearly understood from a consideration of the following detailed description and accompanying drawing, in which:

FIG. 4 depicts a block diagram of Signal Conditioner 147 shown in FIG. 1B;

FIGS. 7A and 7B depict a flowchart of the overall calibration and continuous monitoring operations of the non-invasive blood pressure measurement system shown in FIGS. 1A and 1B;

FIG. 8 depicts a flowchart of Cuff Operations Routine 620 referred to in FIG. 7A;

FIG. 9 depicts a flowchart of Cuff Integrity Verification Routine 737 shown in FIG. 8;

FIGS. 12A-12G together depict a detailed flowchart of Systolic Determination Routine 1020 referred to in FIG. 11;

FIGS. 15A-15D graphically depict four hemodynamic sequences of intra-arterial pressure waveforms with each dashed line representing a different bleed-down sequence for occlusive cuff 20;

FIGS. 16A-16H graphically depict, on a pressure v. time basis, the resulting measurements taken through occlusive cuff 20 of each particular pressure waveform amplitude sequence that corresponds to each dashed line bleed-down sequence depicted in FIGS. 15A-15D;

FIGS. 17A-17H are vector diagrams illustrating the determination of systolic pressure for each case shown in FIGS. 15A-15D and in FIGS. 16A-16H, respectively;

FIGS. 18A and 18B are flowcharts of Mean Profile Routine 1033 referred to in FIG. 11;

FIGS. 20A and 20B are flowcharts of Sliding Slope Routine 1037 referred to in FIG. 11;

FIGS. 21A-21F graphically depict six different illustrative sequences of pressure waveform peaks and show the determination of the diastolic pressure (DP) for each sequence by Sliding Slope Routine 1037.

To facilitate easy understanding, identical reference letters and/or numerals are used to denote identical elements common to the figures.

DETAILED DESCRIPTION

Although the teachings of the present invention are applicable to continuous non-invasive pressure measurement of any relatively non-compressible fluid, for purposes of the following description, the present invention will be described in terms of a continuous non-invasive blood pressure measurement system. In this respect, all pressure values recited hereinafter are in millimeters of mercury, i.e. mm(Hg).

1.0 Hardware Considerations

Figure 1A:
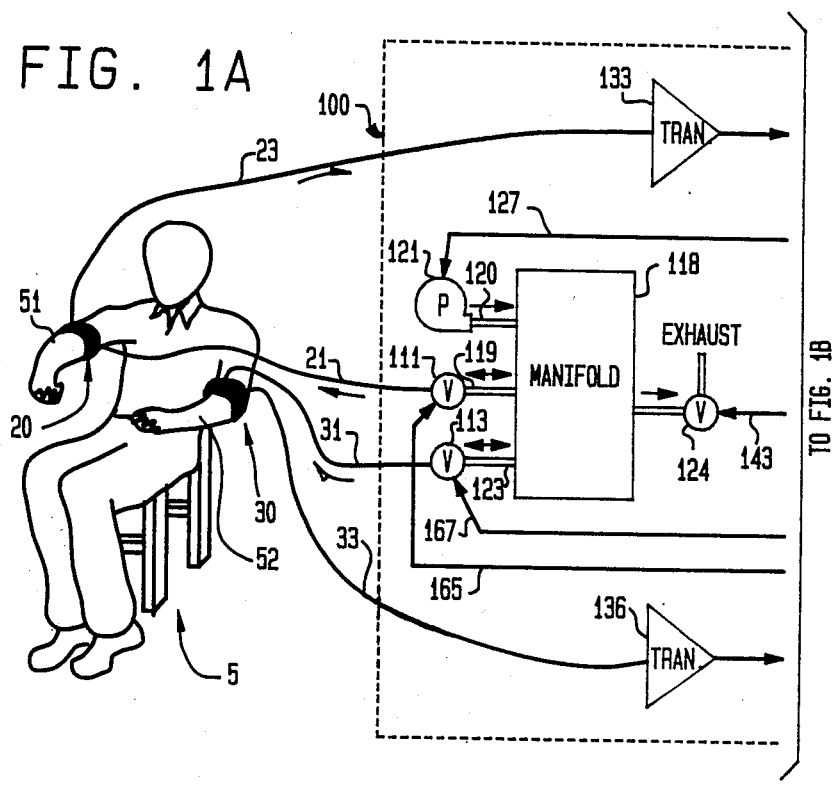
FIGS. 1A and 1B together depict a block diagram of a non-invasive blood pressure measurement system embodying the teachings of the present invention and the manner in which it is attached to a human patient.
Figure 1B:
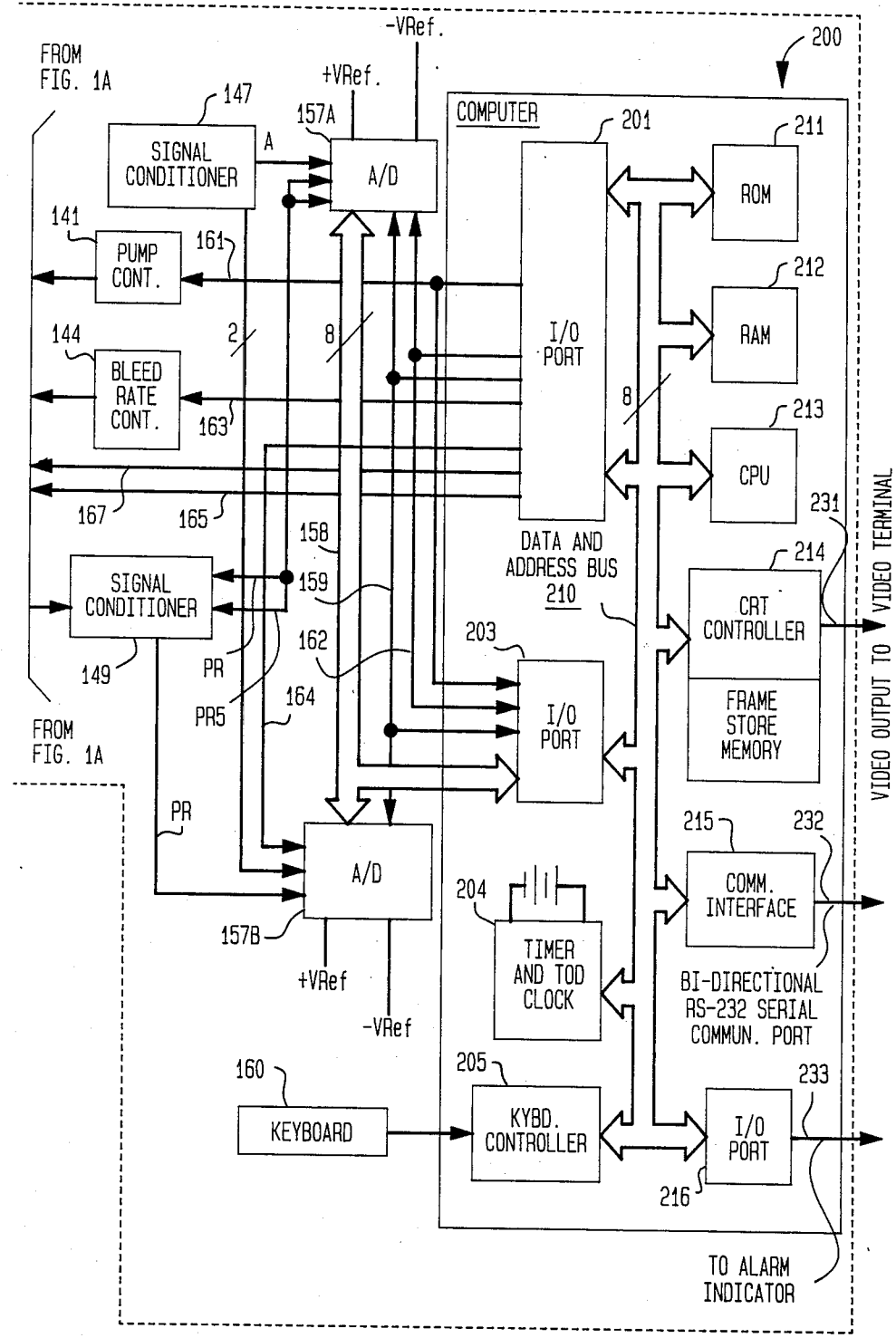

A non-invasive blood pressure measurement system (hereinafter referred to as "the system") embodying the teachings of the present invention is shown in block diagram form in FIGS. 1A and 1B. These figures also show the manner in which the system is typically attached to a human patient.

As shown, the system is essentially comprised of control and measurement unit 100 and two inflatable cuffs: occlusive (high pressure) cuff 20 and waveform sensing (low pressure) cuff 30. These cuffs are preferably secured around opposite limbs of patient 5 and are automatically inflated and deflated, i.e. bled-down, by control and measurement unit 100 which also, in a manner to be fully described below, senses arterial wall displacement and calculates the instantaneous blood pressure values corresponding thereto.

Both cuffs are connected by respective pneumatic lines (tubing) to control and measurement unit 100. Lines 21 and 31 are respective inlet lines to occlusive cuff 20 and waveform sensing cuff 30, and pneumatic lines 23 and 33 are respective outlet lines from these same cuffs. FIG. 1a shows the preferred manner in which these cuffs are secured to the patient, i.e. with occlusive cuff 20 attached around upper arm 51 and waveform sensing cuff 30 attached around upper arm 52, such that the center of the air bladder of each cuff is proximately situated to the major (brachial) artery in each arm. A variety of alternate patient attachment schemes are also possible with the system. For example, since at least two preferred sites exist on each limb, e.g. the upper arm and wrist of the same arm or the thigh and ankle of the same leg, the two cuffs may be positioned on any one or two of a patient's four limbs. As will be apparent from the discussion below, the system is capable of accurately performing continuous monitoring even if occlusive cuff 20 is positioned at the upper location (on an arm or thigh) and waveform sensing cuff 30 is positioned at the more distal location (wrist or ankle) of the same limb. Generally, the embodied teachings of the present invention apply to all these alternate schemes, but in the latter situation where both cuffs are attached to the same limb, continuous monitoring must be interrupted for pre-determined, illustratively half-minute, intervals during which re-calibration occurs. This interruption is necessary since an inflated occlusive cuff distorts (occludes) the pulsatile arterial blood flow that would otherwise be detected by the waveform sensing cuff if it were located on another limb.

Within control and measurement unit 100, computer 200 controls the inflation and deflation of both cuffs, as well as the data acquisition from within each. Computer 200 is illustratively comprised of any one of several well-known processors and is advantageously implemented using any one of many commercially available microprocessors along with necessary and ancillary support circuitry. Since the architecture of the computer system is immaterial for purposes of the present invention, this architecture, for purposes of clarity, is illustratively shown as having only a single data and address bus 210. This bus inter-connects various input-output (I/O) ports, namely ports 201, 203 and 216; central processing unit (CPU) 213, random access memory (RAM) 212; read only memory (ROM) 211, timer and time-of-day clock 204; and communications circuitry comprised of keyboard controller 205, CRT controller 214, and communication interface 215. ROM 211 stores the program, which as discussed in much greater detail below, controls the operation of the system, and the data processing used therein. RAM 212 stores temporary data. Under control of the CPU and the program stored in ROM 211, the system accepts control information from an operator through, illustratively, keyboard 160 and keyboard controller 205, and provides output information compatible for display on a video terminal, through CRT controller 214, or in a form illustratively RS-232 compatible, via port 232, for connection to other digital devices, such as a hardcopy recorder, another monitor, or a centralized computer system. CRT controller 214 illustratively includes a frame-store memory for use in producing graphics, including historical blood pressure trend data, for subsequent display on video monitor. Input information, including data and commands, can also be applied to the computer in serial form via bi-directional port 232 and communication interface 215. Lastly, timer and time-of-day clock 204, which is connected to bus 210, provides a timing function, as well as a real-time clock for use by computer 200 in accordance with the program stored in ROM 211.

Computer 200 also provides, through the I/O ports, appropriate electrical signals to control the operation of the pneumatic elements contained within the system, as well as to control the sampling of data from both cuffs. Through I/O port 203, CPU 213 obtains pressure data in digital form from analog/digital converters 157A and 157B. The CPU, through I/O port 216, drives various alarms and other indicators to display the current status of the system. I/O port 201 provides appropriate electrical signals on leads 161, 163, 165, and 167 to pump control 141, bleed rate control 144, and electrically-operated pneumatic valves 111 and 113, respectively, to control the inflation and deflation of both cuffs.

To inflate either cuff, computer 200 first applies appropriate voltage levels, via I/O port 201 and leads 165 and 167, to activate pneumatic valves 111 and/or 113 such that the desired cuff(s) is pneumatically connected through pneumatic lines 119 and/or 123 to manifold 118. Manifold 118 serves as a reservoir for the compressed air generated by air pump 121 and as an interconnection point for the different pneumatic components used in the system. Once the appropriate valve(s) has been activated, computer 200 then, via I/O port 201, applies an appropriate voltage, via lead 161, to cause pump control 141 to activate air pump 121. Specifically, pump control 141 converts the digital level on lead 161 into an appropriately-scaled and buffered analog voltage which is then applied, via lead 127, to air pump 121. This pump applies compressed air, at a pressure determined by the magnitude of the voltage appearing on lead 127, through pneumatic line 120 to manifold 118 and, in turn, through the activated valve(s) 111 and/or 113, to tne selected cuff(s). Valve 111, when activated, routes all or a portion of this air via pneumatic line 21 to occlusive cuff 20, and valve 113, when activated, alternatively routes all or a portion of this air via pneumatic lines 31 to low pressure waveform sensing cuff 30. Clearly, many other configurations of pneumatic components, which together perform the same function as that described above, can be readily substituted for the configuration shown in FIGS. 1A and 1B.

To sense the air pressure contained in either one or both of the cuffs, computer 200 first selects the appropriate input signal to be converted by each A/D converter, i.e. converters 157A and 157B. Specifically, each A/D converter receives an analog signal which is first produced by the pressure transducer connected to each cuff and subsequently conditioned by an appropriate signal conditioner. Computer 200, by applying appropriate select signals, via I/O port 201, and leads 162 and 164 causes each of the A/D converters 157A and 157B, respectively, to select the desired input signals for subsequent conversion. For example, either of A/D converters 157A and 157B can select the analog signals associated with either occlusive cuff 20 or waveform sensing cuff 30. Alternatively, if these converters contain appropriate bus-compatible addressing circuitry, then the selection signals are applied over the bus as addresses thereby eliminating the need for separate selection lines, such as 162 and 164. With either arrangement, the performance of each A/D converter can advantageously be checked, particularly for purposes of calibration, by switching (reversing) the pressure transducer output signals which are converted by each A/D converter and/or by selecting a fixed reference voltage ($+V_{REF}$ or $-V_{REF}$) for conversion by either or both A/D converters.

The output of pressure transducers 133 and 136, associated with occlusive cuff 20 and waveform sensing cuff 30 respectively, is amplified, scaled and appropriately filtered by signal conditioners 147 and 149. The circuitry of each conditioner is identical, and that of illustratively conditioner 147 is shown in block diagram form in FIG. 4. Each conditioner produces three separate output signals Pw, Prs, and Pr. As shown, conditioner 147 imparts a pre-determined low-pass characteristic to the output of its associated pressure transducer to filter out high frequency noise and other preturbations from the desired low-frequency data. In particular, pressure displacement waveform analog signal Pw is produced by routing the output of transducer 133 first through high pass filter (HPF) 147a and then through low pass filter (LPF) 147b, which have 3 dB attenuation value cut off frequencies of about 0.2 and 20 Hertz, respectively. Additionally, analog signal Prs, which consists of a slowly varying respiratory-induced pressure displacement component Pr plus a steady-state cuff pressure value, is produced by routing the output of transducer 133 through LPF 147c which has a 3 dB attenuation value cut-off frequency of about 0.4 Hertz. Capacitive coupler 147d extracts the analog signal component Pr from signal Prs. In the preferred embodiment shown, both analog signal outputs Prs and Pr are connected to A/D converter 157B, and analog signal output Pw is connected to A/D converter 157A.

Once the appropriate input signal has been selected for each A/D converter, computer 200 (See FIG. 1B) then applies a "START CONVERSION" signal, via lead 159, to each A/D converter, to initiate conversion of its selected input signal. After a short pre-defined period of time has elapsed, i.e. sufficiently long for the converter to convert the data into digital form and to allow the data to stabilize on bus 158, I/O port 203 transfers the digital data into the computer for further processing.

The deflation (bleed-down) of either cuff requires that the desired cuff be selected and a pneumatic air channel be established between it and bleed valve 124. To set the rate at which air is bled from the selected cuff, computer 200 first applies an appropriate level to electrically-operated pneumatic valves 111 or 113, via leads 165 or 167, respectively, to select the appropriate cuff and route the compressed air contained therein to manifold 118, via pneumatic lines 119 or 123, respectively. Thereafter, computer 200, via I/O port 201 and leads 163, provides appropriate signals to bleed rate control circuit 144 which specifies the rate at which air is bled (the "bleed-rate") from the selected cuff and exhausted to the atmosphere via bleed valve 124.

Figure 5A:
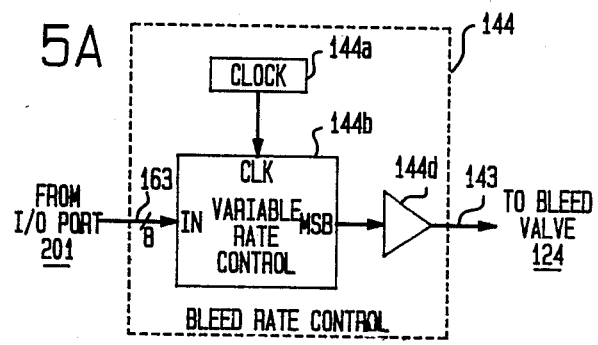
FIGS. 5A and 5B together depict block diagrams of alternative embodiments of Bleed Rate Control 144 shown in FIG. 1B.

A block diagram of one embodiment of bleed rate control 144 is shown in FIG. 5A. As shown, an incoming 8-bit word, from I/O port 201, which specifies the bleed rate, is loaded into variable rate counter 144b in response to a load pulse (not shown). Thereafter, clock 144a applies a train of clock pulses, to the clock input of this counter to repetitively increment its contents by one. The most significant bit (MSB) is applied through buffer 144d, to drive bleed valve 124. As long as the value of the MSB is one, buffer 144d produces a high output level (e.g. a "1") to open the bleed valve. Alternatively, whenever the value of the MSB is zero, buffer 144d produces a low (e.g. a "0") level signal to close the bleed valve. As soon as the count "rolls over" from its maximum count to zero, the bleed rate value is re-loaded into the counter and incrementation begins again. Counter 144b is advantageously fabricated as a latched counter in which the bleed rate value is written into an input latch and a carry out pulse from the counter is used to load the contents of the latch into the counter at the occurrence of every "roll over". Hence, the magnitude of the bleed rate value linearly specifies the open-time (and duty cycle) of bleed valve 124. Several different 8-bit bleed rate values are stored as constants within computer 200 so as to define a number of different linear rates for use in conjunction with different phases of occlusive cuff measurement and/or different cuff sizes. A particular one of these constants is selected by the program resident within ROM 211 and applied via I/O port 201 and leads 163 to bleed rate control 144.

Figure 5B:
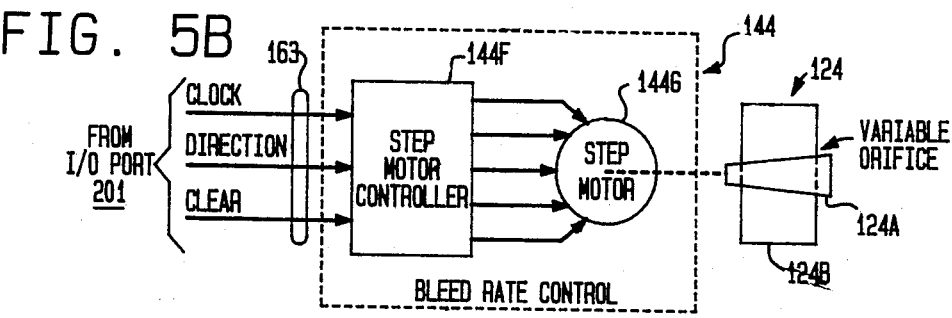

An alternate embodiment for bleed rate control 144 is shown in FIG. 5B. In this embodiment, computer 200 provides various control signals, via I/O port 201 and leads 163, to step motor controller 144f which, in turn, controls the incremental movement of the armature of step motor 144g. This armature is mechanically connected, through illustratively a well-known rack and pinion assembly or the like (not shown), to needle 124a to vary its longitudinal position within valve body 124b, thereby determining the orifice size of the valve. In operation, computer 200, via leads 163, applies a signal of appropriate level to the direction input of step motor controller 144f in order to set the direction in which the armature of step motor 144g is to turn, i.e., to push the needle into the valve body, thereby closing the valve, or to pull the needle from the valve body thereby opening the valve. Thereafter, computer 200 applies a series of clock pulses to the clock input of step motor controller 144f to incrementally move the needle in order to linearly open or close the valve by a desired amount. This, in turn, sets the bleed-rate accordingly. The rate of these clock pulses is governed by the desired rate of change in the bleed rate. Whenever an appropriate signal is applied to the clear input by computer 200, either during system operation or during "power-up", step motor controller 144f causes step motor 144g to move to a pre-selected initial position, i.e. to fully open the valve for safety purposes.

Figure 6:
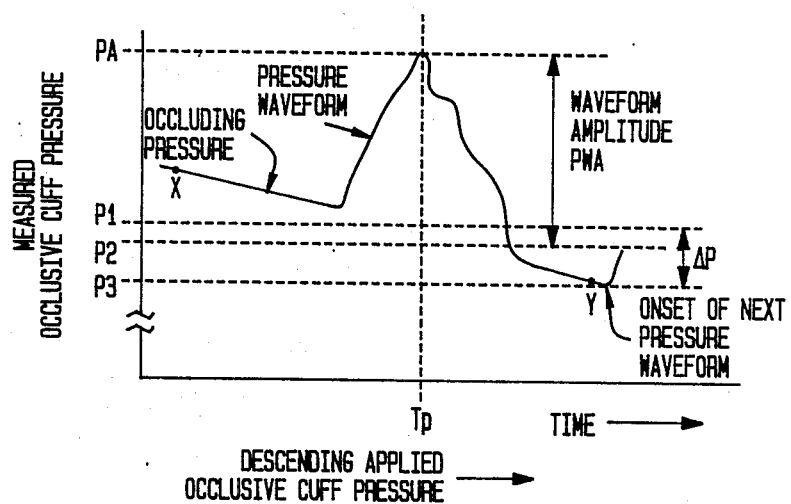
FIG. 6 depicts a sketch of a typical pressure waveform detected during bleed-down of occlusive cuff 20 shown in FIG. 1A.

The occlusive cuff, in a manner to be described in detail shortly, is only used during a relatively brief and infrequent "calibration" phase to obtain systolic and diastolic blood pressure values of the patient. Both these values are obtained during bleed down of this cuff from the "supra-systolic" pressure. At a point while the air pressure in this cuff is bled down from this initial maximum pressure, pulsatile arterial blood begins to flow through the then partially occluded artery, thus, imparting a train of pressure displacement waveforms to the linearly decreasing pressure of the air contained within the occlusive cuff. A typical pressure waveform produced by one heart-beat is depicted in FIG. 6. As shown, the air pressure in the occlusive cuff is being bled-down along a line generally resembling line X-Y. At illustratively pressure $P_1$, the arterial wall begins to distend, i.e. move radially outward, in response to the onset of a pulse of blood flowing through the artery. As the artery continues to distend outwardly, it exerts pressure onto the occlusive cuff and produces a pressure displacement waveform having amplitude values PWA (equaling $P_A$ minus $P_2$) at time $T_P$. The next pressure waveform illustratively begins at occlusive cuff pressure $P_3$, which is a lower applied cuff pressure than that occurring at the onset of the previous pressure pulse by the amount of air bled-down from the occlusive cuff during this heart beat. A typical complete series of these pressure waveforms occurring during a complete measurement cycle, i.e. controlled deflation from supra-systolic to less than diastolic, is illustratively shown in FIG. 19B.

Occlusive cuff 20 is not described in detail since it is preferably a standard "Velcro" wrap-around occlusive blood pressure cuff well known to those skilled in the art of sphygmomanometer based blood pressure measurement.

Figure 2:
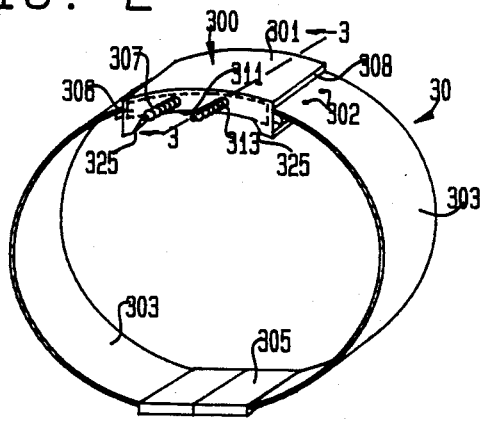
FIG. 2 depicts a sketch of Waveform Sensing Cuff 30 shown in FIG. 1A.
Figure 3:
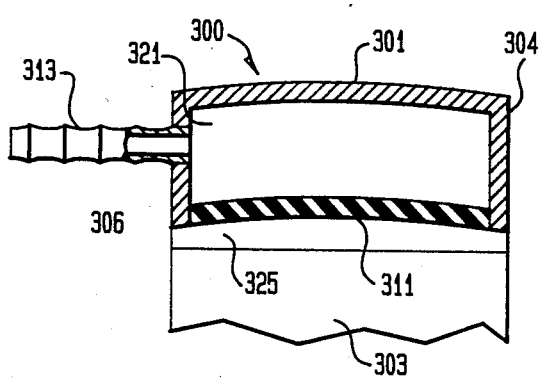
FIG. 3 depicts a cross-sectional view of Waveform Sensing Cuff 30 taken along lines 3—3 shown in FIG. 2.

FIG. 2 shows a side perspective view of (low-pressure) waveform sensing cuff 30, and FIG. 3 shows a cross-sectional view taken through lines 3—3 shown in FIG. 2. This cuff is comprised of chamber 300 having five rigid surfaces (of which only top surface 301, and side surfaces 304, 306 and 308 are shown) and a compliant bottom surface 311. All the rigid side surfaces are illustratively metallic or hard plastic with the bottom surface being either soft plastic or rubber. Nipples 307 and 313 pneumatically connect air 321 contained within the chamber to pneumatic lines 31 and 33, respectively. To secure this cuff around a patient's arm (as shown in FIG. 1A), the chamber is illustratively secured to a bracelet or strap having arms 303 which are each connected to respective sides of clasp 305. Each arm is attached illustratively by rivets, such as rivets 302, to a respective side surface of chamber 300, such as surface 308. Ridges 325, located at opposite ends of the bottom of chamber 300 serve to advantageously minimize the effect of any downwardly directed external forces inadvertently applied to top surface 301 from interfering with the movement of compliant member 311 caused by pulsatile pressure displacement activity of an underlying major artery. These forces can occur through inadvertent contact with an object or clothing.

In operation, the waveform sensing cuff is first attached around a patient's arm. Thereafter and upon receipt of an appropriate instruction from the operator, computer 200 causes the air pump to inflate the waveform sensing cuff to approximately 40 mm and to thereafter maintain this pressure. The radial movements (displacements) of the wall of the artery attributable to a heart contraction-induced intra-arterial blood pressure pulse (herein termed a "pressure waveform") are transferred through the patient's skin to the bottom surface of the waveform sensing cuff. These arterial wall displacements, in turn, compress air 321 contained within the cuff, and thus in turn modulates the cuff pressure in direct proportion to the magnitude of the arterial wall displacement. A complete cycle of these variations which resembles a pulse and occurs at each heart-beat, results in what is hereinafter referred to as a "pressure displacement waveform". During the "continuous monitoring" phase, only the (low pressure) waveform sensing cuff is used to acquire these waveforms; the (high pressure) occlusive cuff remains completely deflated during this time. Because the waveform sensing cuff is inflated to and maintained at a considerably lower pressure than that needed to cause any occlusion to the artery, the waveform sensing cuff advantageously can be worn continuously by the patient for prolonged periods of time without causing physiologic damage or any noticeable discomfort to the patient.

2.0 Software Considerations

Up to this point the discussion has centered on the specific hardware of the inventive blood pressure measurement system. With reference to FIGS. 7-22, the remaining discussion will now describe the software used to control the operation of the system and, specifically, the data aquisition, analysis and measurement processes associated therewith.

2.1 Overview—Calibration and Continuous Monitoring

A flow chart of the overall operation of the inventive system is depicted in FIGS. 7A-B. Whenever the operator depresses a "start" key (not shown) on keyboard 160 (see FIG. 1B), computer 200 automatically initializes itself by executing initialization routine 610. This routine loads various default values from ROM memory into RAM memory and automatically executes various diagnostics to confirm that the entire system is operating properly. Thereafter, as shown, system operation is divided into two distinct phases: the "calibration" phase and the "continuous monitoring" phase.

The "calibration" phase is comprised of cuff operations routine 620, waveform sensor initialization and occlusive cuff measurements routine 630, and moduli look-up determination routine 640. Upon entering the "calibration" phase from the initialization routine, computer 200 first executes cuff operations routine 620. During this routine, the system automatically inflates both the occlusive and waveform sensing cuffs to predefined pressures that are determined by this routine. Concurrently therewith, the computer checks the integrity of both cuffs for leaks or improper installation on the patient. In the event, any leaks are discovered or if the system determines that either cuff has been improperly installed, both cuffs are immediately vented to the atmosphere and an appropriate user notification message is displayed, all as discussed in more detail later in conjunction with the cuff integrity verification routine shown in FIG. 9. Alternatively, if no leaks are detected and both cuffs are determined to be properly secured to the patient, then waveform sensor initialization and occlusive cuff measurements routine 630 is executed.

Waveform sensor initialization and occlusive cuff measurements routine 630 determines the base-level reference pressure of the waveform sensing cuff—thereby providing a proper reference for subsequent continuous monitoring, diastolic and systolic pressures from bleed down of the occlusive cuff and certain base-level peak and trough values associated with several pressure displacement waveforms that occur during occlusive cuff bleed down. After the base-level pressure has been determined, routine 630 causes the pneumatic system to bleed air down from the occlusive cuff. Simultaneously therewith, this routine determines the systolic and diastolic occlusive cuff pressure values of the patient through processing pressure displacement waveforms that have been detected through perturbations in the air pressure of the occlusive cuff while it is being bled-down. Once the diastolic and systolic pressure values have been ascertained, then the remaining cuff pressure is abruptly reduced to atmospheric and control proceeds to moduli table determination routine 640.

Routine 640 uses both the systolic and diastolic occlusive cuff pressure values and base-level peak and trough displacement values, all determined in routine 630, as boundary conditions and values of the independent variable x, respectively, to determine, through solving a set of simultaneous equations, the values of various coefficients, specifically coefficients (a) and (b), which appear in a pre-defined relationship, illustratively parabolic and of the form $f(x)=ax^2+bx$. This relationship characterizes any instantaneous blood pressure value $f(x)$ in terms of any pressure displacement sample value x. Once these coefficients are calculated, computer 200 fabricates a look-up table of calculated blood pressure values for a pre-selected series of close and uniformly-spaced arterial pressure displacement values which span the entire range of displacement values that can be expected to occur during continuous monitoring. This range extends above and below the base-level peak and trough values, respectively, by an amount equal to approximately 25% of each respective value. Once both of these coefficients have been determined, each pre-selected displacement value is successively substituted into the pre-defined relationship in order to compute each corresponding instantaneous blood pressure value. The resulting table is stored in RAM memory 212 (see FIG. 1B) existing within computer 200 for use during the second, i.e. "continuous monitoring", phase of system operation.

Once the look-up table has been completely fabricated, the "continuous monitoring" phase begins with the execution of waveform sensor monitoring routine 650. This routine determines the continuously occurring instantaneous displacement waveform sample values detected from waveform sensing cuff measurements and ascertains the continuous blood pressure measurements corresponding thereto. Specifically, the magnitude of each displacement value detected through the waveform sensing cuff is used to access the look-up table for a corresponding instantaneous blood pressure value. If the actual displacement value lies between two adjacent pre-defined displacement values in the table, then the two corresponding blood pressure values stored in the table are interpolated, using preferably well-known linear interpolation techniques, to compute the appropriate calibrated blood pressure value corresponding to the actual displacement value. Thereafter, computer 200 routes each calibrated instantaneous blood pressure value in sequence along with previously determined calibrated blood pressure values, via port 231 (see FIG. 1B) to a video terminal for display a continuous trace and/or via port 232 as serial digital information to another digital device. These continuous pressure values are applied to these ports at a rate of approximately 50 or more values per second such that the displayed result is a continuous trace. To provide a trace similar to the waveform display of an invasive monitor, enough prior values to encompass the last 4–8 seconds of arterial activity are sent to these ports and displayed.

After a pre-defined time interval of continuous monitoring has elapsed, or other events occur such as significant changes in reference pressure or blood pressure parameter levels both of which are recognized by decision routine 660, the system automatically re-enters the "calibration" phase to re-calibrate its measurements. During any such "re-calibration", new values are determined for coefficients (a) and (b) as well as for diastolic, systolic, base-level reference and base-level peak and trough values. Each new coefficient value is then compared with its respective prior value—determined during execution of the most recent calibration phase. The amount of difference existing between corresponding coefficient values is used to determine the duration of the time interval of the next successive continuous monitoring phase. Specifically, if this difference is within an acceptable limit, typically on the order of a few percent of the previous coefficient value, the duration of next continuous monitoring phase is set to last approximately twice that of the prior continuous monitoring time interval. Conversely, if the difference is greater than the acceptable limit, the computer sets the duration of the next continuous monitoring interval to approximately half that of the prior interval. The length of the interval between successive "re-calibrations" continues to adaptively change until either a minimum pre-defined interval, on the order of a few minutes, or a maximum pre-defined interval, on the order of approximately 30 minutes to an hour or more, is reached between successive "re-calibrations". Moreover, the value of this interval is unaffected by the other aforementioned events, such as significant changes in blood pressure measurement levels, which by themselves serve to initiate a re-calibration at an earlier time during the continuous monitoring phase, i.e. prior to the planned end of the current interval, than would otherwise be the case.

If, however, decision block 660 determines that a "re-calibration" is not to occur, then the system remains in the "continuous monitoring" phase and waveform sensor monitoring routine 650 is merely re-executed.

2.2 Cuff Operations Routine 620

A flowchart of cuff operations routine 620, which forms part of FIG. 7A, is depicted in FIG. 8. Execution of this routine begins with a determination by decision block 705 as to whether prior continuous monitoring has occurred for the present patient. If no such monitoring has occurred, i.e. this is the first pass through the inflation routine for the present patient, then execution proceeds down the "No" path from decision block 705 to decision block 710. This latter decision block selects an appropriate tentative target occluding pressure value for the occlusive cuff, either about 10 mm(Hg) in excess of the upper systolic pressure alarm alert value—if any—set by the operator (value TP2) or a pre-defined default value stored in ROM which is approximately 140 mm(Hg)—(value TP1). User accessible panel switches (not shown) are the means by which the alarm alert values are set by the operator. Execution block 730 selects the target occluding pressure to be the larger of the tentative target pressures of blocks 720(TP1) and 725(TP2). Alternatively, if prior continuous monitoring had already occurred, then execution proceeds down the "Yes" path from decision block 705 to execution block 715 which sets the "target" pressure to be a value equal to approximately 20 mm(Hg) higher than the average of a pre-determined number of prior systolic pressure values determined during the most recent monitoring phase. Once the target pressure has been set to the appropriate value by execution of blocks 715 or 730, then control passes to block 735 which initiates the inflation of the occlusive and waveform sensing cuffs. Execution of block 735 opens valves 111 and 113 and activates air pump 121.

Periodically during cuff inflation, computer 200 executes cuff integrity verification routine 737 to determine whether any air leaks occur and/or whether both cuffs are properly secured to the patient. This routine is shown in flowchart form in FIG. 9. Upon entry into this routine, computer 200 first executes block 905 to determine the actual pumping rate, $\Delta p$, associated with each cuff at various pre-defined times occurring early in the pressurization (i.e. before the pressure in each cuff reaches 40 mm(Hg)). This rate is illustratively determined by ascertaining the differential cuff pressure between the beginning and end of a pre-defined elapsed interval of time and dividing the latter into the former. Once an actual pressurization rate is determined, a previously-determined look-up table is accessed through the execution of block 910. This table consists of minimum and maximum acceptable pressurization rates $\Delta P$ for the waveform sensor cuff and for each different permissible occlusive cuff size. If the value of the actual rate $\Delta P$ lies between a pair of stored minimum and maximum values of $\Delta P$, then the computer, through block 910, characterizes that channel in terms of the corresponding type and size of cuff connected thereto, e.g. occlusive cuff channel or waveform sensor cuff channel, and designates each channel as such and checks to see that both channel designations are consistent with those produced during the most recent re-calibration phase. If so, then execution proceeds, via the "yes" path, out of cuff channel verification routine 737 to path 739 (in cuff operations routine 620—see FIG. 8) wherein control is effectively split in order to essentially execute two relatively slow processes simultaneously and in real-time, i.e. continued inflation of both the occlusive and waveform sensing cuffs. Specifically, control proceeds to both waveform sensing cuff pressurization routine 744a and occlusive cuff inflation routine 744b. Although the sequential nature of the computer only permits it to execute one instruction at a time, the extremely high speed at which execution occurs relative to the system process being controlled (cuff inflation, waveform sampling, etc.) permits several such processes to be evoked and controlled in real-time or an essentially simultaneous basis. For purposes of simplicity, the flowcharts have been drawn, using a symbol typified by that shown for path 739, to show simultaneous control of multiple process rather than to show, from the perspective of the computer, the actual sequential operation as evoked by the program stored in ROM 211 (see FIG. 1B).

However, in the event that channel designation is not consistent between successive re-calibrations, then execution is transferred via the "no" path from block 920, in cuff integrity verification routine 737 (see FIG. 9), to block 925 which terminates the measurement process and evacuates the pressure in both cuffs. Thereafter, computer 200, via blocks 927 and 929, determines the most probable source of the aberrant pressurization rate(s) and the inability to designate the cuff channel(s) and in turn displays an appropriate error message. Specifically, execution block 927 subtracts the actual pressurization rate from the expected pressurization rate (the latter being the mean of the minimum and maximum rate) for the undesignated cuff channel to yield a differential pressurization rate, D. The magnitude of D is used by execution block 929 to access a previously-stored look-up table of fault condition messages that correspond to all possible configurations of undesignated channels and ranges of aberrant values of D. Once a message is selected for a particular situation, it is displayed on the video terminal. For example, if the actual pressurization rate matches that required for the waveform sensor cuff, but the differential pressurization rate of the undesignated channel were too excessive to be matched to that associated with any occlusive cuff then the fault condition message might be "occlusive cuff tubing obstruction." Conversely, for lower-than-expected pressurization rates, "loosely fitted cuff", "detached cuff", "disconnected air line" or "air line leakage" fault conditions can be identified and displayed, depending on the resultant value of D.

Figure 10A:
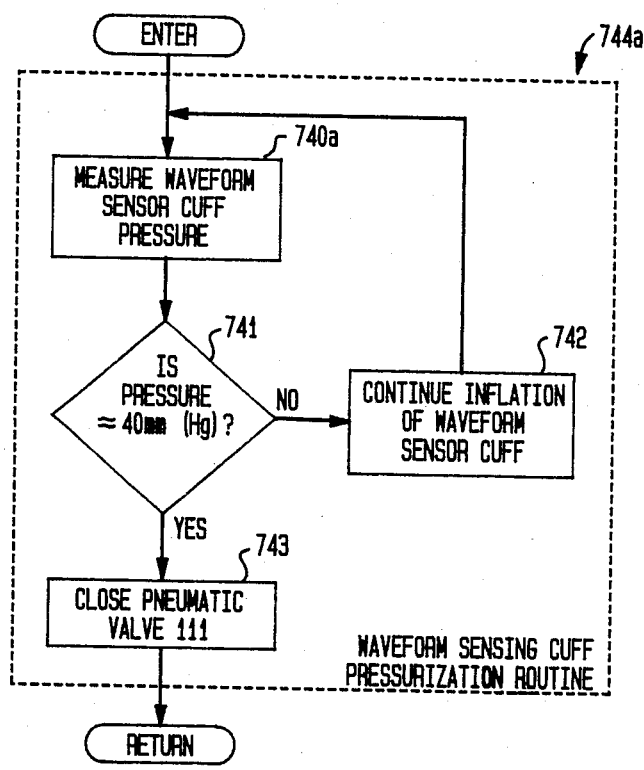
FIGS. 10A and 10B depict flowcharts of Waveform Sensing Cuff Pressurization Routine 744a and Occlusive Cuff Pressurization Routine 744b, respectively, both referred to in FIG. 8.

As noted, upon successful designation of both cuff channels, execution transfers from block 920 of cuff Integrity Verification routine 737 to evoke two cuff inflation processes essentially simultaneously; namely inflating the waveform sensing cuff to a constant low pressure of approximately 40 mm(Hg) and inflating the occlusive cuff to its appropriate target (occluding) pressure value. Specifically, after control is transferred from block 737, execution of Waveform Sensing Cuff Pressurization Routine 744(a) is initiated. Upon entry in this routine, as shown in FIG. 10a, inflation pressures are first measured and tested by block 740(a) and 741. Valve 111 (See FIG. 1A) is maintained open until the waveform sensing cuff pressure reaches 40 mm(Hg), at which time execution of block 743 causes this valve to close. Once this occurs, control exits from waveform sensing cuff pressurization routine 744a and, as shown in FIG. 8, transfers to waveform sensor initialization and occlusive cuff measurements routine 630.

Figure 10B:
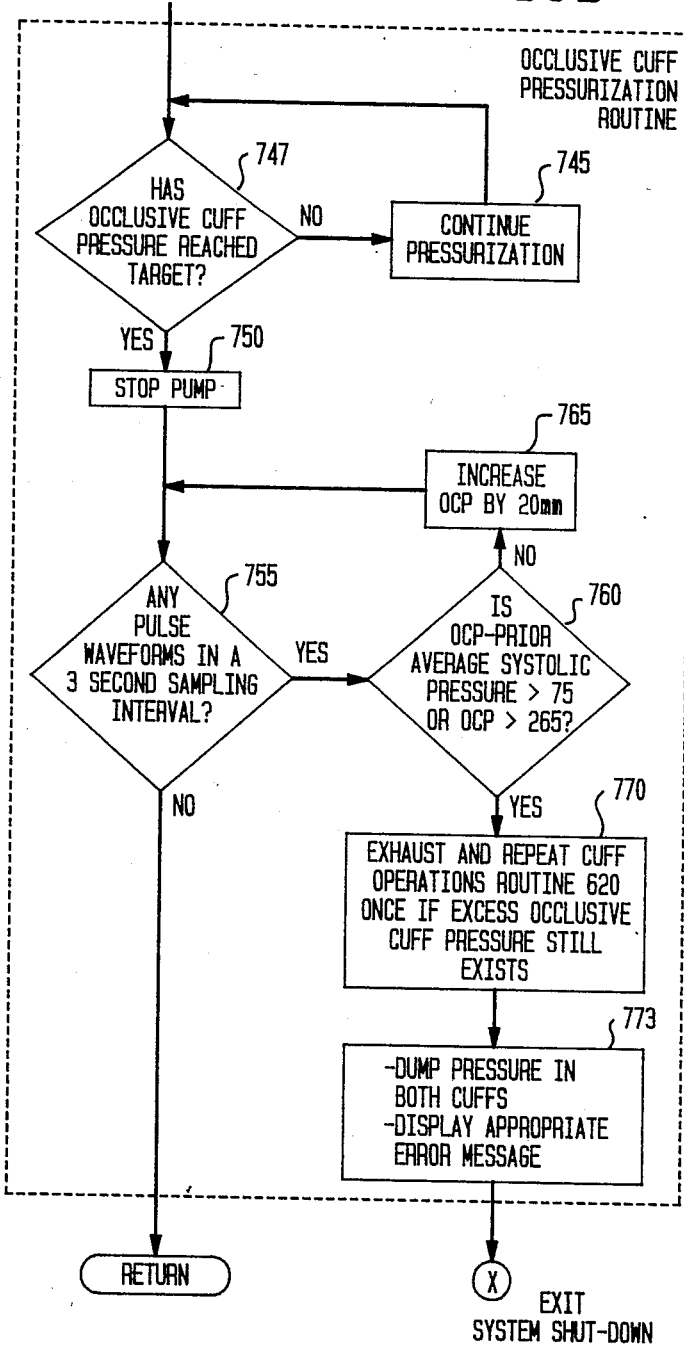

Essentially at the same time that waveform sensing cuff pressurization routine 744a is being executed, to occlusive cuff pressurization routine 744b, shown in detail in FIG. 10B is also being executed. Upon entry into this routine, decision block 747 first measures the occlusive cuff inflation pressure and, in response thereto, determines whether this pressure equals the target pressure that was previously determined in block 715 or 730. If not, block 745 is executed to continue occlusive cuff inflation. When the actual occlusive cuff pressure equals the taught pressure, control is passed, via the "Yes" path from decision block 747 to block 750 which discontinues cuff inflation by de-activating air pump 121. Thereafter, execution proceeds to decision block 755 to determine if the then existing occlusive cuff pressure is sufficient to occlude arterial blood flow, i.e. whether this pressure is at a "suprasystolic" value.

Figure 11:
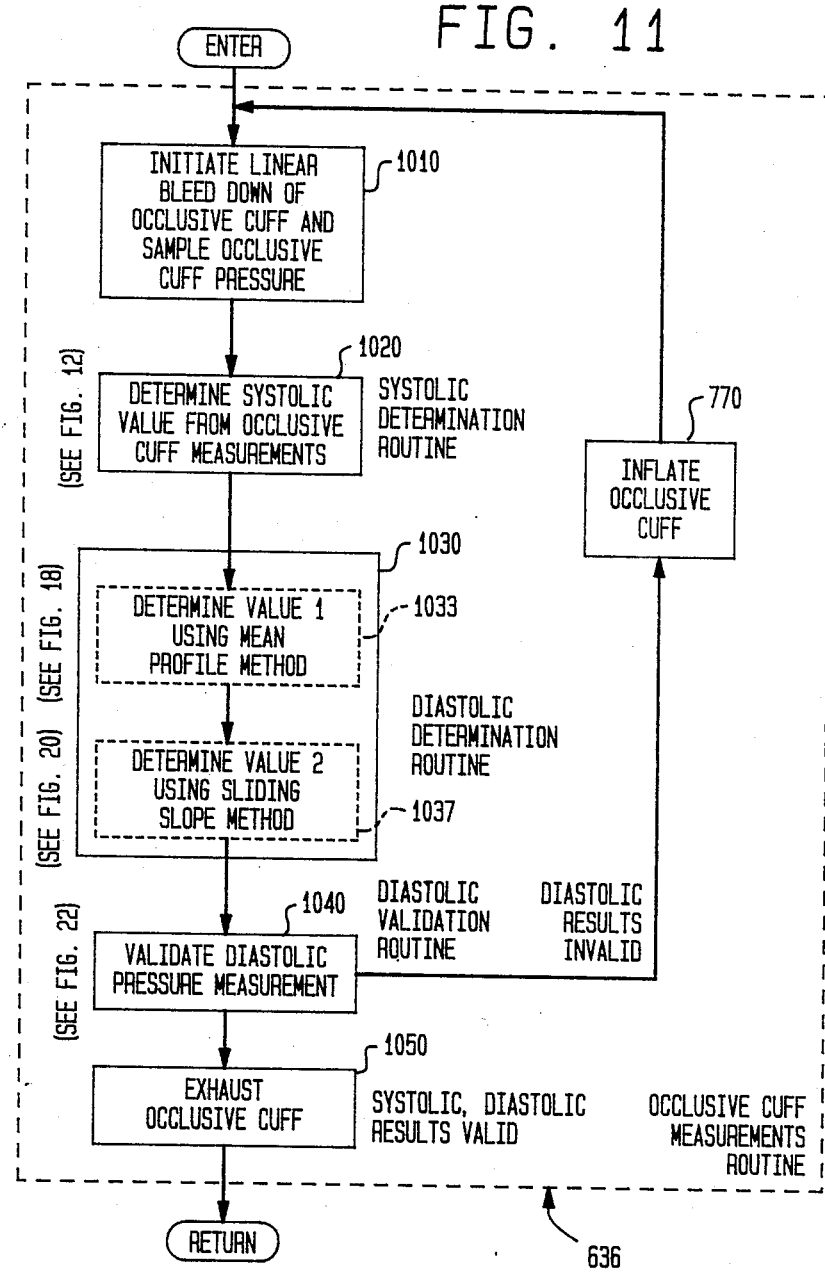
FIG. 11 depicts a flowchart of Occlusive Cuff Measurements Routine 630 referred to in FIG. 7A.

Specifically, routine 755 monitors (samples) the air pressure in the occlusive cuff over a duration of approximately 2 to 3 seconds for any perturbations attributable one or more pressure waveforms, as depicted in FIG. 5. If any such waveforms are detected, decision block 760 is first executed to determine whether the then existing occlusive cuff pressure is outside a pre-determined range, specifically higher than the average systolic pressure determined during the most recent continuous monitoring interval +75 mm(Hg) or greater 265 mm(Hg). In the event, the actual occlusive cuff pressure is too large, i.e. larger than either of these two measures, an error condition occurs. Control is then transferred to block 770 which dumps pressure in both cuffs. Inasmuch as the error condition may be due to an isolated and transient cause, block 770 re-initiates cuff inflation by transferring control to the beginning of cuff operations routine 620. If however, the error continues for a second time, then block 773 is executed which dumps the pressure in both cuffs, displays an appropriate error message and then shuts the system down. Alternatively, if the occlusive cuff pressure is below the two measures specified in decision block 760, then block 765 is executed which results in increasing the applied occlusive cuff pressure by approximately 20 mm(Hg). The occlusive cuff pressure keeps increasing in 20 mm(Hg) increments until arterial blood flow is completely occluded by application of a suprasystolic cuff pressure sufficient to prevent any pressure waveforms from occurring during a continuous 3 second period; thereafter control exits this routine via the "No" path from decision block 755. At the instant both cuffs are properly inflated, i.e. after routines 744a and 744b have been completely executed, control as shown in FIG. 7A exits from cuff operations routine 620 (FIG. 8) to waveform sensor initialization and occlusive cuff measurements routine 630 (FIG. 11). This latter routine is comprised of two portions, routine 633 and routine 636—the former will be discussed in the next section, and the latter will be discussed in the following section. While these latter two routines are in practice executed such that the waveform sampling process in each occur nearly simultaneously, these routines are shown as sequentially occurring in FIG. 7A merely for purposes of simplifying the figure and the ensuing discussion.

2.3 Waveform Sensor Initialization and Occlusive Cuff Measurements Routine 630

Upon culmination of the execution of cuff operations routine 620, control is transferred to, as depicted in FIG. 7, waveform sensor initialization and occlusive cuff measurements routine 630, which is shown in detail in FIG. 11.

2.3.1 Waveform Sensor Initialization Routine 633

Routine 633 consists of determining certain "base-level" values and relationships that are derived from waveform sensor cuff sample data acquired during each "calibration" phase. Base-level peak and trough values are also computed from the sampled waveform sensor cuff data for subsequent use in previously-described moduli table determination routine 640. Also, this routine determines the actual value of the previously described base-level waveform sensing cuff reference pressure and its rate of change. These latter values are used as comparison standards throughout the following "continuous monitoring" phase to ensure that pressure displacement waveform sample values acquired during that phase are properly referenced and thereby accurately detected.

The process by which routine 633 determines the base-level values requires a detailed description of the manner in which the analog output signal of pressure transducers 133 and 136 is conditioned prior to sampling. Specifically, as shown in FIG. 4, three analog signal components (Pw, Prs, and Pr) are segregated from a composite analog output signal produced by each transducer, illustratively transducer 133, prior to sampling and digitization via A/D converters 157A and 157B. First, a Pw component, of the pressure displacement waveform, that varies at the patient's heart-rate is separated by filtering low frequency components from the composite analog signal. The resulting Pw signal essentially consists of all amplitude values in excess of a pressure level that extends between successive waveform trough (minimum) values. This waveform component is similar to that shown in FIG. 6, but as will be made clear below, does not include all components of the pressure displacement waveform, as it referred to in other parts of this disclosure. A second analog component, Pr, is a low frequency arterial pressure displacement signal that varies in response to the patient's respiration cycle. The magnitude (amplitude) of respiratory-induced arterial displacement cycles are positive and negative relative to a computed average value (i.e., are sinusoidal in nature) and these values can be negligible or quite significant, depending on physiologic conditions of the patient, and common undergo a cyclic change at a rate of every 4-7 heart-beats. The third signal component, Prs, is comprised of the sum of a static non-varying cuff pressure value of approximately 40 mm(Hg), and the above-described Pr component. Essentially, Prs is the composite transducer signal (that represents the total waveform sensing cuff pressure) excluding the Pw component.

After the three analog signal components are separated by signal conditioner 147 from the composite output signal produced by transducer 133, Pw is routed to A/D converter 157A and components Pr and Prs are separately routed to A/D converter 157B. These two converters sample and convert these three digital signals into three streams (sequences) of discrete digital values, as previously described, reprsentative of the Pw, Pr, and Prs signal components respectively. These digital streams are processed by the computer, in a manner described below, to produce two concurrent sequences of instantaneous digital sample values. One sequence represents the simultaneously occurring pressure displacement waveform variations and the other represents the reference pressure of the waveform sensor cuff.

Specifically, the computer generates the pressure displacement waveform sequence by summing each sequential instantaneous corresponding sample value of the Pw signal component with its corresponding value of the Pr signal component. Thus, the pressure displacement waveform sampling sequence is comprised of simultaneous heart contraction and respiratory-induced components, Pw and Pr, respectively. The pressure displacement waveform sequence forms the basis of the waveform sensor measurements produced by routine 630 during the "calibration" phase as well as for the waveform sensing cuff measurements produced during the "continuous monitoring" phase. Specifically, certain ones of the pressure displacement waveform sample values occurring during the "calibration" phase are used by waveform sensor initialization routine 633 (see FIG. 7A) to ascertain the base-level peak and trough values. In particular, routine 633 computes base-level peak and base-level trough values as the average of the peak amplitudes and trough amplitudes values, respectively, of at least one sequence of pressure displacement waveforms measured at the low constant reference pressure of the waveform sensing cuff. In the event that the waveform sensing and occlusive cuffs are affixed to different limbs of the subject such as to enable simultaneous sensing therefrom of the same waveform sequence, then this waveform sequence preferably begins with the first waveform detected as part of systolic determination routine 1020 and ends with the last waveform sampled as part of diastolic determination routine 1030 (both of these routines are shown in FIG. 11 and will be discussed in detail shortly). Alternately, the base-level peak and trough values can be computed by averaging the waveform maximums measured during systolic routine 1020 and averaging the waveform minimums subsequently detected during execution of diastolic routine 1030. In the event that both the waveform sensing and occlusive cuffs are affixed to the same limb, then waveform sensor initialization routine continues to sample incoming pressure displacement waveform data detected through the waveform sensing cuff after the occlusive cuff pressure is released and continuing for an interval lasting at least as long as 6 heartbeats, or a complete respiratory-induced displacement cycle. The commencement of the "continuous monitoring" phase is delayed such that two simultaneous sequences of a suitable number of maximums and minimums can be measured from the waveform sensing cuff to facilitate computation of base-level peak and trough values. Once the base-level peak and trough values are computed, control proceeds to moduli table determination routine 640 which uses these values in fabricating a pressure/displacement look-up table, as previously described.

As noted, the validity of any displacement waveform sample is also dependent upon a process of measurement and correction of the reference pressure component in the low pressure waveform sensor cuff. Hence, simultaneous with the computation of the base-level peak and trough values during the "calibration" phase, routine 633 also computes a base-level reference pressure. Specifically, the low frequency sample value sequence, i.e., the digitized equivalent of the Prs analog signal component, is averaged over one or more preferably complete respiratory-induced arterial displacement cycles, utilizing area summation or integration and time division methods that are well-known in the art, such that the base-level reference pressure and its rate of change (if any) are determined during the initial "calibration" phase and first few minutes of the "continuous monitoring" phase. Inasmuch as the rate of change in the base-level reference pressure reflects any initial pneumatic system leakage and/or other system conditions such as, for example, temperature effects on air pressure in the pneumatic system and/or on pressure transducer operation; the base level reference pressure may not remain constant. Instead this pressure is apt to slightly decrease with time. Since the base-level reference pressure value is initially ascertained over a small number (e.g., one or two) of respiratory-induced arterial displacement cycles during the "calibration" phase, the "actual" reference pressure values are also computed in like manner throughout the "continuous" monitoring phase. Any differences between the base-level and actual values are used to correctively adjust the pressurization of the waveform sensing cuff during the "continuous" monitoring phase in order to maintain the cuff pressure at the base-level reference value (i.e., approximately 40 mm(Hg)). Specifically, the "actual" reference pressure values are computed in the same manner as the base-level value. In particular, during the "continuous" monitoring phase, "actual" reference pressure values are continuously computed for each adjacent group of, at least two or preferably about three, respiratory-induced arterial pressure displacement cycles (of approximately 8-15 pressure waveforms each) so as to update the "actual" reference value every 15 seconds or so. Whenever a pre-defined difference, on the order of one or a few mm(Hg), is determined to exist between the "actual" and the "base-level" reference pressure values, the pressure difference is eliminated through appropriate corrective inflation or deflation of the waveform sensor cuff. In addition, the rate of change occurring between any two sequential "actual" reference pressure values is computed with respect to the intervening time interval that transpired since the prior correction of waveform sensing cuff pressure (or if none occurred since the prior calibration, since the determination of the "base-level" value itself). Each rate of change is subtracted from the "base-level" standard rate of change, and the resulting differential rate of change is used to determine if the reference pressure change remains relatively stable. If, by contrast, the absolute values of two such sequentially occurring differential rate of change values both exceed a pre-defined limit, preferably a factor of about $-1$ of the "base-level" rate (having a value such as to reflect excessive system leakage), then the monitoring process is terminated and another re-calibration phase is initiated. In the event that the differential rate of change values still remain excessive, then the pressure in the waveform sensing cuff is vented, an appropriate error message is displayed and the system is shut-down.

2.3.2 Occlusive Cuff Measurements

2.3.2.1 Overview

Essentially at the same time that waveform sensor initialization routine 633 is executed, as described above and shown in FIG. 7A, computer 200 also executes occlusive cuff measurement routine 636. These two routines are only executed during the "calibration" phase. Execution of occlusive cuff measurement routine 636 causes the occlusive cuff pressure to be reduced or bled-down, preferably at a linear rate, and the systolic and diastolic pressure values to be determined based upon simultaneously occurring pressure displacement waveform activity detected through perturbations in the occlusive cuff pressure.

Occlusive cuff measurement routine 636 is shown in flowchart form in FIG. 11. Upon entry into this routine, control is first passed to occlusive cuff bleed-down routine 1010. This routine initiates and controls the linear bleed-down of occlusive cuff by providing, as previously described, an appropriate 8-bit bleed-down value, via I/O port 201 and leads 163, to bleed rate control 144 (see FIG. 1B). With the occlusive cuff connected as shown in FIG. 1A, computer 200—through pneumatic valve 111, pressure transducer 133, signal conditioner 147, A/D converters 157A, 157B, and I/O port 203—obtains a sequence of digitized samples of the occlusive cuff pressure occurring during its bleed-down.

Once an initial number of these samples has been taken and stored in RAM memory 212 (see FIG. 1B), control passes to systolic determination routine 1020, which calculates the systolic pressure based upon large number of pressure samples. Specifically, this routine, in a manner described in detail below, first measures the average time interval occurring between the peaks of detected pressure displacement waveforms to determine the existence of any "absent" pulse intervals or "windows". Since the force imparted by pulsatile arterial blood pressure waveforms can and, in fact, does normally vary from heart-beat to heart-beat, some resulting displacement waveforms occur with a greater intensity (amplitude) than others. As a result, some of these resulting waveforms may occur with an amplitude (force) that is too small to impart any measureable variations to the pressure of the occlusive cuff during the early relatively high-pressure part of the bleed-down process. These waveforms are thus commonly referred to as being "absent" during a pre-determined or calculated sampling interval or "window" Absent pulse windows (APWs) may also be illustratively caused by an irregular heart-beat which generates non-uniformly spaced pressure displacement waveforms. The resulting number and relative position (in the waveform sequence) of such APWs that may be identified determines, in part, which specific method will be used for measuring the systolic pressure. Specifically, the systolic determination routine 1020 selects, largely based upon this APW information, one of four methods which are described in much greater detail below.

Once the systolic measurement has been determined, control is passed to diastolic determination routine 1030 which primarily consists of two separate but essentially simultaneously executed processes, namely mean profile routine 1033 and sliding slope routine 1037, that process additional pressure displacement waveform sample data to generate two separate diastolic pressure values, DPmp and DPss, respectively. Validation routine 1040, in a manner to be described shortly, compares these two diastolic pressure values and, based upon the magnitude of any difference therebetween and on the type of variability encountered in each of the two processes, selects one of these two values, and, if necessary, modifies it to produce a final diastolic pressure measurement. If, by contrast, validation routine 1040 cannot make such a selection, due to excessive variability in the sampled pressure waveform data, then this routine re-inflates the occlusive cuff, via occlusive cuff inflation routine 770, to repeat all the occlusive cuff measurements.

Once validation routine 1040 produces a diastolic pressure measurement, the occlusive cuff is completely deflated at a fast pre-defined rate by execution of routine 1050, and thereafter control exits from occlusive cuff measurement routine 636 and transfers to moduli table determination routine 640.

2.3.2.2 Systolic Measurement

To enhance understanding the operation of systolic occlusive cuff measurement routine 1020 (referred to in FIG. 11), and shown in detail in flowchart form in FIGS. 12A-12G, the readers attention is first directed to FIGS. 15A-D, 16A-H and 17A-H which graphically show the operation of this routine for various illustrative sequences of PWA (pressure waveform amplitude) peaks.

FIGS. 15A-D illustratively show four separate cardiovascular hemodynamic sequences of arterial blood pressure waveform amplitude (PWA) values occurring during the bleed-down of an occlusive cuff. Although individual blood pressure waveforms are of the form shown in FIG. 6, for purposes of clarity, only the peak amplitude of each pressure waveform is shown as a vertical line in FIGS. 15A-D. Hence, each line signifies the occurrence of one pressure waveform during a cuff measurement sequence of several waveforms. The four sequences reflect hemodynamic conditions of increasingly variable nature, depicted in such a manner as to be taken as representative of a broad range of cardiovascular activity that can be encountered in practice.

Superimposed upon each pressure waveform amplitude sequence in FIGS. 15A-D is one or more generally descending dashed lines, each of which depicts the decreasing pressure of an occlusive cuff. Each dashed line is an illustrative example of a separate occlusive cuff bleed-down that could occur during the systolic measurement routine. As shown, the pressure in an occlusive cuff is bled-down at an approximately linear rate which is always interrupted by a constant pressure sampling interval that is depicted by a horizontal dashed line segment. The location of the alternate dashed lines of FIGS. 15C and 15D differ from each other in that the position of each line is dependent upon the time at which occlusive cuff pressure bleed-down process is initiated relative to the particular waveform sequence. Since initiation times are random in nature, initiation time is often a factor which influences the measurement results of any occlusive cuff process known in the art, particularly when substantial hemodynamic variability is present.

Whenever any blood pressure waveform sufficiently distends an arterial wall to produce a force which generates a pressure onto the occlusive cuff in excess of the simultaneously occurring occlusive cuff pressure represented by the dashed line, that force increases the pressure of the air contained within (internal to) the occlusive cuff. This increase generates a pressure pulse, i.e. a so-called pressure displacement waveform, which varies the air pressure in the occlusive cuff and is, in turn, sensed by control and measurement unit 100. Conversely, whenever any blood pressure waveform results in a force that produces a pressure onto the occlusive cuff which is equal to, or less than, the internal occlusive cuff pressure, then no pressure variations are imparted to the occlusive cuff pressure. In this case, a pressure displacement waveform is not detected. The sampling interval of these latter undetected waveforms are the previously described APWs (absent pulse windows). FIGS. 16A-H graphically show sequences of detected relative pressure displacement waveform amplitudes (PWAs)—i.e. amplitudes in excess of the descending occlusive cuff pressure—that illustratively are detected using an occlusive cuff for each of the dashed line bleed-down sequences shown in FIGS. 15A-D.

Systolic determination routine 1020 produces through occlusive cuff measurements a final value of systolic pressure, SP, and this routine possesses specific measurement attributes which advantageously enhances "continuous monitoring." In this regard, the primary attribute of systolic routine 1020 is its ability to compensate for heartbeat-to-heartbeat hemodynamic variability and bleed-down initialization random errors (due to the occlusive cuff pressure not being equal to the initially-detected pressure waveform peak pressure) that are a source of measurement unreliability with occlusive cuff techniques known in the art. Essentially, this routine consists of sampling for a sequence of typically 4-6 pressure displacement waveforms during the initial phase of the occlusive cuff bleed-down process (during the period when the occlusive cuff pressure is initially decreasing and then remaining constant) followed by an interpolative weighting process performed in a manner which approximates the measurement accuracy of calibrated blood pressure waveform averaging computations of direct invasive monitors. This interpolative weighting process makes use of the ascent rate during bleed-down sampling, as well as the variability during constant pressure sampling (CPS), of all PWAs detected in same sampling intervals to yield a tentative systolic pressure value, sp. Based on the type and relative amounts of hemodynamic variability, if any, exhibited in the detected waveform sequence, other compensatory methods, as will be described in detail shortly, are executed to modify, if necessary, the tentative systolic pressure in order to determine the final systolic pressure value, SP. Specifically, the interpolative process consists of determining the co-ordinate pairs of two points "A" (anchor) and "P" (pivot), based upon the amplitude value and time of occurrence (in terms of the then occurring occlusive cuff-pressure) of detected PWAs, as well as the number and relative location of any ascertained APW's, for any plausible pattern of hemodynamic variability. These two points "A" and "P" define the path of a straight line (hereinafter referred to by the term "vector") that is passed through both points. This "vector" is then linearly extended backward to the 70-axis from point "P" to a tentative value of systolic pressure, sp, that is determined by the x-intercept value. Thereafter, the final systolic pressure value, SP, is taken to be either the value of sp itself or this value modified by a calculated amount which compensates for specific types of hemodynamic variability indicated by the detected PWA sequence.

With the foregoing in mind, an explanation will now be presented of the flowchart of systolic determination routine 1020, shown in FIGS. 12A–12G.

After bleed-down of the occlusive cuff has been initiated and the first pressure displacement waveform peak has been detected by routine 1010 (see FIG. 11), control is first passed to block 1101 within systolic determination routine 1020 shown in FIG. 12A. This block determines the values of the first two PWA peaks, PWA1 and PWA2, occurring during bleed-down along with the simultaneously occurring occlusive cuff pressures $OCP_1$ and $OCP_2$, and executes pulse window interrogation (PWI) routine 1250 to determine the number of any APW's occurring between these peaks. Routine 1250, in a manner which is described in detail later, establishes the duration of a PWA peak sampling "window," based upon either certain pre-established standard PWA interval values or the actual duration between earlier-occurring PWA peaks through which the occurrence of a prior APW has been ascertained.

On completion of block 1101 and measurement of PWA1 and PWA2, control transfers to execution block 1109 which terminates occlusive cuff pressure bleed-down and maintains the occlusive cuff pressure at a constant value, $OCP_c$, which is the x coordinate of anchor point "A" and which preferably occurs between the value of PWA2 and the value of the next subsequentially occurring PWA peak, PWA3.

Thereafter, block 1113 measures the third and fourth PWA peaks, i.e. PWA3 and PWA4, occurring at constant cuff pressure $OCP_c$ and, through the continued execution of PWI routine 1250, updates the identification of, and the number of, any APW's intervening between peaks PWA3 and PWA4. During this APW updating process, the duration of the PWA sampling window is adjusted based upon the actual time of occurrence of prior PWAs, e.g. PWA3 and PWA4. Once all these PWA peaks and intervening APW's, if any, have been detected, decision block 1114 determines the variability of the resulting sequence of PWA peaks, i.e. PWA1, ..., PWA4. In the event the measured PWA-to-PWA variability is low—i.e. the values of these peaks satisfy certain empirically defined mathematical criteria defined in block 1114, then the systolic pressure can be readily determined—based on a minimum number of 4 PWAs and the shortest sampling duration possible at the constant cuff pressure $OCP_c$. In particular, if first, no APW's have occurred prior to PWA4, and second, the ascending values of peaks PWA1 and PWA2 lie between certain pre-defined empirical ranges as determined by various inequalities in decision block 1114, and third, the values of PWA3 and PWA4 are each within 15% of the minimum of PWA3 and PWA4, then control passes to block 1115, in FIG. 12B, via the "yes" path from decision block 1114.

Block 1115, when executed, determines the co-ordinates ($x_p$, $y_p$) of pivot point "P". Specifically, $x_p$ is the average value of the occlusive cuff pressure values, $OCP_1$ and $OCP_2$, which existed at the time of occurrence of peaks PWA1 and PWA2, respectively, and $y_p$ is the average value of the peak values PWA1, and PWA2. Once the "P" co-ordinates are determined, block 1117 then computes the y coordinate of anchor point "A" as the average value of all PWA peaks that occur during the constant pressure sampling interval, henceforth referred to as PWX. The x co-ordinate of point A is taken to be the pressure of the occlusive cuff during the constant pressure sample interval, i.e. $OCP_c$. Thereafter, control passes to block 1116 which executes systolic pressure intercept calculation routine 1300 shown in FIG. 14, which connects the co-ordinates of anchor point "A" and pivot point "P" to create the vector which is then extended downward to the x-axis, i.e., to an intercept point. In particular, upon entry into this routine, block 1305 calculates the slope, m, of the vector which passes through points "A" and "P." The value of slope m is then used in execution block 1310 to calculate the x-intercept, i.e. the intermediate systolic pressure value, sp, of this vector.

Alternatively, if signal noise or other similar adverse affects constantly occur, the intermediate systolic pressure, sp, can be taken as the x co-ordinate of the point of intersection of the downwardly extended vector with a slightly raised horizontal line (e.g. where y=0.5) in order to compensate the systolic pressure for these factors. Once the intermediate systolic pressure is obtained, control is then transferred via block 1118 to block 1220 (in FIG. 12G) which assigns this intermediate systolic pressure as the final value of systolic pressure, SP, and thereafter control exits from systolic determination routine 1020 to diastolic routine 1030.

Alternatively, in the event that decision block 1114 determines that the variability between the detected PWA peaks exceeds the specified ranges, control is transferred, via its "No" path to block 1119. This latter decision block tests for an aberrant value of PWA1, i.e. a value which exceeds the value of PWA2 by more than approximately 25% of PWA2. Should this occur, then the PWA1 value is set equal to the 1.25 times the PWA2 value. Control is thereafter passed to block 1121 which extends the duration of constant pressure sampling for the measurement of additional PWAs. Specifically, sampling at the constant pressure $OCP_c$—henceforth referred to as constant pressure sampling or "CPS"—is continued for a finite number of PWA sampling windows, based on the APW occurrences that are determined by execution of PWI routine 1250, until one of the following conditions occurs: (a) four adjacent PWAs (i.e. PWA3, ..., PWA6) with no intervening APW's are detected during four adjacent constant pressure sampling windows, (b) a minimum of three PWAs (i.e. PWA3, PWA4, PWA5) and one or two intervening APW's are detected during a total of 5 adjacent pulse window sampling, intervals, or lastly, (c) five such PWAs with up to three intervening APW's are detected during a maximum of 8 sequential pulse sampling windows. These PWA amplitude values, the corresponding cuff pressure at which each occurs, and the number and relative location of all intervening APW's are all appropriately stored in RAM memory within computer 200 as they are detected.

Control is thereafter transferred to decision block 1123—shown in FIG. 12C—which tests for the occurrence of an undesirable PWA sequence, namely those otner than that defined in block 1121 or in block 1281 of PWI routine 1250 (which is described in detail later in conjunction with FIGS. 13A-B). If such an undesireable sequence occurs, control then passes to block 1124 which terminates the occlusive cuff measurement process, dumps the pressure in the occlusive cuff and proceeds to routine 620 to completely repeat the occlusive cuff measurements. Alternatively, if the PWA sequence can furnish the basis of an accurate systolic measurement, then control transfers via the "no" path of decision block 1123, to execution block 1129. This latter block calculates the co-ordinates ($OCP_c$, PWX) of anchor point "A" where PWX is the average value of all the sampled PWA peaks occurring after PWA2 (i.e. PWA3, PWA4, ..., PWAn) which were sampled pursuant to block 1121, and $OCP_c$ is the constant pressure at which the occlusive cuff is maintained after the second pressure waveform peak PWA2. Thereafter, co-ordinate determination routine 1141 computes the co-ordinates of pivot point "P" ($x_p$, $y_p$) using formulas that differ based on the number of intervening absent pulse windows, (either confirmed APWs, or tentatively identified APW's hereinafter referred to as TAPWs) that occured between PWA1 and PWA2. Specifically, when no APWs are identified to have occurred between PWA1 and PWA2, which is the most typically encountered hemodynamic condition and is shown in FIG. 16A, then $x_p$ is taken to be the average of cuff pressures, $OCP_1$, and $OCP_2$, that existed at the time PWA1 and PWA2 occurred, and $y_p$ is taken to be the average of the values of PWA1 and PWA2. However, if one such APW occurred therebetween, then xp is instead taken to be equal to a pressure value greater than $OCP_2$ by an amount equal to one-half of the amount of pressure reduction, (i.e., $OCP_{APJ}$) that occurred during the previous sampling window based on ongoing pulse interval calculations that are performed in PWI routine 1250 (to be described later). Furthermore, if two such APWs are determined by PWI routine 1250 to have occurred, then the $y_p$ computation is also altered, such that $y_p$ is set equal to the value of PWA1 plus one-fourth of the difference between PWA1 and PWA2. Control then proceeds from block 1141 to block 1145—see FIG. 12D—which executes systolic pressure intercept calculation routine 1300 to find the above described x-intercept value that defines the intermediate systolic pressure value, sp.

Once this intermediate value has been determined, decision block 1168 then tests for a particular type of hemodynamic variability which requires additional PWA sampling and measurement computations. Specifically, whenever APWs occur after, but not before, PWA2, control is transferred to execution block 1169 (shown in FIG. 12E) via the "yes" path from block 1168. Execution of block 1169 causes a second sampling interval to occur during which the air pressure in the occlusive cuff is first reduced by a pre-defined amount, preferably about 10 mm(Hg), and thereafter the pressure is then maintained constant at the value $OCP_{2c}$ for a second constant pressure sampling (CPS) interval. During this second CPS interval, block 1173 executes PWI routine 1250 which samples the occlusive cuff pressure for a pre-selected number of additional sampling windows. This number is dependent upon the number of previously identified APW's occurring during the first CPS interval. Specifically, if one, two or three APW's were previously detected, then sampling continues for six, seven or eight sampling windows during the second CPS interval, respectively. The amplitudes for this second sequence of measured pressure displacement waveforms (denoted as, $PWA_{21}$, $PWA_{22}$, ..., $PWA_{2n}$), as well as the relative position and number of intervening APW's, if any, occurring during the sampling windows of the second CPS interval are stored in RAM 212 (see FIG. 1B) for subsequent processing.

Figure 12B:
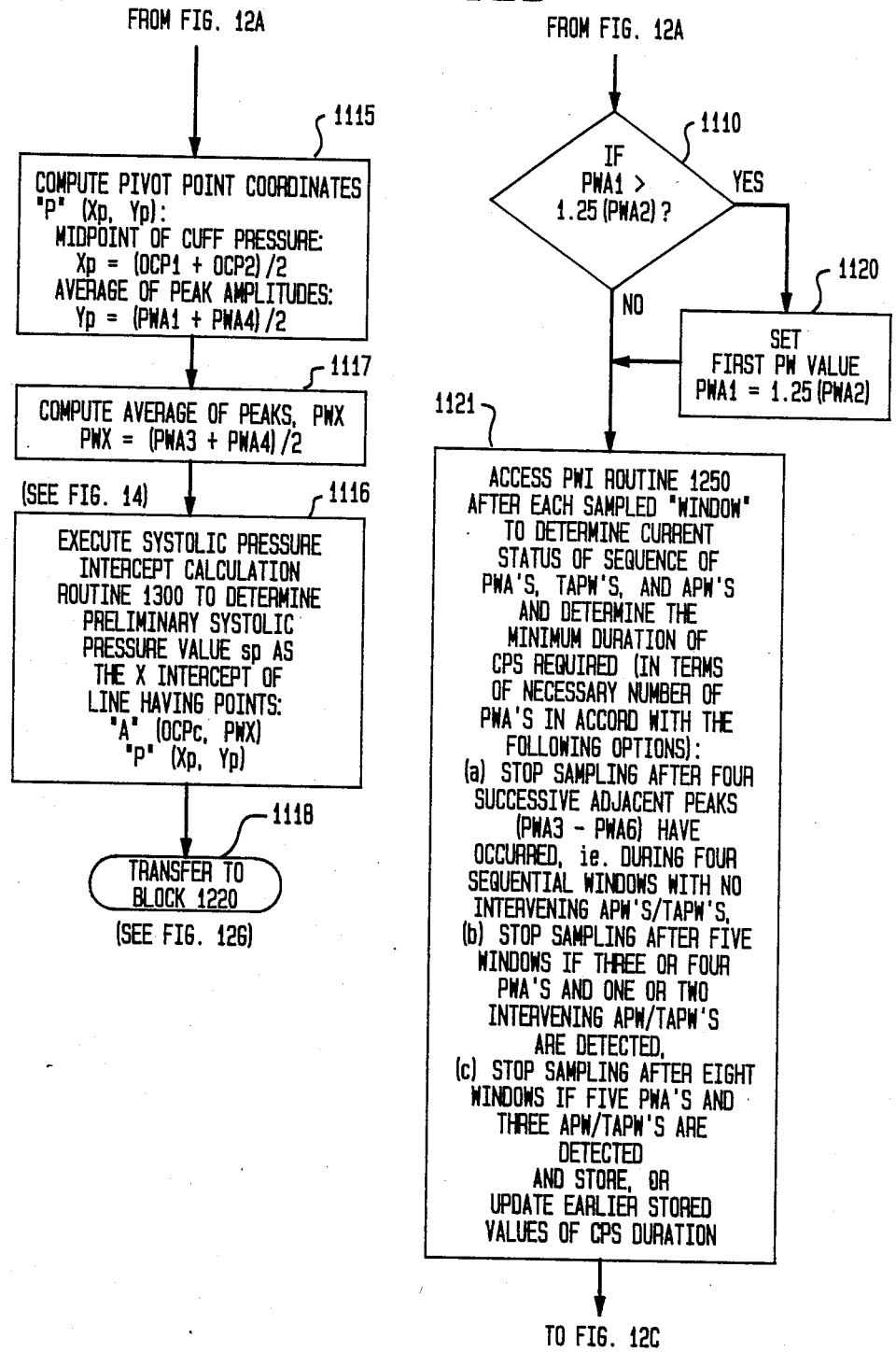
Figure 12C:
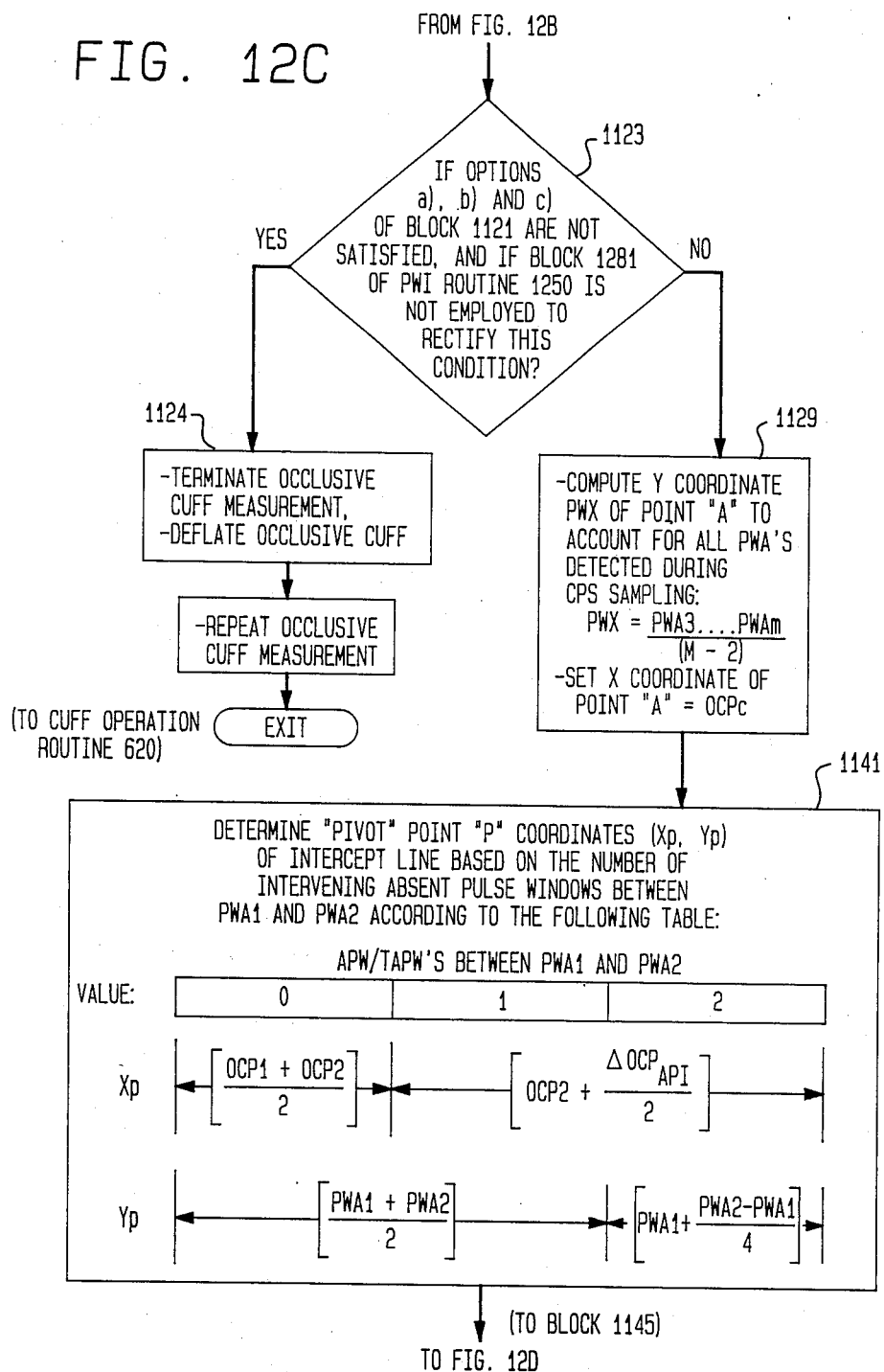
Figure 12E:
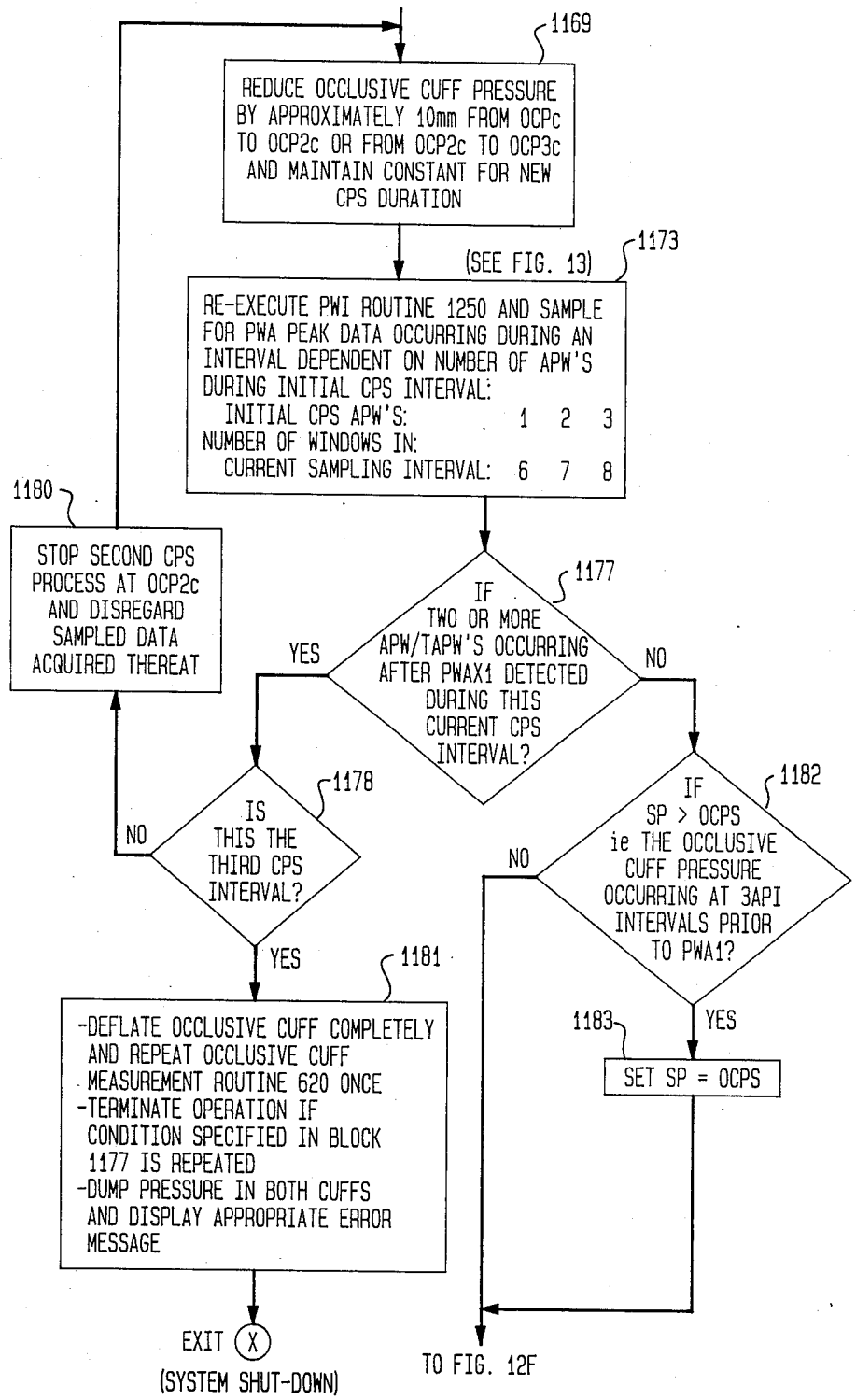

Thereafter as shown in FIG. 12E, decision block 1177 tests for the rate of occurrence of APWs in the second CPS interval at $OCP_{2c}$. Specifically, when two or more APWs are identified to have occurred after the first PWA is measured in any subsequent CPS, that CPS interval (denoted as PWAx interval) is terminated and execution blocks 1169 and 1173, as described above, are repeated once, as directed by execution of decision block 1178 and block 1180, such that a third CPS interval is conducted at $OCP_{3c}$. If the APW test of decision block 1177 fails again at $OCP_{3c}$, i.e. during this third CPS interval, control is transferred from block decision 1178, via its "yes" path, to block 1181. When executed, this latter block terminates the occlusive cuff measurement process, dumps the occlusive cuff pressure and repeats the occlusive cuff measurement process by transferring control to routine 620. If re-execution of the occlusive cuff measurement process fails to produce a PWA sequence that satisfies the test in decision block 1177, then block 1181 terminates all the occlusive cuff measurements, dumps the air pressure in both cuffs and displays an appropriate error message. System shutdown follows thereafter.

Alternatively, if the number of detected APW's is sufficiently small (e.g. one) during either the second or third CPS, block 1177 transfers control, via its "no" path to decision block 1182 which sets a limit on the value of intermediate systolic pressure sp determined pursuant to the execution of routine 1300 as previously envoked by block 1145. This limit on the intercept calculation effectively prevents unlikely but possible artifact occurences from causing a substantially erroneous final systolic pressure measurement. Specifically, in the event that the x-intercept sp value previously determined in routine 1300 exceeds a specified occlusive cuff pressure, OCPs, control is transferred from block 1182 via its "yes" path to execution block 1183 and the specified OCP (i.e. OCPs), becomes the value of sp instead of the value determined by routine 1300. In block 1182, the specified pressure value, OCPs is interpolated from previously recorded actual linear bleed-down data to be the cuff pressure that existed prior to PWA1 by the equivalent bleed-down amount of three sampling windows where the duration of one such window is determined by PWI routine 1250 as the average of previously measured heart-rate intervals.

After the sp value has been redefined if necessary, control is then transferred from block 1183, or via the "no" path from block 1182 to block 1185—shown in FIG. 12F. Block 1185 first finds the three largest PWA peak values occurring during the most recent CPS interval (e.g., $PWA_{2x}$, $PWA_{2y}$, $P_{2z}$, assuming the second CPS interval was the most recent) and calculates their average value $PWY_p$. Thereafter, this block also calculates the average value PWY, of all the detected PWA peaks occurring during tne most recent sampling interval (e.g., $PWA_{21}$, $PWA_{22}$, ..., $PWA_{2n}$, again assuming the second CPS interval is the most recent). Lastly, this block determines the differential occlusive cuff pressure, OCP, which is the total change in occlusive cuff pressure from that of the original CPS to the pressure of the most recent CPS interval (e.g. $OCP_c-OCP_{2c}$ or alternately $OCP_c-OCP_{3c}$ if the third is the most recent). Once these operations are complete, execution block 1187 calculates final systolic pressure SP by modifying the intermediate systolic pressure value, sp, based upon the differential occlusive cuff pressure OCP, and the calculated average values PWY, PWX and $PWY_p$.

After the final systolic pressure value, SP, is calculated, control then proceeds to decision block 1188 which tests the difference between the intermediate and final systolic pressures, sp and SP, to determine if its downward adjustment exceeds a pre-determined maximum of 6 mm(Hg) for each APW that occurred in the first four sampling windows of the most recent CPS interval. In the event this difference is excessive, then control proceeds to execution block 1189 which increases SP by the amount which the difference, sp—SP, exceeds the predetermined maximum downward adjustment. The resulting SP value produced by block 1189 is the final systolic pressure measurement. As a result, control exits from block 1189 and thus from systolic routine 1020 and proceeds to diastolic routine 1030.

When the result of the tests in previously described decision block 1168—see FIG. 12C—is "no", this indicates the existence of absent pulse windows (TAPW or APWs) occurring between PWA1 and PWA2 and possibly during the initial CPS interval occurring after PWA2, or that no APW's have occurred after PWA1 until after the completion of the initial CPS interval. Consequently, execution proceeds through up to three additional decision blocks to set maximum limits on the intermediate sp value. These blocks, 1190, 1192 and 1194, test for the existence of 0, 1, or 2 APW(s), respectively, and whichever one of these conditions occurs first, precludes the execution of the remaining decision blocks. In the event 0, 1 or 2 APWs have occurred, blocks 1191, 1193 or 1195, respectively, are executed. These blocks set a limiting value on the intermediate systolic pressure value, sp, determined by routine 1300 through execution of block 1145. The purpose of these limits is to prevent unlikely but possible, aberrant results from producing an erroneous final systolic pressure measurement. In each of blocks 1191, 1193, and 1195 the previously determined intermediate systolic pressure value, sp, is compared with a respective one of three empirically pre-determined OCP values, $OCP_{E1}$, $OCP_{E2}$, $OCP_{E3}$, and if the value sp exceeds its respective $OCP_E$ value, then this $OCP_E$ value becomes the value of sp instead of that determined through systolic intercept routine 1300. These pre-determined $OCP_E$ values ($OCP_{E1}$, $OCP_{E2}$ and $OCP_{E3}$) are the interpolated cuff pressures that existed during the bleed-down one and one-half or one pulse window interval prior to the occurrence of PWA1 for execution of blocks 1191 and 1193, respectively, and one and one-half pulse window interval equivalents prior to the occurrence of PWA2 for execution of block 1195.

If either block 1193 or 1195 is executed, then control thereafter transfers to block 1220 which assigns the previously determined intermediate sp value, as adjusted, to be the final systolic pressure measurement, SP. This ends the execution of systolic determination routine 1020 and control is transferred to diastolic determination routine 1030.

Alternatively, if block 1191 is executed, control is transferred to block 1199 which is shown in FIG. 12G and described in the following paragraph. Alternately, in the event that control is transferred via the "no" paths of blocks 1190, 1192 and 1194, then this indicates that three or more APWs exist between PWA1 and PWA2. As a result, control is transferred to execution block 1281 of pulse window interrogation (PWI) routine 1250 which erases the previously-stored value for PWA1. The next successive PWA value after the PWA1 is then identified to be PWA1, and the OCP bleed-down is then continued until immediately after a third PWA peak (including the erased PWA1) is detected. The third PWA peak is identified as PWA2 and the bleed-down is terminated for the initial CPS interval. Block 1281 then appropriately routes execution to complete the remainder of systolic pressure determination routine.

Decision block 1199 is executed, whenever control is transferred from execution block 1191 to determine whether any intervening APWs have occurred prior to CPS thereby indicating a relatively significant amount of hemodynamic variability. Specifically, this decision block identifies any pressure displacement waveform sequence in which no APWs have occurred after PWA2 and where the hemodynamic variability of peak values PWA3 through PWA6 (as compared to their average, PWX) is significantly less than the level of variability exhibited between detected PWA1 and PWA2. As the reader will recall, the pivot point "P" coordinates (xp, yp), as computed in block 1141, are based in part on the premise that throughout the CPS interval, the amount of PWA-to-PWA variability, between PWA1 and PWA2, can be specified by the actual number of APWs encountered and the bleed-down rate. Hence, block 1199 identifies those sequences where the variability exhibited during the CPS interval is significantly less than during the PWA1-PWA2 interval. Thus, if all the conditions specified in decision block 1199 are true for a particular PWA sequence, then execution proceeds down the "Yes" path to decision block 1203. There, based upon whether one or two APW's have occurred prior to the occurrence of pressure waveform peak PWA2 (and none thereafter), such as, for example, as shown in FIGS. 16C, D, E and G, a constant, K, is set to an appropriate value. This value is used in the formula specified in execution block 1215 to modify the intermediate systolic pressure, sp, to yield the final systolic pressure value, SP. At the conclusion of block 1215, execution then exits from systolic determination routine 1020 to Diastolic Determination Routine 1030.

Alternately, if the exhibited PWA variability is generally consistent from PWA1 until the end of the CPS interval, then execution proceeds along the "no" path from block 1199 to block 1220 which then assigns the intermediate systolic pressure value, sp, to be the final systolic pressure measurement, SP. Thereafter, execution proceeds from systolic determination routine 1020 to diastolic determination routine 1030.

Figure 13A:
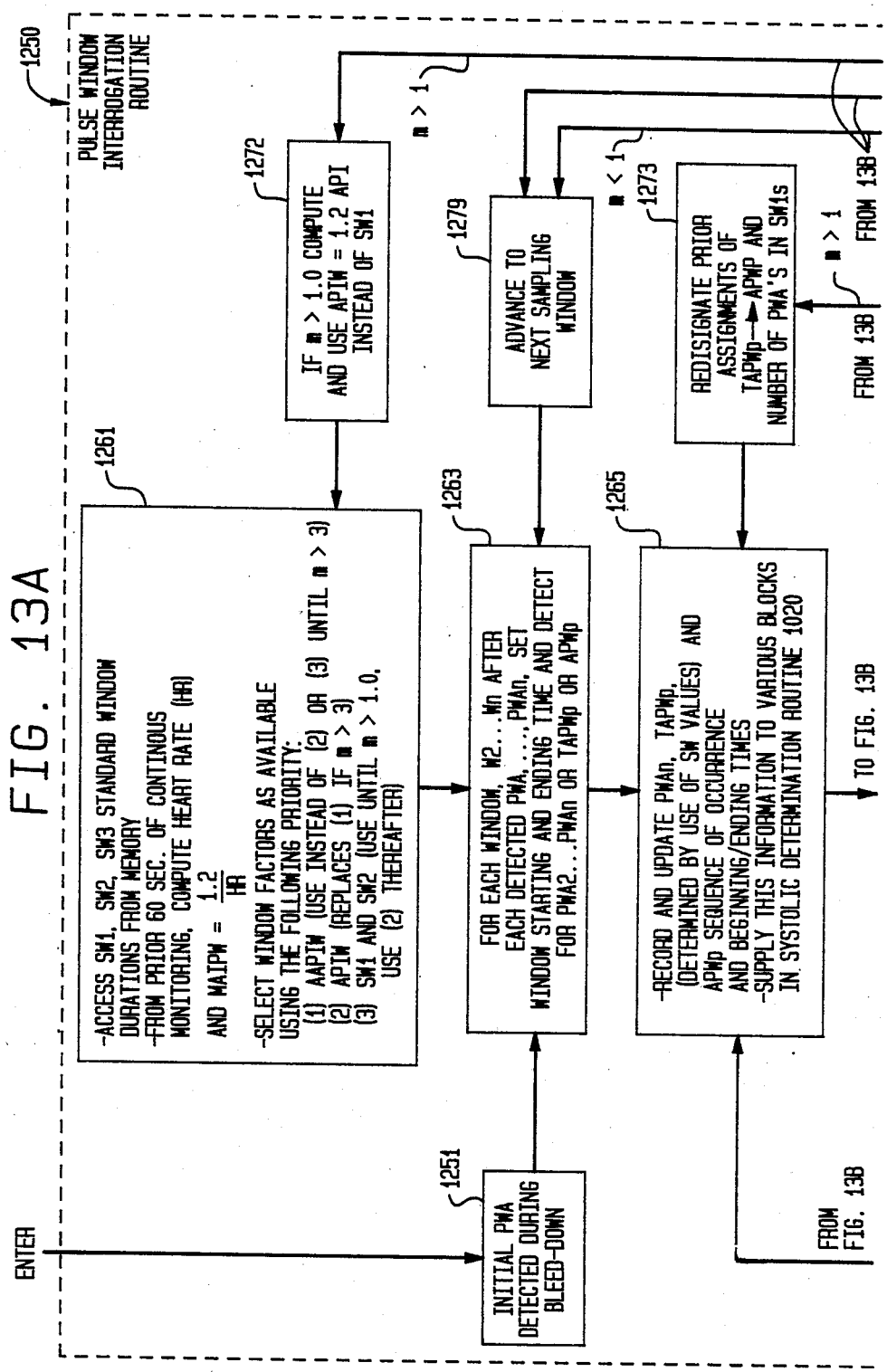
FIGS. 13A and 13B together depict a flowchart of Pulse Window Interrogation Routine 1250 referred to in FIGS. 12A-12G.
Figure 13B:
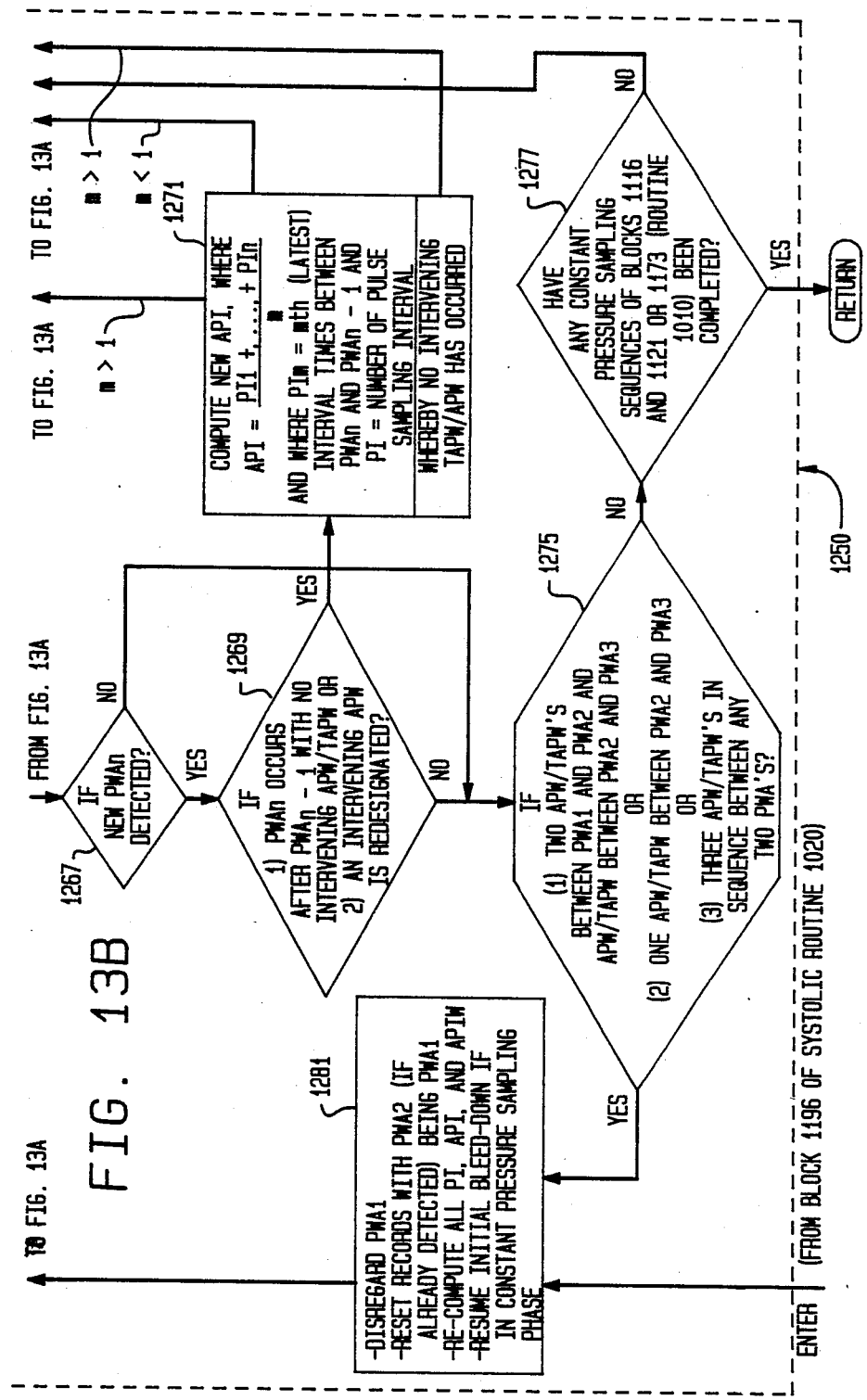
Figure 14:
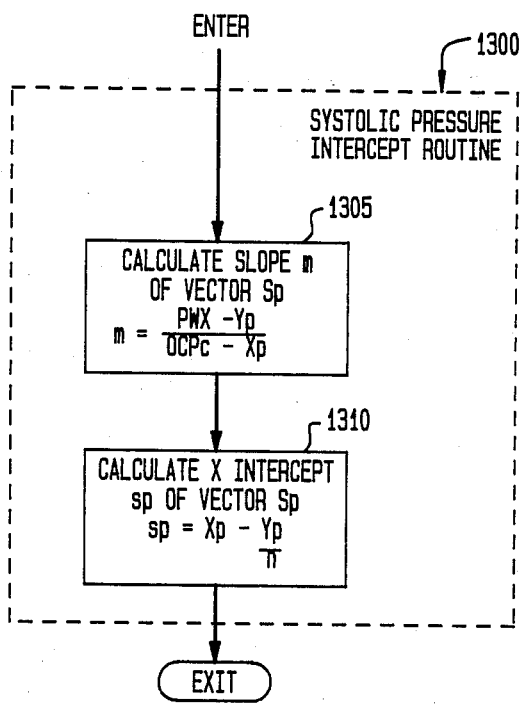
FIG. 14 depicts a flowchart of Systolic Pressure Intercept Routine 1300 referred to in FIGS. 12A-12F.

The pulse window interrogation (PWI) routine 1250 as previously discussed, is shown in flowchart form in FIGS. 13A-B. Entry into this routine occurs at block 1251, which is executed essentially simultaneously with the detection of PWA1 in block 1101 of systolic determination routine 1020. Thereafter control immediately proceeds to execution block 1263 wherein, after each PWA is detected (beginning with PWA1), a sampling window of a pre-defined duration is "opened" during which either a PWA, APW, or TAPW (tentative identification of an APW, i.e. an identification of an APW which is to be confirmed at a later processing step) is to be detected. After sampling occurs for this duration, control proceeds to execution block 1265 which records the type and time of occurrence of the intervening detected APW, if any, and updates the previously stored PWA peak sequence data based on computations performed in execution blocks 1271 and 1273, both of which are described shortly. The duration of each new sampling window is based on available pre-determined standard or updated actual heart-rate interval averages that are maintained in memory and made available through execution of block 261. In particular, as many as three types of these averages can be resident in the memory, and one is initially selected in order to set realistic durations for each successive new sampling window. Specifically, a standard window, SW1, of approximately 1.4 seconds, is used to establish the duration of the successive sampling window which begins at the time the peak of the most recently detected PWA peak, i.e. $PWA_n$, occurs—assuming this peak occurred during the most recent sampling window. However, if the most recently detected sampling event was a TAPW or APW, then a standard window, $SW_2$, of approximately 1.1 seconds in duration is used and this duration begins at the end of the prior SW1 interval. Alternatively, instead of using any such pre-determined window values, the "a posteriori" window value, specifically the average pulse interval window (APIW), if available, can be used. The APIW duration is calculated, by execution block 1272, by multiplying the duration of most recent average pulse interval (API) value, which is described next by a factor of approximately 1.2. The most recent API, which is a "running" average of all prior actual heart-rate intervals detected during systolic routine 1020, is computed by block 1271 after each additional peak, $PWA_n$, value is detected. However, prior to the execution of block 1271 for each newly detected $PWA_n$ value, decision block 1269 is executed to determine whether an intervening APW (occurring between $PWA_n$ and $PWA_{n-1}$) has occurred.

In the event a peak value, $PWA_n$, occurs during the most recent sampling window and no APW's intervene between peaks $PWA_n$ and $PWa_{n-1}$, then decision block 1269 routes control to block 1271 which initially computes and thereafter updates the APIW value. If the total number of these sampling windows is greater than unity (i.e. two or more), then control proceeds from block 1271 to execution block 1272. This latter block computes the duration of above-defined APIW for use in establishing the duration of subsequent sampling windows instead of using any standard window (SW) value. With each iterative API computation performed by execution block 1271 when "m" is greater than unity, control also proceeds to execution block 1273 which recomputes all TAPW and APW window intervals, beginning with the occurrence of PWA1, based on the latest computed API value. All the computed window intervals are substituted for the previously calculated windows. One result of these computations, for example, is the redesignation of any tentative absent pulse windows (TAPWs) to being APWs (when extreme values of API are computed in practice, it is possible that more than one APWs can be redesignated by this block). Another result of executing block 1273 is that the APW occurrence data is updated for use in block 1267. The particular sampling window occupied by an APW in any sampling sequence is identified by the subscript p as shown in block 1263.

During any "re-calibration" of the occlusive cuff (i.e., after prior continuous monitoring data has been acquired), an MAPIW value (described below), as computed in block 1261, can preferably be used in place of either SW durations when the value of "m" is one or less, or the current API value when the value of "m" is two or three. Specifically, execution block 1261 computes an average pulse interval window, for the MAPIW value, which is the product of a constant, approximately 1.2, and the reciprocal of the average heart-rate (1/HR). The heart-rate measure is computed from sequential pressure waveform data measured during the most recent measure of continuous monitoring.

At the conclusion of each sampling window, during which, as noted, APWs are detected and PWA sequences are defined, control proceeds from block 1265 to decision block 1267. If an APW has been identified in the latest window or a redesignated change to APW status has occurred, then control proceeds via its "no" path to decision block 1275, as it does from decision block 1269. Decision block 1275 tests for all possible sequences in which three APWs (and TAPW's) can occur, particularly with respect to interval between PWA1 and PWA2 and that between PWA2 and PWA3. In the event such a sequence occurs, then control proceeds to execution block 1281 which removes PWA1 from the sequence and relabels the remaining PWA peaks such that PWA2 becomes PWA1. Any intervening APWs prior to the new PWA1 are disregarded. Thereafter, bleed-down is continued until a new PWA2 is detected. Otherwise, if the bleed-down has already been terminated and CPS has commenced by the time block 1281 is executed, then all window data acquired during the CPS interval is erased from memory. For this case, bleed-down is then resumed until a new PWA2 is detected before the CPS phase can be re-entered, at which time both systolic routine 1020 and PWI routine 1250 are re-initialized. Otherwise, in the absence of a "yes" condition in block 1275, control proceeds via its "no" path to decision block 1277. This latter decision block ascertains whether window sampling should continue based on the pre-designated CPS sequences defined in other blocks of systolic routine 1020. If any of these sequences has not yet occurred, then control proceeds via the "no" path from decision block 1277 to block 1279 which opens the next sampling window. Otherwise control exits from block 1277 and PWI routine 1250, and at the completion of systolic determination routine 1020 control proceeds to diastolic determination routine 1030.

2.3.2.3 Diastolic Pressure Determination

Once the final systolic pressure value, SP, has been determined, diastolic determination routine 1030 is executed to determine two intermediate diastolic pressure values, DPmp and DPss. DPmp is ascertained via mean profile routine 1033 and DPss is ascertained from sliding slope routine 1037. Thereafter, diastolic validation routine 1040 selects one of these two intermediate diastolic pressure values, modifies it if necessary, and then sets the final diastolic pressure measurement equal to the result. Once this routine completes its execution the occlusive cuff measurement processes of the "calibration" phase are completed.

2.3.2.3.1 Mean Profile Routine 1033

Figure 18B:
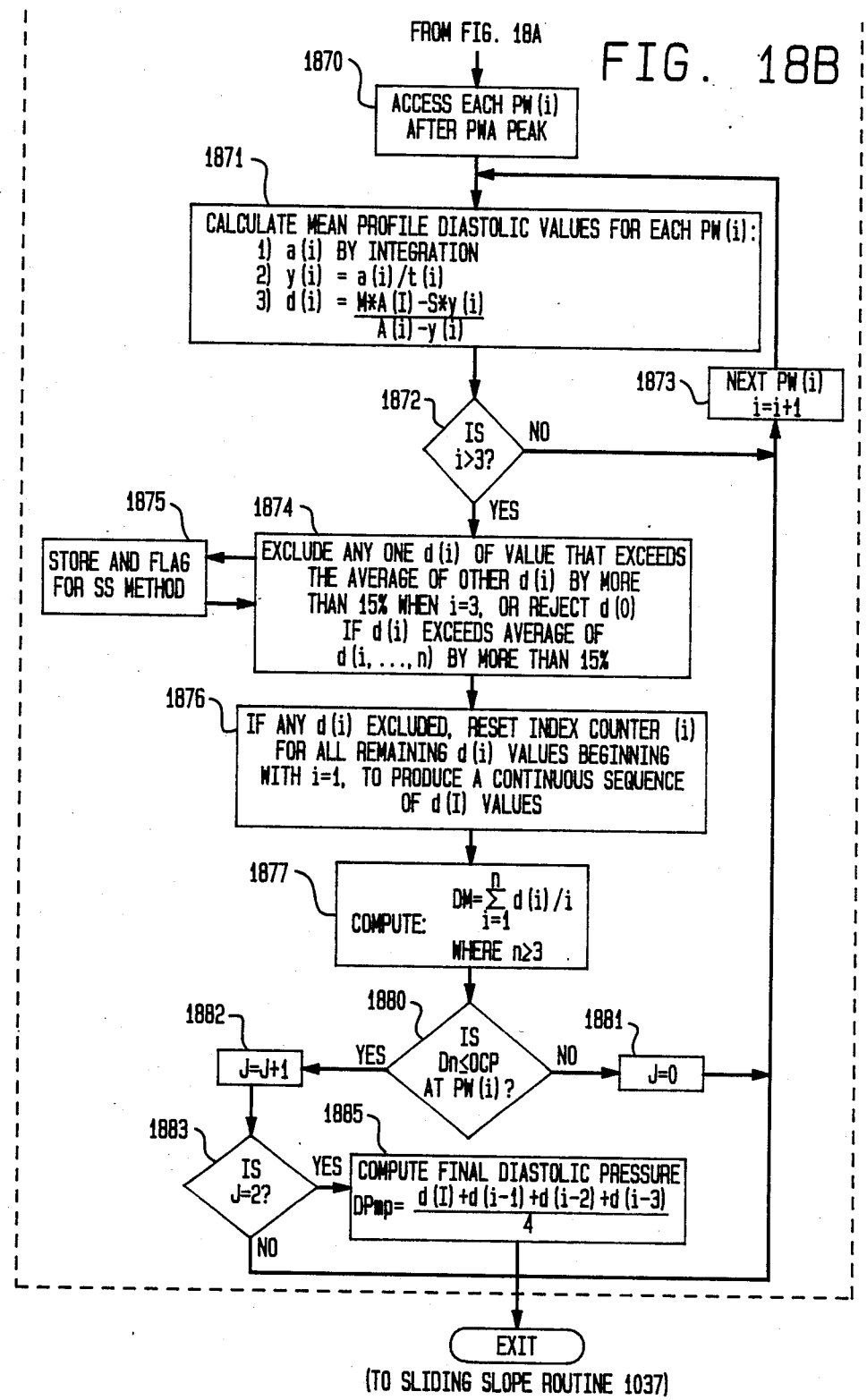
Figure 19B:
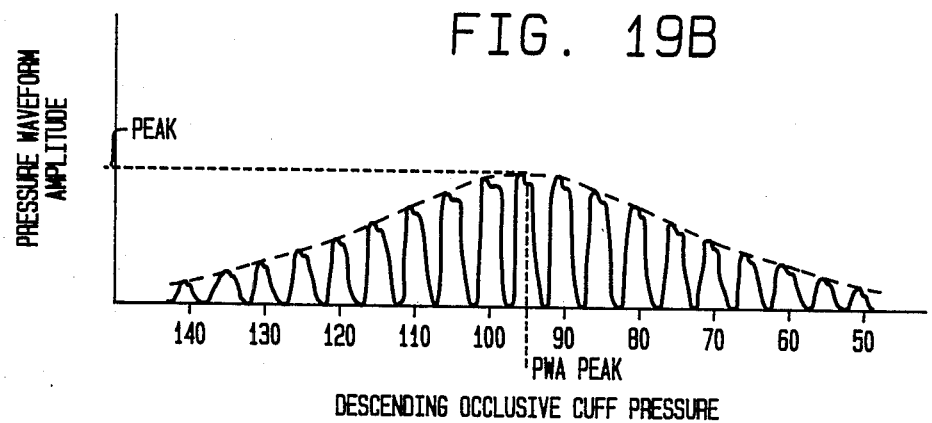
FIG. 19B is a sketch of a typical sequence of pressure waveforms—one of which is shown in FIG. 19a—sensed through Occlusive Cuff 20 during its bleed-down.

Mean profile routine 1033, is shown in flowchart form in FIGS. 18A–B. However, to facilitate understanding of the basis of this routine, discussion will first center on FIG. 19A which shows a sketch of a single typical pressure waveform. During any occlusive cuff bleed-down process of pressure sensing methods known in the art, the peak amplitude values of all detected pressure displacement waveforms exhibit the approximate characteristics of a curve, or envelope, as shown in FIG. 19B.

Pressure sensing systems known to the art measure diastolic pressure through methods based on an assumed static linear relationship between mean and diastolic pressures. It is known from empirical studies in the art tnat mean pressure M is generally equal to the value of the occlusive cuff pressure (OCP) during the largest pressure displacement waveform amplitude in the envelope (i.e. PWA$_{peak}$). Given this, these prior art methods employ what is often termed a "threshold" mechanism, which is premised on maintaining a proportional relationship between displacement waveform amplitudes at the mean and diastolic occlusive cuff pressures. Specifically, as the occlusive cuff pressure is reduced, and mean pressure (the "threshold") is determined, the linear relationship is extrapolated downward to define a suitable diastolic pressure. Unfortunately, these prior art threshold methods implicitly assume a fixed linear arterial elasticity relationship for all of the human population —which in fact is not the case, and thus use a method in which diastolic pressure measurements are inherently and disadvantageously biased to be primarily dependent on mean pressure physiologic parameters instead of parameters that are directly related to diastolic pressure. Thus the prior art methods for determining diastolic pressure generally yield inconsistent results.

The inventive diastolic mean profile method solves for a specific diastolic pressure value that can be derived from any and all of several individual pressure displacement waveforms during the latter phase of the descent of occlusive cuff pressure. Such individual measurement values depend on the values of certain waveform profile parameters that are directly related to each diastolic pressure value, namely the amplitude and integrated area of each individual pressure displacement waveform. In addition, the embodied method, preferably, but not necessarily, includes the attribute of averaging the results of several of such individual waveform measurements, e.g., approximately four to six in number, before a final weighted value is computed, in much the same manner as is done by direct invasive monitors. The inventive method is executed after the systolic and mean pressures have been determined so that the waveform parameter measurements can be taken when the occlusive cuff pressure is relatively low in order to minimize waveform distortion, if any, that usually results from relatively high applied cuff pressures. Specifically, as the applied occlusive cuff pressure is reduced from systolic and approaches the diastolic pressure, the amount of externally induced impedance and reflectance that tends to alter the frequency characteristics and relative shape of any pressure displacement waveform diminishes. This distortion gradually disappears with the latter-stage waveforms that occur after PWA$_{peak}$, and becomes essentially nonexistent when the occlusive cuff pressure becomes approximately equal to, or less than, the diastolic pressure.

Figure 19A:
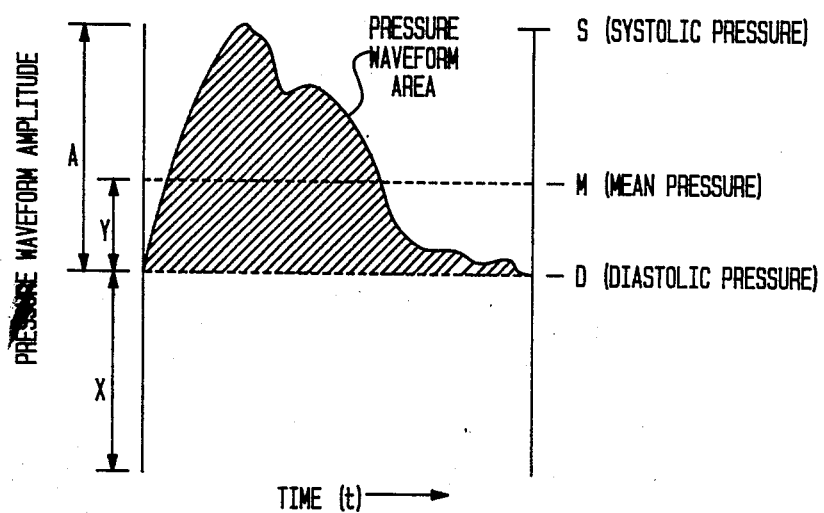
FIG. 19A is a sketch of a typical pressure waveform sensed by Occlusive Cuff 20 depicting the systolic, mean and diastolic pressures associated therewith.

The diastolic pressure of any such latter-stage pressure displacement waveform, one of which, for example, is illustratively shown in FIG. 19A, can be determined from the following relationships:

$$\frac{S}{M} = \frac{A + x}{y + x} \text{ which yields } x = (AM - Sy)/(S - M) \quad (1)$$

$$\frac{D}{M} = \frac{S}{x + y} \text{ which yields } D = Sx/(x + A) \quad (2)$$

After substituting the expression for x given by equation (1) into equation (2) and simplification, the following equation results:

$$D = AM - Sy/(A - y)$$

where A is the uncalibrated amplitude of any latter-stage pressure displacement waveform, y is the uncalibrated mean value (area/duration) of the waveform, and S, M, and D are the patient's systolic, mean, and diastolic blood pressures, respectively.

The initial phase of the mean profile method is comprised of continually testing groups of pressure displacement waveform amplitudes during occlusive cuff bleed-down in order to determine the largest waveform amplitude value and a corresponding occlusive cuff pressure (OCP) value, M. The next phase involves averaging a pre-defined sequence of individual waveform diastolic values to yield a diastolic pressure measurement. In this latter process, individual measurements of uncalibrated waveform values, A and y, are successively substituted into equation (2) above along with previously determined values of S and M, and the equation is solved for the only unknown variable term, d(i) for the diastolic pressure value associated with each particular waveform.

Now, upon entering mean profile routine 1033, as shown in FIG. 18A, blocks 1805 through 1815 are executed to find the group of PWA values (illustratively and preferably four in number) that possesses the largest average value. Specifically, block 1805 sets up a running average, $R_1$ for the first four PWAs (PWA1, ..., PWA4) which have been detected during the previously-executed systolic determination routine. Thereafter, block 1810 deletes the "oldest" PWA peak value (e.g., PWA1), replaces it with the next PWA peak value (e.g., PWA5) and then recomputes the average of the four peaks as $R_2$. If the average value increases, i.e., the value of $R_2$ is larger than that of $R_1$, thereby signifying that these four most recent peaks preceed the occurrence of the maximum peak and are thus on the ascending portion of the envelope, then decision block 1815 causes block 1810 to transfer execution, via the "Yes" path, to execution block 1813. This latter block assigns value $R_2$ to value $R_1$ and also stores the numbers (index values) associated with each of these four peaks for use in subsequent identification and retrieval of these peaks. As long as the average value continues to increase, decision block 1815 re-executes blocks 1813 and 1810 to find the four largest peaks. However, once the average value begins to decrease and continues decreasing execution proceeds, down the "No" path from decision block 1815, to block 1820. Execution block 1820 first accesses the four PWA values from which the maximum average value was calculated, and then determines the largest PWA value ($PWA_{peak}$) from among these four peaks. However, for purposes of insuring that artifacts did not cause $PWA_{peak}$ to occur, the selection of $PWA_{peak}$ is subject to the criteria that the $PW_{peak}$ value cannot exceed the value of the next largest detected PWA by more than 20%. If the value of $PWA_{peak}$ exceeds this 20% limitation, then this peak value is discarded from the analysis and the next largest peak value is selected for $PWA_{peak}$ and the selection criteria is applied to this new value. This selection process continues until a $PWA_{peak}$ value is produced which satisfies the criteria. Mean pressure M is then determined to be the occlusive cuff pressure that existed at the time of occurrence of the $PWA_{peak}$ that is finally selected.

The remaining blocks, shown in FIG. 18B complete the mean profile measurement of diastolic pressure, $DP_{mp}$. Specifically, block 1870 recognizes and enters each pressure displacement waveform occurring after $PWA_{peak}$ into an iterative process in which individual diastolic pressure measurements d(i) are determined from each successive pressure displacement waveform pursuant to execution block 1871. In particular, this block first calculates the area, a(i), under each such uncalibrated waveform, PW(i), by integrating the difference between all of the waveform sample values and the simultaneously measured linearly varying occlusive cuff pressure values. Thereafter, an uncalibrated mean pressure value, y(i), is calculated for each waveform by dividing area a(i) by its period (duration) t(i). A diastolic pressure value, d(i), is then determined for each waveform, PW(i), pursuant to step 3 in the block 1871 where: A(i) is the uncalibrated amplitude of waveform PW(i); M is the occlusive cuff pressure occurring at $PWA_{peak}$ (determined by block 1820); y(i) is the uncalibrated individual mean pressure of PW(i); and S is the systolic pressure SP determined in routine 1020.

In addition, blocks 1872 and 1874 through 1876 are used to eliminate divergent d(i) values that might occur due to artifacts. Specifically, when three d(i) values are computed, block 1874 begins to check for disparate values that vary by more than approximately 15% of each average that can be computed from all possible paired combinations of diastolic values. Any such disparate value is eliminated from further calculations in block 1874 and the indexing system (i) is appropriately adjusted in block 1876. In addition, when (i) exceeds 2, block 1874 compares each new d(i) value to the average of all prior acceptable d(i-1) values, rejecting any additional values as being disparate based upon the 15% difference. Block 1877 computes a running average of the acceptable d(i) values, $D_n$, for the next comparison. Execution blocks 1880 through 1883 determine the point when the occlusive cuff pressure converges to become equal to the continually updated average, $D_n$. At this point, a latter-stage waveform sequence can be identified such that the final diastolic pressure, $DP_{mp}$ can be computed. As indicated in block 1885 the final mean profile diastolic pressure $DP_{mp}$ is taken to be the average of four sequential d(i) values where two of such values were computed after the occlusive cuff pressure first became less than or equal to the $D_n$ value.

2.3.2.3.2 Sliding Slope Routine 1037

Figure 20A:
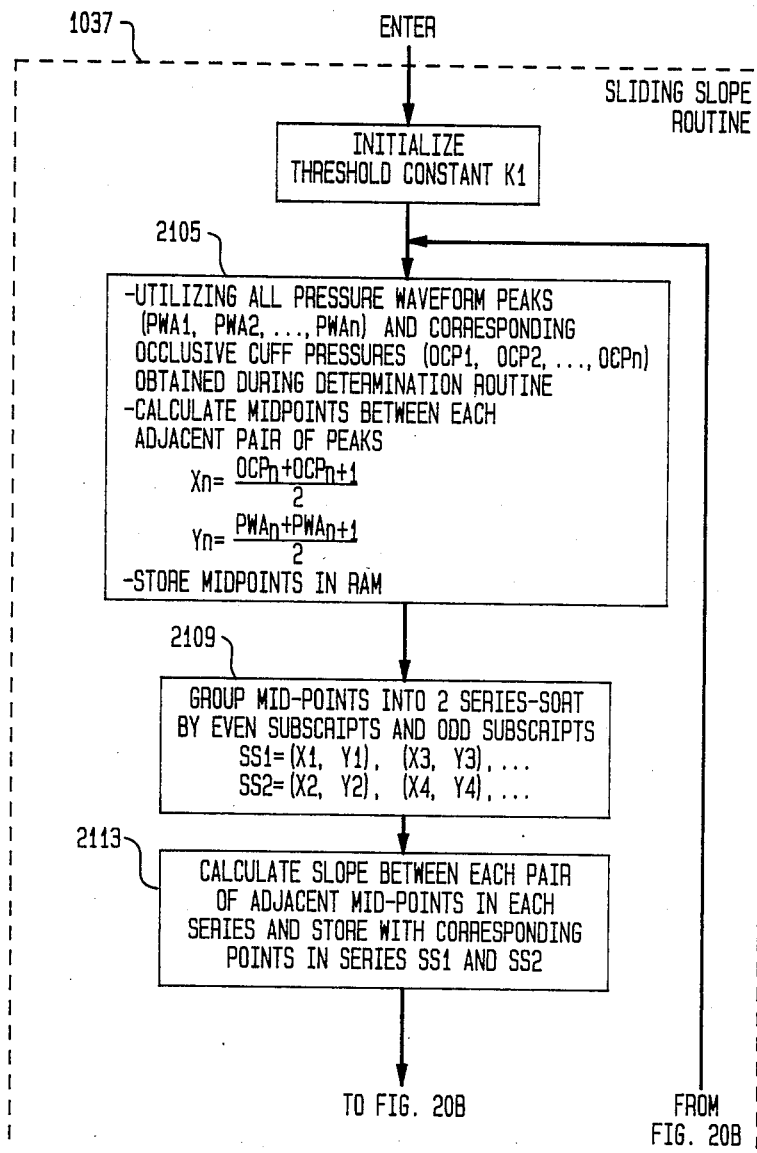

After the mean profile routine 1033 has been executed, a sliding slope diastolic pressure value DPss is ascertained using sliding slope routine 1037 which is shown in flowchart form in FIGS. 20A–B. This routine, like that of the mean profile routine, is premised on the existence of a wide range of non-linear arterial wall elasticity relationships in the human population. The object of the sliding slope routine is to produce highly consistent and extremely accurate diastolic pressure determinations through measuring independent physiologic phenomena which are more directly related to the actual arterial diastolic pressure of any patient than any method known to the art. This thus contrasts with non-invasive pressure-sensing diastolic determination methodologies generally known in the art which assume a pre-determined static relationship (of pressure/displacement elasticity) and derive diastolic pressure determinations based on linear extrapolation of the mean blood pressure peak amplitude values.

In particular, the inventive sliding slope method is independent of the patient's mean blood pressure. In essence, this routine measures the occlusive cuff pressure value at which the declining rate of change of pressure displacement amplitudes (PWAs) becomes significantly less negative, i.e., "flattens-out", as cuff pressure is reduced. Physiologically, this "flattening-out" occurs when the magnitude of the externally-applied occlusive cuff pressure first becomes less than that of the intra-arterial diastolic pressure. Thus, after "flattening out" is reached, any further lowering of the resistance (occlusion) to blood flow becomes less apparent, as indicated by the "bend" in the declining trend of amplitude values in the PWA envelope (see FIG. 19B).

Figure 21E:
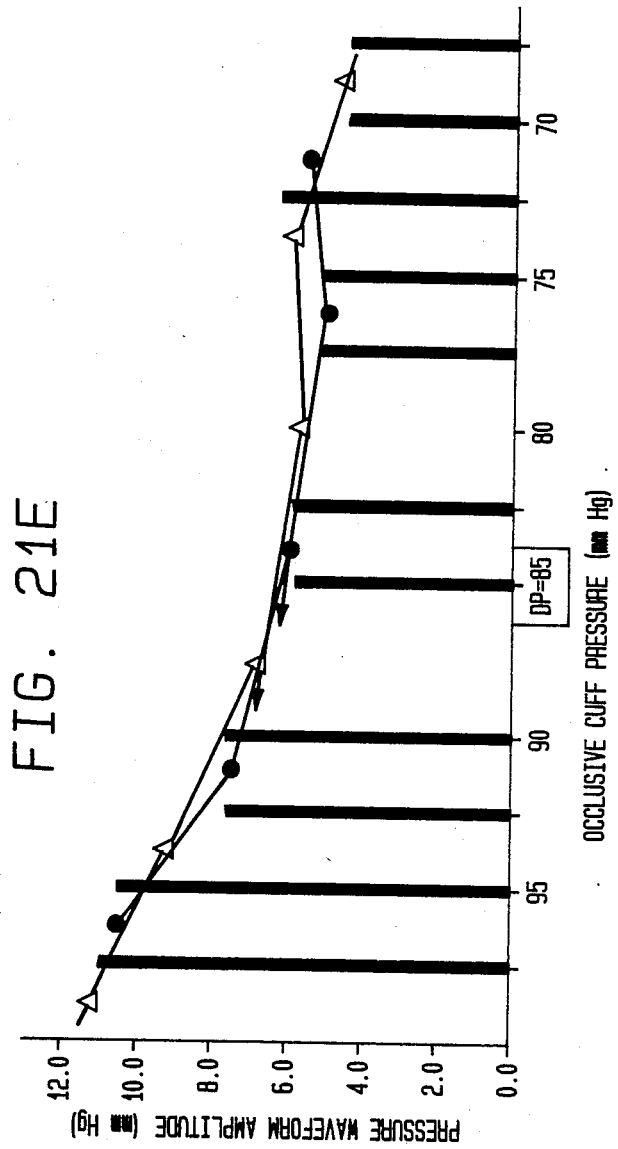

To facilitate understanding of sliding slope routine, its operation will first be graphically described in conjunction with FIGS. 21A–F, in which FIGS. 21A–D depict four different illustrative descending sequences of PWA peaks. Any one of these sequences might occur during occlusive cuff bleed-down, depending on patient condition and movement. FIG. 21A represents a sequence of generally descending PWA pulses in which there is a small amount of peak-to-peak variability. Increasing amounts of variability are shown in the sequences depicted in FIGS. 21B–D.

In essence, this routine determines the peak amplitude and corresponding occlusive cuff pressure mid-points between each sequential pair of detected PWA peaks. These mid-points are then alternately assigned to one of two overlapping (timewise) sequences—identified as either dots or triangles in each of FIGS. 21A–F. For example, as shown in FIG. 21A, the dot sequence, labelled SS2, is comprised of mid-points 2, 4, 6, 8 and 10; while the triangular point sequence, labelled SS1, is comprised of mid-points 1, 3, 5, 7 and 9. The adjacent mid-points in each sequence are connected by line segments (e.g. line segments 1-3, 3-5, 5-7 and 7-9 for SS1) followed by a determination of the slope m for each line segment in each sequence. The slopes for all the segments comprising each sequence are then compared with a pre-defined negative threshold value that is used as a criterion for identifying the value of occlusive cuff pressure that corresponds to when the rate of PWA descent (determined by the slope of each line segment) becomes relatively horizontal or approaches a less negative value (i.e., begins to "flatten-out"). Specifically, "flattening-out" is defined to have occurred in a sequence when two successive segments in that sequence possess slope values that are less (negative) than, or equal to, the negative threshold (illustratively and preferably set at a relatively small value of approximately −0.25). After the point at which "flattening-out" is said to occur is determined for each overlapping sequence, an intermediate diastolic pressure value, dp$_{SS1}$ and dp$_{SS2}$, is selected for each sequence, SS1 and SS2, respectively. Each intermediate value is equal to occlusive cuff pressure corresponding to the respective PWA peaks that immediately precedes the leading mid-point (such as mid-points 5 and 6 in FIG. 21A and those connected to rearward-facing arrows in all the FIGS. 21A-F) of preferably the first-occurring line segment in each sequence (e.g. segments 5-7 and 6-8 in FIG. 21A) that has a slope that is less than the threshold value. The final sliding slope diastolic pressure value, DPss, is then determined as being equal to dp$_{SS1}$, dp$_{SS2}$, or the average value of both. Preferably and as employed in the embodiment described herein, DPss is taken to be dp$_{SS2}$, the occlusive cuff pressure for the PWA immediately preceding the second-to-occur leading mid-point (e.g., mid-point 6 having an occlusive cuff pressure 83 mm(Hg) as shown in FIG. 21A), or the minimum of the two intermediate diastolic values.

With abnormal hemodynamic activity, the PWA peak-to-peak variability may be excessive (such as that shown in FIGS. 21C and 21D) which, in turn, may cause successive line segments to possess a slope value which is alternately less negative than the threshold value and then more negative. Line segments, which possess such a negative slope, are hereinafter referred to as "negators." To minimize the effect of any negator(s) on the sliding slope determination of diastolic pressure, the PWA peak that occurs immediately after each leading mid-point of a negator (labelled as "PWX" in FIGS. 21C and 21D) is removed to result in the sequences shown in FIGS. 21E and 21F which respectively correspond to the original unadjusted sequences depicted in FIGS. 21C and 21D. In addition, if a line segment has a slope in excess of a pre-defined positive threshold, illustratively and approximately (+) 0.25 and occurs immediately prior to any "negator", then it is termed a "reversal", and the PWA causing the "reversal" (labelled "PWR" in FIG. 21D) is also removed in order to minimize its influence on its associated sequence. The selected PWR is the smaller of the PWA's that immediately proceed and follow the leading mid-point of the "reversal" segment. After all the necessary PWA's have been removed to eliminate "negators" and "reversals," each mid-point is re-calculated and assigned to one of two sequences, and line segments that join each pair of adjacent mid-points for each sequence are calculated. The final sliding slope diastolic value, DPss, is determined in the same manner described above.

With the foregoing in mind, sliding slope routine 1037 will now be described in conjunction with the flow-chart shown in FIGS. 20A-B. Upon entry into this routine, execution block 2101 initializes the value of constant $K_1$ to the pre-defined negative threshold value, illustratively and preferably −0.25. Thereafter, block 2105 is executed which calculates the mid-point co-ordinates ($x_n$, $y_n$) for the mid-point of each adjacent PWA pair, PWA$_n$ and PWA$_{n+1}$, using the following equations:

$$x_n = (OCP_n + OCP_{n+1})/2$$

$$y_n = (PWA_n + PWA_{n+1})/2$$

and stores the results in RAM. Once this is accomplished, execution block 2109 successively and alternately assigns these mid-points to sequences SS1 and SS2. The resulting sequences are represented by the following:

$$SS1 = (X_1, Y_1), (X_3, Y_3), \ldots, (X_n, Y_n)$$

$$SS2 = (X_2, Y_2), (X_4, Y_4), \ldots, (X_{n+1}, Y_{n+1})$$

where SS1 is represented by the "triangular" labelled mid-points in FIGS. 21A-F, and SS2 is represented by the "dotted" labelled mid-points also appearing in these figures.

To facilitate understanding the operation of execution blocks 2113, 2117, 2125 and decision block 2121, the operation of these blocks will now be discussed with specific reference to the sequence of PWAs shown in FIG. 21D. Once the mid-points have been assigned to the appropriate sequences, execution block 2113 computes the slope of the line segment connecting each pair of adjacent mid-points in each sequence and stores the results in RAM memory. In this regard, the following slope value computations illustratively would result from the series of PWAs illustratively shown in FIG. 21D:

| Sequence | Mid-Points |             |       |       |       |       |
|----------|------------|-------------|-------|-------|-------|-------|
| SS1      | 1, 3, 5, 7, 9, 11, 13 |  |       |       |       |       |
| SS2      | 2, 4, 6, 8, 10, 12, 14 | |       |       |       |       |
|          | Sequence SS1 Slopes | | |     |       |       |
| Line Segment | 1-3 | 3-5 | 5-7 | 7-9 | 9-11 | 11-13 |
| Slope Values | −.28 | −1.2 | +.6 | −.24 | −.24 | −.12 |
|          | Sequence SS2 Slopes | | |     |       |       |
| Line Segment | 2-4 | 4-6 | 6-8 | 8-10 | 10-12 | 12-14 |
| Slope Values | −.48 | −.92 | +.76 | −.72 | +.08 | −.16 |

Thereafter, execution block 2117 compares each slope value against the pre-defined negative value of $K_1$ (−0.25) and a pre-defined constant positive threshold (which for purposes of the following discussion will be set equal to the positive value of $K_1$, i.e. +0.25) to identify any "negators" and "reversals." In this regard, segment 8-10 of FIG. 21D is labelled as a "negator" and segment 6-8 is labelled as a "reversal." If any "negators" and "reversals" are found, block 2117 identifies and stores the previously defined associated PWX and PWR peaks for use during the diastolic validation routine, which will be discussed shortly. Thereafter, decision block 2121 routes execution via the "Yes" path, to block 2125. This latter block eliminates both the PWX peaks occurring immediately after the leading mid-points of all "negators", and the PWR peaks occurring immediately before or after the leading mid-points of all "reversal" line segments. Thereafter, control transfers to block 2105 which recomputes the mid-points associated with the remaining PWA's. Blocks 2105 and 2109 thereafter assign each of these mid-points to either sequence SS1 or sequence SS2. From there, block 2113 calculates the slope of each line segment connecting an adjacent pair of mid-points in each of these. The following results apply to the sequences illustratively shown in FIG. 21F:

| Sequence | Mid-points |
|---|---|
| SS1 | 1,3,5,7,9,11 |
| SS2 | 2,4,6,8,10,12 |

| Sequence SS1 Slopes | | | | | |
|---|---|---|---|---|---|
| Line Segment | 1-3 | 3-5 | 5-7 | 7-9 | 9-11 |
| Slope Values | −.28 | −.56 | −.27 | −.1 | −.12 |
| Sequence SS2 Slopes | | | | | |
| Line Segment | 2-4 | 4-6 | 6-8 | 8-10 | 10-12 |
| Slope Values | −.48 | −.19 | −.4 | +.08 | −.16 |

In the event of an extremely sharp or flat descending PWA envelope, then the value of the negative threshold constant, $K_1$, is modified by block 2117. For example, if the envelope is characterized by a relatively low number of PWAs and a pronounced peak value, then the value of constant $K_1$ may be preferably set to approximately −0.5. Alternatively, if the envelope is relatively flat and its latter stage descent is very gradual, then the value of constant $K_1$ may preferably be set to a much lower value, such as approximately −0.1. Selection of the appropriate value of this constant is accomplished by computing the overall rate of change in the envelope between the peak envelope amplitude and the approximate diastolic amplitude value. Alternatively, this computation may be combined with the determination of the average rate of change of PWA amplitudes detected prior to the maximum PWA value being reached in the envelope pressure determination. Either of these alternatively computed rate of change factors are then illustratively used to address an appropriate look-up table in order to access one or several predetermined values of constant $K_1$. Alternatively, the determination of $K_1$ may actually be accomplished by computing the quotient of the value of $PWA_{peak}$ divided by the total number of PWAs detected (during the occlusive cuff measurement routine) that occur prior to the one PWA selected as being the final diastolic pressure.

If, after execution of block 2117, decision block 2121 determines that no "negators" or "reversals" remain, then execution block 2129 determines an intermediate diastolic value, $dp_{SS1}$ and $dp_{SS2}$, for each series SS1 and SS2, respectively. Specifically, block 2129 examines the slopes for each sequence to find two adjacent slope values that are smaller than the current positive and negative threshold values (which for purposes of the example shown in FIG. 21F is ±0.25) such as segment pairs 7-9 and 9-11, as well as 8-10 and 10-12. Each intermediate diastolic value is then set equal to the occlusive cuff pressure of the PWA occurring immediately prior to the leading mid-point of the first line segment in each sequence that has a slope which is smaller than the threshold value (such as segments 5-7 and 6-8 in FIG. 21F corresponding to occlusive cuff pressures 83 and 78, respectively). Lastly, block 2133 selects the final sliding slope diastolic pressure value, $DP_{SS}$, as being the minimum of the two intermediate values, which illustratively for this example (FIG. 21F) is 78 mm.

At this phase in the occlusive cuff measurement process, i.e. after both diastolic values ($DP_{mp}$ and $DP_{ss}$) have been determined by mean profile and sliding slope routines 1033 and 1037, respectively, execution then passes to diastolic validation routine 1040.

2.3.2.4 Diastolic Validation Routine 1040

Figure 22:
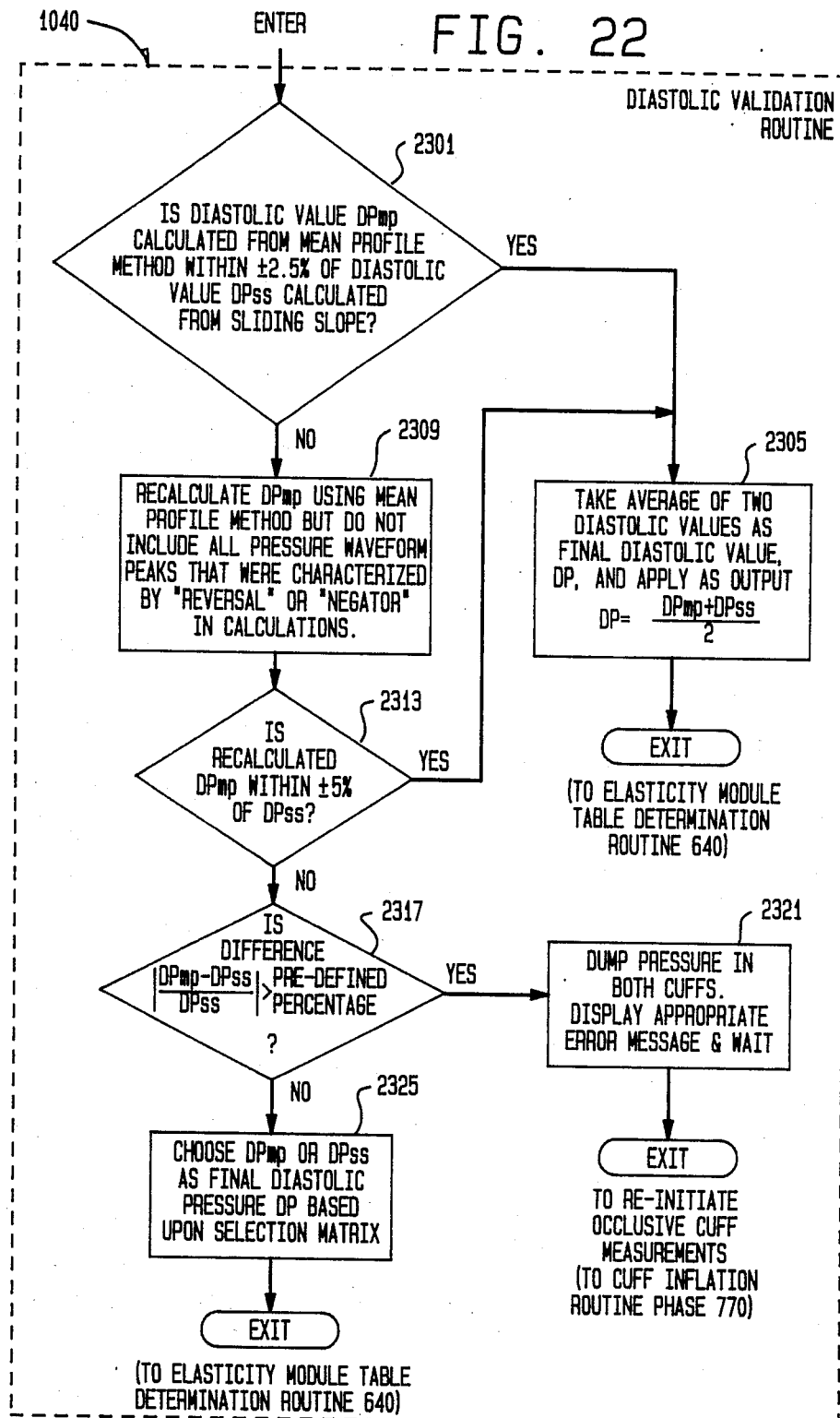
FIG. 22 depicts a flowchart of Diastolic Validation Routine 1040 shown in FIG. 11.

Diastolic validation routine 1040 is shown in flowchart form in FIG. 22. This routine compares the results of the diastolic mean profile and sliding slope routines to select the one that best produces a valid measure of diastolic pressure. Specifically, the selection entails determining which of the two independent diastolic determination routines performed most effectively in view of the actual hemodynamic data encountered during the diastolic measurement phase of the occlusive cuff process. This selection is facilitated since each of the two routines produces an accompanying set of hemodynamic variability data that indicates the relative accuracy of each of the two intermediate diastolic measurement values, $Dp_{mp}$ and $DP_{ss}$. When these two values differ from each other by any significant amount, i.e., 5%, the "selection" is performed based on accessing a pre-determined look-up table that determines which routine is likely to produce the most accurate measurement value. In addition, the value produced by each routine is "validated" through criteria—as previously discussed—resident within each routine which selects a result which is least influenced by hemodynamic variability and also establishes limits on maximum acceptable variability for the selected result. If the variability data of both routines exceeds the limits, a final diastolic pressure measurement value DP does not occur, and the entire occlusive cuff measurement process is repeated.

Specifically, upon entry into diastolic validation routine 1040, decision block 2301 tests both diastolic pressure values, DPmp and DPss, to see if they are within a pre-defined percentage, illustratively ±2½%, of each other. If they are, the final diastolic pressure, DP, is merely taken, via block 2305, as the average of the mean pressure and sliding slope diastolic values. Once this final pressure is determined and appropriately displayed and transmitted, via bi-directional port 232 (see FIG. 1B), execution exits from block 2305 to the previously described elasticity moduli table determination routine 640.

Alternatively, if the difference between these diastolic values is greater than illustratively ±2½%, then execution proceeds, via the "No" path, from decision block 2301, to block 2309. Such a large measurement differential is generally due to significant variability among detected PWA peaks and, to confirm this, block 2309 removes from the final mean profile average computation, the individual PWA peak values, if any, attributable to "reversals" and "negators" designated in the sliding slope routine and then re-computes the diastolic pressure value $DP_{mp}$ using only the remaining PWA peak values. If, decision block 2313 determines that the re-computed mean profile value $DP_{mp}$ is then within ±5% of the sliding slope DPss value, then execution proceeds, via the "Yes" path from block 2313, to block 2305.

If, however the remaining difference between these diastolic values, $DP_{mp}$ and $DP_{ss}$, is still greater than illustratively 5%, control is routed from decision block 2313 to decision block 2317. If the amount of variability inherent in the data used in both the sliding slope and mean profile methods is excessive, then neither DPss or DPmp pressure measurements can be relied upon for an accurate final diastolic measurement. Specifically, block 2317 tests for the existence of an excessive level of variability, and if this is found, the current occlusive cuff measurement process is first terminated through execution of block 2321 and second another occlusive cuff measurement process is initiated by transferring control to cuff inflation routine 770. Specifically, if one "negator" or more than one "negator" or "reversal" was identified during the sliding slope routine and the differential range of individual PWA diastolic values, d(i-3) through d(i), determined in the mean profile routine exceeds 16%, then decision block 2317 transfers control to execution block 2321 which terminates the present occlusive cuff measurement process.

Alternatively, if the variability is not excessive, then control passes, via the "no" path from decision block 2317, to execution block 2325 which uses a selection matrix to select either DPmp or DPss as the final diastolic pressure, DP. Specifically, the selection matrix that specifies the particular value based on a computed percentage differential of individual PWA diastolic values d(i) and the previously determined total number of "negators" and "reversals." An illustrative selection matrix is provided below; however the particular selection criteria used in practice may based upon empirical study vary from that indicated therein.

| Sliding Slope Variability | Range Variation of Individual Mean Profile Diastolic Values Used for DPmp Computations Percentage Differential | | |
|---|---|---|---|
| | 0 to ±6% | ±6 to 12% | ±12% or more |
| No negators | SS | SS | SS |
| One negator | MP | Average | SS |
| Two or more negators or reversals | MP | MP | MP | where SS signifies sliding slope method--use DPss value; MP signifies mean pressure method--use DPmp value; and "Average" signifies taking the average of DPss and DPmp.

It is quite apparent that the use of both separate occlusive and waveform sensing cuffs enables the system to be connected to several limb positions of the patient; preferably the two cuffs are positioned on the patient's opposite upper arms or thighs. However, when medical treatment dictates that the cuffs be positioned on the same limb, the constant pressure waveform sensing cuff is preferably located distal (e.g. at the wrist or ankle) to the position of the occlusive cuff (e.g. upper arm or thigh). In these specialized situations, constant pressure calibration sampling using the waveform sensing cuff cannot occur until after the systolic and diastolic calibration values are determined via occlusive cuff. Thus, in these situations, computer 200 detects the absence of any pulses detected through the waveform sening cuff and, in response thereto, extends the length of "calibration" phase until all residual applied occlusive cuff pressure has been eliminated in order to permit additional pressure displacement waveform sampling for the determination of base level, peak, trough, and reference pressure values. Consequently, during any such "calibration" phase, which can extend to a total duration of about 40 seconds, continuous pressure monitoring based on the look-up table data (from the prior calibration phase) is interrupted in lieu of being performed essentially simultaneously with, the current "calibration" phase as in the preferred embodiment described above.

During any "calibration" phase, using opposite limb connections, each heart-beat-generated pressure waveform is simultaneously detected as a series of pressure displacement waveform values as part of both the occlusive cuff pressure perturbations and perturbations to the constant reference pressure signal produced by the waveform sensing cuff. Simultaneous, or near simultaneous sampling (detection timing differences result from different arterial pathway distances to each of the cuffs and waveform propogation rates therethrough) of each sequentially occurring waveform at different artery-limb locations and applied pressure values enables highly accurate definition of hemodynamic activity during the occlusive cuff calibration measurement routines.

Computer 200 also determines if the two cuffs are affixed to different limbs, inasmuch as this is the preferred interconnection scheme for continuous monitoring. This scheme is identified as existing if pressure displacement waveforms detected through the waveform sensor cuff are not attenuated during inflation of the occlusive cuff to suprasystolic pressure during execution of any "calibration" phase. Once opposite limb interconnection has been identified, certain simplified measurement processes and supplemental processes, as will now be described, are implemented during the "calibration" and "continuous monitoring" phases. First, execution block 1271 computations of API values in Pulse Window Interrogation (PWI) routine 1250 (which is executed in conjunction with systolic routine 1020) is simplified by the fact that heart-rate waveform peak-to-peak intervals are determined based on low pressure waveform sensing cuff sampling instead of being being taken from occlusive cuff sample data. Thus, blocks 1261-1265 of the PWI routine (see FIG. 13A) are not used during calibration with opposite limb sensing, and occlusive cuff absent pulse windows (APW) are instantaneously identified, without the use of TAPW designations and redesignations, during systolic routine 1020. Second, opposite limb sensing provides for effective identification of the occurrence of any artifacts (e.g., aberrant limb movement data that can obfuscate valid pressure displacement waveform sampling data) so that false data can be identified and rejected in order to prevent erroneous calibration measurement values. Specifically, a comparison of the two opposite limb sampling sequences of PWA values readily enables the identification of any artifact "pulse" occurring in either sequence. If a disproportionate peak amplitude value, with respect to one or more prior and subsequent amplitude values, is measured in a waveform in one of the two sequences, disproportionate peak amplitude value must exist with respect to the corresponding waveform in the other sequence. If a disproportionate value exists in the PWA sequence produced through one cuff but not in that produced by the other cuff, then this disproportionate value is identified as an artifact instead of as a valid pressure displacement waveform and is thus not used in the measurement process. While this comparative process can be used to test either sampling sequence for artifacts, this process is particularly germane to the occlusive cuff sampling data where artifact amplitudes can be similar in relative magnitude to those of pressure displacement waveforms occurring during execution of occlusive cuff measurements routine 630.

While the preferred embodiment of the non-invasive blood pressure measurement system previously described herein involves the use of two separate cuffs—one for occlusive cuff calibration measurement and the other for pressure displacement waveform monitoring at a constant low pressure, it is readily apparent that a single occlusive cuff and a single channel of analog electronic components might alternatively be employed. The methods of the preferred embodiment, as described above with respect to two cuffs interconnected to the same limb, would generally be used even if single, occlusive blood pressure cuff were to be used instead. Specifically, the system would generally operate as described above, although continuous monitoring would be interrupted during the "calibration" phase. Furthermore, at the completion of occlusive cuff measurement routine 630, the occlusive cuff pressure would be abruptly deflated to approximately 40 mm(Hg). Thereafter, sampling for the "continuous monitoring" phase, would proceed using the occlusive cuff channel in lieu of a separate waveform sensor cuff channel.

Of course, it is readily apparent for those skilled in the art that while the invention has been described in terms of a system for measuring human blood pressure, the invention can be easily extended to a system for measuring the pressure of any pulsatile flowing fluid. The basic requirement for any such system is that the fluid must flow through an elastic tube in which the radial distension (movement) of the wall of the tube varies as a pre-defined function of the fluidic pressure therein. This distension/pressure function can be either linear or non-linear. Means such as, but not limited to, electrically-operated valves and the like, can be used to restrict or stop the pulsatile fluid flow in order to establish a plurality of pre-defined wall distension/fluid pressure boundary conditions. The particular means chosen may be dependent upon various physical properties of the actual fluid being measured, such as but not limited to its corrosivity, and various other physical constraints, such as but not limited to whether a vessel of appropriate elastic properties can be easily inserted anywhere downstream of the point at which the flow restricting device is installed. During execution of the "calibration" phase, the measured distension of the wall of the tube occurring at each of the boundary conditions is used to determine the values of all the necessary coefficients appearing in the pre-defined radial wall distension/pressure function. Thereafter, the system "continuously monitors" the pressure based upon any subsequently occurring wall distensions. Re-calibration is initiated at discrete intervals of time to insure accurate pressure readings. The durations of these intervals might be long (e.g., weeks or months) or short, depending on the physical characteristics of the system, and might adaptively change based upon the amount of variation in the value of one or more of these coefficients occurring between any past calibration interval, such as the most recent one, to another calibration interval, such as the present one. As the amount of this variation increased, the duration between successive re-calibrations correspondingly decreases. Likewise, if little variation occurred, then this duration correspondingly increases.

Although a specific illustrative embodiment has been shown and described herein, this merely illustrates the principles of the present invention. Many varied arrangements embodying these principles may be devised by those skilled in the art without departing from the spirit and scope of the invention.

I claim:

1. A method tor use in determining arterial blood pressure in a subject comprising the steps of:

undertaking a calibration phase comprised of the steps of determining blood pressure and arterial wall displacement values of said subject occurring in response to corresponding initial conditions of blood flow, and ascertaining, in response to said determined values, the values of a plurality of coefficients, each of which is associated with a corresponding term in a pre-defined relationship that characterizes arterial blood pressure as a function of arterial wall displacement, undertaking a continuous monitoring phase comprised of the steps of measuring subsequently occurring actual arterial wall displacement values, generating a corresponding blood pressure value in response to said relationship and to at least one of each of said actual arterial displacement values, and repeating said calibration phase at the occurrence of any one of a plurality of pre-defined events or at pre-defined times.

2. The method of claim 1 wherein said continuous monitoring phase undertaking step is further comprised of the step or varying said times in response to differences between the most recent value and a corresponding prior value of at least one of said coefficients.

3. The method of claim 2 wherein said generating step is further comprised of the step of producing various measurement parameters based upon said generated blood pressure values.

4. The method of claim 3 wherein said repeating step is comprised of the steps of:

checking various ones of said measurement parameters against corresponding limit values, and repeating said calibration phase whenever at least one of said measurement parameters exceeds its corresponding limit value.

5. The method of claim 1 wherein said determining step is comprised of the steps of:

affixing at least one arterial occluding device to at least one limb of a subject, controllably operating said occluding device to non-invasively occlude an artery within said limb and thereby establish an initial condition of arterial blood flow, sensing perturbations, in the arterial blood flow through said occluding device, as said device reduces its occlusion at a controlled rate so as to establish other initial conditions of arterial blood flow, and determining, in response to the value of said perturbations, values of arterial blood pressure and arterial wall displacement occurring at each of said initial conditions of arterial blood flow.

6. The method of claim 5 in which said operating step further includes the step of measuring said perturbations through said occluding device and controllably increasing the occlusion produced by said device to a value in excess of that required to eliminate said perturbations, whereby an initial condition of supra-systolic occlusion is achieved.

7. The method of claim 6 in which said measuring step includes the step of inflating a pneumatic cuff attached around a selected limb of the subject and sensing pulsatile perturbations occurring in the air contained in the cuff and attributable to pulsatile arterial blood flow.

8. The method of claim 7 in which said inflating step further includes the steps of:

attaching a relatively high pressure occlusive pneumatic cuff and a low pressure waveform sensing cuff around at least one limb of the subject, controllably inflating the occlusive cuff first to a supra-systolic occlusive pressure and then deflating the occlusive cuff to a sub-diastolic occlusive pressure in order to produce said initial conditions of arterial blood flow, inflating said low pressure waveform sensing cuff simultaneously with said occlusive cuff and thereafter maintaining air pressure at a substantially constant low pressure during deflation of said occlusive cuff, and measuring the relative displacement of the arterial wall attributable to the arterial blood flow occurring for each of said initial conditions as a function of the simultaneously occurring pulsatile variation in the pressure of said waveform sensing cuff.

9. The method of claim 8 wherein the attaching step further includes the steps of securing the occlusive cuff around a selected limb of the subject and securing the waveform sensing cuff on the same limb but at a location distally situated from said occulsive cuff.

10. The method of claim 8 wherein the attaching step further includes the step of securing the occlusive and waveform sensing cuffs to different limbs of the subject.

11. The method of claim 10 wherein the securing step includes the step of positioning the occlusive and waveform sensing cuffs on opposite limbs of the subject.

12. The method of claim 1 wherein the ascertaining step further includes the step of substituting each of a pre-selected plurality of arterial wall displacement values into said pre-defined relationship in order to fabricate a table of arterial blood pressure values corresponding to said pre-selected plurality of displacement values.

13. The method of claim 12 wherein the generating step includes the step of using at least one of said actual arterial displacement values to access the table in order to determine a generated blood pressure value corresponding thereto.

14. The method of claim 13 wherein the generating step is further comprised of fabricating a sequence of present and previously generated blood pressure values for display on an historical basis.

15. The method of claim 14 wherein the generating step is further comprised of fabricating respective sequences of present and prior values for each of a plurality of measurement parameters, wherein said parameters are determined in response to said generated blood pressure values.

16. The method of claim 15 wherein the generating step is further comprised of providing a suitable notification whenever any value of any of said sequences exceeds a pre-defined limit value.

17. The method of claim 16 wherein the fabricating step includes the step of producing systolic and diastolic arterial blood pressure values.

18. The method of claim 1 wherein said determining step further includes the step of producing a systolic blood pressure value, and generating at least first and second diastolic blood pressure measures and selecting either one of said measures as a final diastolic pressure value in response to hemodynamic variability detected during said calibration phase.

19. The method of claim 18 wherein said systolic value producing step includes the steps of:

controllably deflating an occlusive cuff secured around a limb of the subject, detecting a pre-determined number of pressure waveform peaks and simultaneously occurring corresponding occlusive cuff pressures occurring during occlusive cuff deflation, determining a measure of the variability of these detected peaks, defining co-ordinates of a first point in terms of an average of the detected peaks and an average of the corresponding occlusive cuff pressures, successively maintaining the pressure of said occlusive cuff at a substantially constant value for a corresponding pre-selected time interval and detecting additional pressure waveform peaks and determining a second measure of the variability associated therewith during said corresponding time interval, defining co-ordinates of a second point in terms of an average of said additional peaks and said constant pressure value, modifying the values of the co-ordinates of said first and/or second points, in response to said first and/or second variability measures, ascertaining an intermediate value of systolic pressure in terms of the co-ordinates of a point of intersection between a line defined by said first and second points and a line representing a pre-determined constant pressure value, and modifying said intermediate systolic pressure value in response to said first and/or second variability measures so as to obtain a final systolic pressure value.

20. The invention in claim 19 in which said deflating step further includes the step of deflating the occlusive cuff at a pre-defined controlled linear rate.

21. The invention in claim 19 in which the peak detecting step includes the step of sampling pneumatic pressure of said occlusive cuff during each of a pre-defined number of sequentially occurring sampling windows, each of said windows being a pre-determined duration, to detect either a pressure waveform peak or an absent pulse occurring during any of said windows.

22. The invention in claim 21 in which the sampling step further includes the step of varying the duration of said sampling windows in response to either the actual heart-rate of the subject and/or previously occurring absent pulse windows.

23. The invention in claim 19 in which said maintaining step includes the step of selecting the duration of said pre-selected time interval based upon the number of pressure peaks and absent pulse windows and the order in which said peaks and absent pulse windows occur during this interval.

24. The invention in claim 23 in which said maintaining step further includes the step of determining the value of said variability measure in terms of the number of absent pulse windows detected during a pre-selected sequence of sampling windows.

25. The invention in claim 19 in which said intermediate systolic value ascertaining step includes the step of determining the x co-ordinate value of said point of intersection and setting said intermediate systolic value equal to the value of the x co-ordinate.

26. The invention in claim 18 in which said first diastolic measure generating step includes the steps of:

determining a group, of a pre-selected number of sequentially occurring individual pressure waveform values, from all the pressure waveforms occurring during deflation of an occlusive cuff, wherein said group possesses maximum average amplitude, selecting, in accordance with pre-selected criteria, at least one individual pressure waveform from the group and setting mean pressure of the subject equal to the occlusive cuff pressure corresponding to the selected individual pressure waveform, determining the systolic pressure of the subject, and ascertaining the first measure of diastolic pressure in accordance with the formula:

$$D = \frac{Am - Sy}{(A - Y)}$$

for at least a chosen one of all of said pressure waveforms in which

D is the first measure of diastolic pressure, A is the uncalibrated peak amplitude of said chosen pressure waveform, Y is the mean value (area/duration) of said chosen pressure waveform, and S and M are the systolic and mean pressure values respectively, associated with said subject.

27. The invention in claim 26 in which said selecting step is comprised of the steps of determining a second group of a preselected number of sequentially occurring pressure waveforms from all of said waveforms occurring subsequent to said selected individual pressure waveform.

28. The invention in claim 27 in which the selecting step includes the step of ascertaining the mean pressure as being subsequently equal to the occlusive cuff pressure occurring at the time of the peak of said selected individual pressure waveform.

29. The invention in claim 28 in which the first measure ascertaining step further includes the step of determining, in accordance with said formula, a diastolic pressure estimate for each pressure waveform in said second group and averaging all the estimates to produce said first measure of diastolic pressure.

30. The invention in claim 26 in which said individual pressure waveform selecting step is comprised of the steps of:

determining whether said selected individual waveform was caused by an artifact by comparing the peak amplitude of said selected individual waveform against a pre-determined limit, and rejecting the selected individual waveform in the event the limit is exceeded and selecting another waveform until such limit is no longer exceeded.

31. The invention in claim 18 in which said second diastolic measure generating step includes the steps of:

a. establishing, in response to a sequence of occlusive pressure waveform peaks and corresponding occlusive cuff pressures occurring during deflation of the occlusive cuff, a sequence of mid-point co-ordinates, wherein one co-ordinate of each midpoint is an average of the peak amplitudes of two successive pressure waveforms and the other co-ordinate of each mid-point is an average of the occlusive cuff pressures corresponding to each of said two peaks, b. grouping every mid-point into an alternate one of at least two series, c. determining the value of slope of each of a plurality of line segments, wherein each segment joins a pair of adjacent midpoints in one of said sequences, d. testing each of said slope values against pre-defined limits to determine whether any of said mid-points is attributable to a negator or a reversal, e. removing any pressure waveform peak and its corresponding occlusive cuff pressure value attributable to a negator or a reversal from the sequence and repeating steps (a), (b), (c) and (d) until substantially all pressure waveform peaks attributable to either negators or reversals have been removed, f. comparing the slope of each segment in each series against a pre-defined threshold and, in response thereto, choosing an appropriate one of the segments comprising each series, g. choosing an appropriate pressure waveform peak amplitude value that precedes the leading midpoint associated with the chosen segment in each series, and h. selecting one of the resulting chosen pressure waveform peak amplitude values as the second diastolic measure.

32. The invention in claim 31 wherein said selecting step includes the step of picking that one of the chosen waveform peak amplitude values which has the minimum peak amplitude as the second diastolic measure.

33. The invention in claim 18 wherein said selecting step includes the step of picking said first, said second, or an average of said first and second diastolic pressure measures for said final diastolic pressure value in response to a numerical difference between the values of said first and second measures and/or the number of negators and reversals determined during said second diastolic measuring step.

34. Apparatus for determining arterial blood pressure in a subject comprising:

means for undertaking a calibration phase comprising means for determining the blood pressure values occurring in response to corresponding initial conditions of blood flow, and means for ascertaining, in response to said determined blood pressure values, the values of a plurality of coefficients, each of which is associated with a corresponding term in a pre-defined relationship that characterizes arterial blood pressure as a function of arterial wall displacement, means for undertaking a monitoring phase comprising means for measuring subsequently occurring acutal arterial wall displacement values, means for generating a corresponding blood pressure value in response to said relationship and to at least one of each of said actual arterial displacement values, and means for repeating said calibration phase at the occurrence of any one of a plurality of pre-defined events or at pre-defined times.

35. The apparatus of claim 34 wherein said monitoring phase undertaking means is further comprised of means for varying said times in response to differences between the most recent value and a corresponding prior value of at least one of said coefficients.

36. The apparatus of claim 35 wherein said generating means is further comprised of means for producing various measurement parameters based upon said generated blood pressure values.

37. The apparatus of claim 36 wherein said repeating means is comprised of:

means for checking various ones of said measurement parameters against corresponding limit values, and means for repeating said calibration phase whenever at least one of said measurement parameters exceeds its corresponding limit value.

38. The apparatus of claim 37 wherein said determining means is comprised of:
    means for occluding an artery situated in one limb of a subject,
    means for controllably operating said occluding means to non-invasively occlude said artery within said limb and thereby establish an initial condition of arterial blood flow,
    means for sensing perturbations, in the arterial blood flow through said occluding means, as said occluding means reduces its occlusion at a controlled rate so as to establish other initial conditions of arterial blood flow, and
    means for determining, in response to the value of said perturbations, values of arterial blood pressure and arterial wall displacement occurring at each of said initial conditions of arterial blood flow.

39. The apparatus of claim 38 in which said operating means is comprised of: means for measuring said perturbations through said occluding means and controllably increasing the occlusion produced by said occluding means to a value in excess of that required to eliminate said perturbations, whereby an initial condition of supra-systolic occlusion is achieved.

40. The apparatus of claim 39 in which said measuring means includes means for inflating a pneumatic cuff attached around a selected limb of the subject and sensing pulsatile perturbations occurring in the air contained in the cuff and attributable to pulsatile arterial blood flow.

41. The apparatus of claim 40 in which said inflating means is comprised of:
    a relatively high pressure occlusive pneumatic cuff and a low pressure waveform sensing cuff, each of which is attached around at least one limb of the subject,
    means for controllably inflating the occlusive cuff first to a supra-systolic occlusive pressure and then deflating the occlusive cuff to a sub-diastolic occlusive pressure in order to produce said initial conditions of arterial blood flow,
    means for inflating said low pressure waveform sensing cuff simultaneously with said occlusive cuff and thereafter maintaining air pressure at a substantially constant low pressure during deflation of said occlusive cuff, and
    means for measuring the relative displacement of the arterial wall attributable to the arterial blood flow occurring for each of said initial conditions as a function of the simultaneously occurring pulsatile variation in the pressure of said waveform sensing cuff.

42. The apparatus of claim 41 wherein the occlusive cuff is secured around a selected limb of the subject and the waveform sensing cuff is secured around the same limb but at a location distally situated from said occlusive cuff.

43. The apparatus of claim 41 wherein the occlusive and waveform sensing cuffs are secured around different limbs of the subject.

44. The apparatus of claim 43 wherein the occlusive and waveform sensing cuffs are secured around opposite limbs of the subject.

45. The apparatus of claim 34 wherein the ascertaining means is comprised of means for substituting each of a pre-selected plurality of arterial wall displacement values into said pre-defined relationship in order to fabricate a table of arterial blood pressure values corresponding to said pre-selected plurality of displacement values.

46. The apparatus of claim 45 wherein the generating means comprises means for accessing the table, using at least one of said actual arterial displacement values, in order to determine a generated blood pressure value corresponding to said arterial displacement value.

47. The apparatus of claim 46 wherein the generating means is further comprised of means for fabricating a sequence of present and previously generated blood pressure values for display on an historical basis.

48. The apparatus of claim 47 wherein the generating means is further comprised of means for fabricating respective sequences of present and prior values for each of a plurality of measurement parameters, wherein said parameters are determined in response to said generated blood pressure values.

49. The apparatus of claim 48 wherein the generating means is further comprised of means for providing a suitable notification whenever any value of any of said sequences exceeds a pre-defined limit value.

50. The apparatus of claim 48 wherein the fabricating means is comprised of means for producing systolic and diastolic arterial blood pressure values.

51. A method for use in determining arterial blood pressure in a subject, comprising the steps of:
    undertaking a calibration phase comprised of the steps of determining blood pressure values and values of a physiologic parameter of said subject related to blood pressure both values occurring in response to corresponding initial conditions of blood flow, and ascertaining, in response to said determined values, the values of a plurality of coefficients, each of which is associated with a corresponding term in a pre-defined relationship that characterizes arterial blood pressure as a function of said physiologic parameter; and
    undertaking a continuous monitoring phase comprised of the steps of measuring subsequently occurring actual values of said physiologic parameter, generating a corresponding blood pressure value in response to said relationship and to at least one of each of said actual physiologic parameter values, and repeating said calibration phase at the occurrence of any one of a plurality of pre-defined events or at pre-defined times.

52. The method of claim 51 wherein the determining and measuring steps include the step of detecting the physiologic parameter through non-invatsive means or through perivascular invasive means, and wherein the physiologic parameter is proportional to arterial wall displacement, arterial blood flow, arterial blood volume or arterial blood velocity.

53. The method of claim 52 wherein the detecting step further includes the step of sensing said physiologic parameter through non-invasive strain gage plethysmography or electrical impedance plethysmography.

54. The method of claim 52 wherein said continuous monitoring phase further includes the step of varying said times in response to differences between the most recent value and a corresponding prior value of at least one of said coefficients.

55. The method of claim 54 wherein said generating step includes the step of producing various measurement parameters based upon said generated blood pressure values, and said repeating step includes the steps of: checking various ones of said measurement parameters against correponding limit values, and repeating said calibration phase whenever at least one of said measurement parameters exceeds its corresponding limit value.

56. The method of claim 52 wherein the ascertaining step further includes the step of substituting each of a pre-selected plurality of said physiologic parameter values into said pre-defined function in order to fabricate a table or arterial blood pressure values corresponding to said pre-selected plurality of physiologic parameter values, and said generating step further includes the step of using at least one of said actual physiologic parameter values to access the table in order to determine a generated blood pressure value corresponding thereto.

57. The method of claim 56 wherein the generating step further includes the step of fabricating a sequence of present and previously generated blood pressure values and, in response thereto, producing systolic and diastolic arterial blood pressure values.

* * * * *